US012648730B2

(12) United States Patent
Noh et al.

(10) Patent No.: US 12,648,730 B2
(45) Date of Patent: Jun. 9, 2026

(54) TEST METHOD AND APPARATUS FOR EVALUATING COGNITIVE FUNCTION DECLINE

(71) Applicant: EMOCOG Co., Ltd., Seoul (KR)

(72) Inventors: Yoo Hun Noh, Seoul (KR); Hai Rin Kim, Seoul (KR); Ju Hye Kim, Seoul (KR)

(73) Assignee: EMOCOG Co., Ltd., Seoul (KR)

( * ) Notice: Subject to any disclaimer, the term of this patent is extended or adjusted under 35 U.S.C. 154(b) by 401 days.

(21) Appl. No.: 18/142,174

(22) Filed: May 2, 2023

(65) Prior Publication Data

US 2023/0346298 A1      Nov. 2, 2023

(30) Foreign Application Priority Data

May 2, 2022      (KR) ......................... 10-2022-0054152
Apr. 26, 2023      (KR) ......................... 10-2023-0054778

(51) Int. Cl.
*A61B 5/00*      (2006.01)
(52) U.S. Cl.
CPC .................................. *A61B 5/4088* (2013.01)
(58) Field of Classification Search
CPC ....... A61B 5/4088; A61B 5/7475; A61B 5/16; A61B 5/4082; A61B 5/4803; G16H 10/20; G16H 50/30
See application file for complete search history.

(56) References Cited

U.S. PATENT DOCUMENTS

2022/0044824 A1      2/2022   Severson et al.

FOREIGN PATENT DOCUMENTS

| CN | 103561651 A | 2/2014 |
|---|---|---|
| CN | 110633362 A | 12/2019 |
| CN | 111341417 A | 6/2020 |
| CN | 114343577 A | 4/2022 |
| JP | 2016071897 A | 5/2016 |
| JP | 2017144252 A | 8/2017 |
| JP | 2021097913 A | 7/2021 |
| JP | 2013165416 A | 11/2023 |
| JP | 2023165415 A | 11/2023 |

(Continued)

OTHER PUBLICATIONS

Buschke, Herman et al., "Diagnosis of early dementia by the Double Memory Test: Encoding specificity improves diagnostic sensitivity and specificity," The American Academy of Neurology, vol. 48, No. 4, pp. 989-997, Apr. 1997.

(Continued)

*Primary Examiner* — Scott M. Getzow
(74) *Attorney, Agent, or Firm* — Dinsmore & Shohl LLP; Yongsok Choi, Esq.

(57)      ABSTRACT

Provided are a test method and apparatus for evaluating cognitive function decline. The test method for evaluating cognitive function decline includes performing a testing stage of testing how many missions presented for each of a plurality of test items a user performs, and calculating a test score for each of the plurality of test items, performing a category classifying stage of classifying at least one test item from among the plurality of test items as one neurocognitive category from among a plurality of neurocognitive categories, and performing an evaluating stage of evaluating whether there is cognitive function decline in the one neurocognitive category, based on a test score of the at least one test item classified as the one neurocognitive category.

15 Claims, 127 Drawing Sheets

(56) References Cited

FOREIGN PATENT DOCUMENTS

| KR | 1020120107736 A | 10/2012 |
| KR | 1020180109529 A | 10/2018 |
| KR | 101914736 B1 | 11/2018 |
| KR | 102080320 B1 | 2/2020 |
| KR | 102106399 B1 | 5/2020 |
| KR | 1020200065529 A | 6/2020 |
| KR | 102288797 B1 | 8/2021 |
| KR | 102301955 B1 | 9/2021 |
| KR | 102301143 B1 | 10/2021 |
| WO | 2018131542 A1 | 7/2018 |

OTHER PUBLICATIONS

Oh, Jung Eun et al., "Social Cognition Deficits of Schizophrenia in Cartoon Task," Journal of Korean Neuropsychiatric Association, vol. 44, No. 3, pp. 295-302, May 2005.

Dziobek, Isabel et al., "Introducing MASC: A Movie for the Assessment of Social Cognition," Journal of Autism and Developmental Disorders, vol. 36, No. 5, pp. 623-636, Jul. 2006.

Zarino, Barbara et al., "A new standardization of semantic verbal fluency test," Journal of Neurological Sciences, vol. 35, No. 9, pp. 1405-1411, Sep. 2014.

Kim, Jung Wan et al., "The distinctive effect of providing syllables in letter fluency testing: Literate vs. illiterate elderly persons," Journal of Speech Communication, vol. 70, pp. 42-48, Jun. 2015.

LET'S TRY AGAIN

WELL DONE
MAIN TEST WILL START NOW

505

507

PLEASE SAY AS MANY WORDS AS YOU CAN
THAT ARE ANIMALS FOR 30 SECONDS
PLEASE PRESS MICROPHONE BELOW AND ANSWER LOUDLY

THANK YOU
NEXT TEST WILL CONTINUE

THANK YOU
NEXT TEST WILL CONTINUE

THANK YOU
NEXT TEST WILL CONTINUE

THANK YOU
NEXT TEST WILL CONTINUE

PREVIOUSLY, WE HAVE TESTED
HOW MANY COLORS WERE IN DRAWINGS
LET'S RECALL DRAWINGS

FIG. 8H

THANK YOU
NEXT TEST WILL CONTINUE

LET'S TRY AGAIN

FIG. 9F

WELL DONE
MAIN TEST WILL START NOW

THANK YOU
NEXT TEST WILL CONTINUE

WELL DONE
MAIN TEST WILL START NOW

FIG. 90

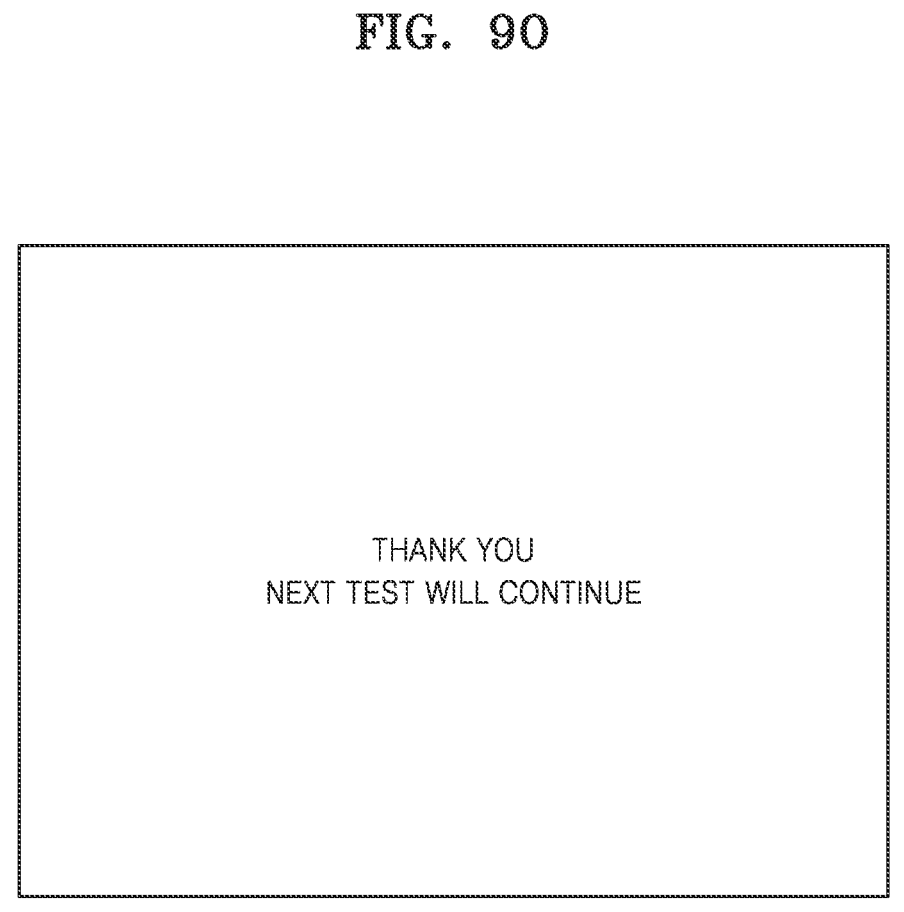

THANK YOU
NEXT TEST WILL CONTINUE

WELL DONE
MAIN TEST WILL START NOW

FIG. 10G

THANK YOU
NEXT TEST WILL CONTINUE

THANK YOU
NEXT TEST WILL CONTINUE

THANK YOU
NEXT TEST WILL CONTINUE

FIG. 14B

PLEASE LISTEN TO INSTRUCTION CAREFULLY

THIS IS TEST OF LISTENING TO SHORT STORY
AND ANSWERING QUESTIONS

LET'S TRY AGAIN

FIG. 15F

WELL DONE
MAIN TEST WILL START NOW

ALL TESTS ARE COMPLETED
PLEASE WAIT AWHILE AND TEST RESULTS WILL BE PRINTED OUT

FIG. 20

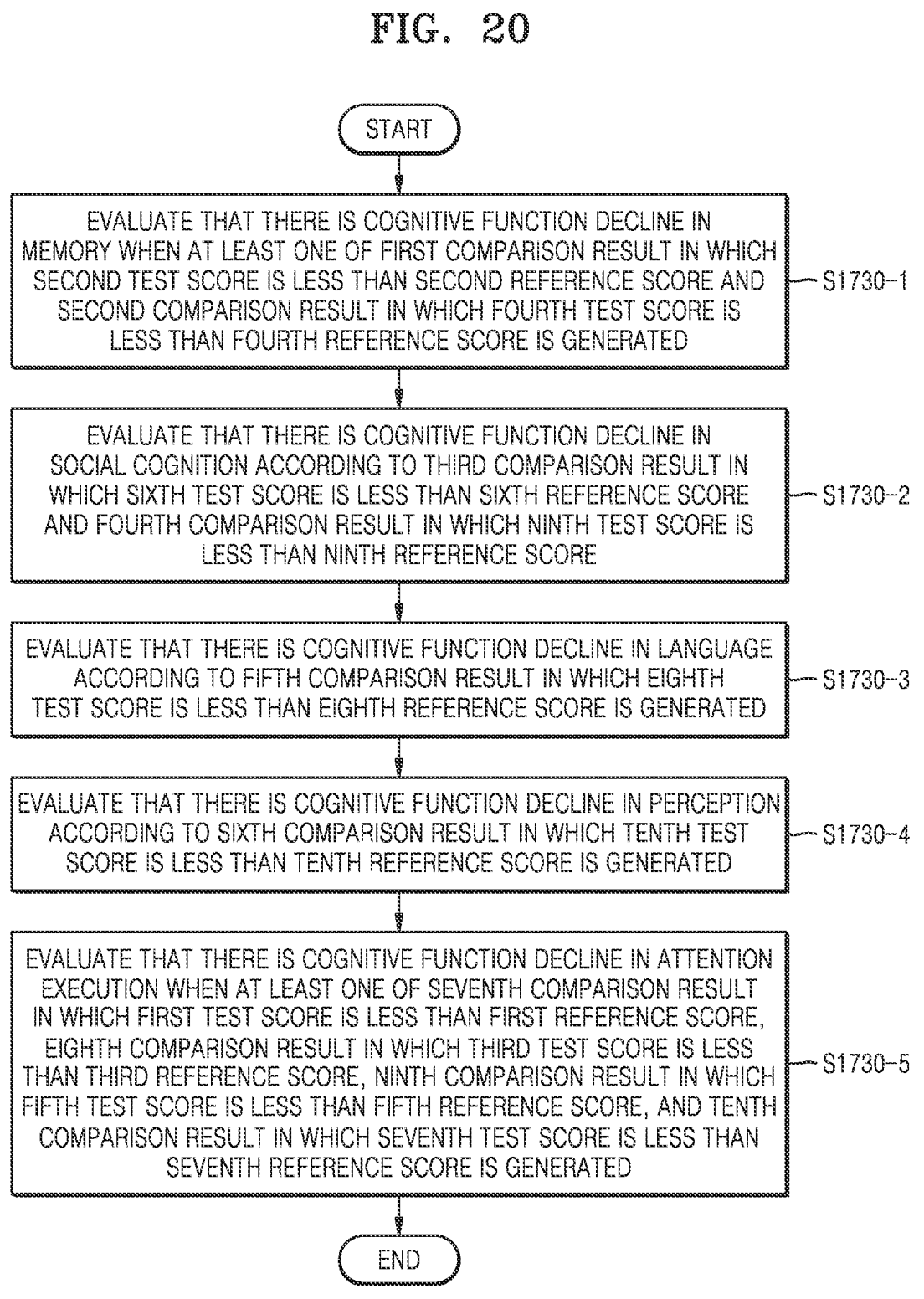

START

EVALUATE THAT THERE IS COGNITIVE FUNCTION DECLINE IN MEMORY WHEN AT LEAST ONE OF FIRST COMPARISON RESULT IN WHICH SECOND TEST SCORE IS LESS THAN SECOND REFERENCE SCORE AND SECOND COMPARISON RESULT IN WHICH FOURTH TEST SCORE IS LESS THAN FOURTH REFERENCE SCORE IS GENERATED ── S1730-1

EVALUATE THAT THERE IS COGNITIVE FUNCTION DECLINE IN SOCIAL COGNITION ACCORDING TO THIRD COMPARISON RESULT IN WHICH SIXTH TEST SCORE IS LESS THAN SIXTH REFERENCE SCORE AND FOURTH COMPARISON RESULT IN WHICH NINTH TEST SCORE IS LESS THAN NINTH REFERENCE SCORE ── S1730-2

EVALUATE THAT THERE IS COGNITIVE FUNCTION DECLINE IN LANGUAGE ACCORDING TO FIFTH COMPARISON RESULT IN WHICH EIGHTH TEST SCORE IS LESS THAN EIGHTH REFERENCE SCORE IS GENERATED ── S1730-3

EVALUATE THAT THERE IS COGNITIVE FUNCTION DECLINE IN PERCEPTION ACCORDING TO SIXTH COMPARISON RESULT IN WHICH TENTH TEST SCORE IS LESS THAN TENTH REFERENCE SCORE IS GENERATED ── S1730-4

EVALUATE THAT THERE IS COGNITIVE FUNCTION DECLINE IN ATTENTION EXECUTION WHEN AT LEAST ONE OF SEVENTH COMPARISON RESULT IN WHICH FIRST TEST SCORE IS LESS THAN FIRST REFERENCE SCORE, EIGHTH COMPARISON RESULT IN WHICH THIRD TEST SCORE IS LESS THAN THIRD REFERENCE SCORE, NINTH COMPARISON RESULT IN WHICH FIFTH TEST SCORE IS LESS THAN FIFTH REFERENCE SCORE, AND TENTH COMPARISON RESULT IN WHICH SEVENTH TEST SCORE IS LESS THAN SEVENTH REFERENCE SCORE IS GENERATED ── S1730-5

END

TEST METHOD AND APPARATUS FOR EVALUATING COGNITIVE FUNCTION DECLINE

CROSS-REFERENCE TO RELATED APPLICATION

This application is based on and claims priority under 35 U.S.C. § 119 to Korean Patent Application No. 10-2022-0054152, filed on May 2, 2022, and Korean Patent Application No. 10-2023-0054778 filed on Apr. 26, 2023 in the Korean Intellectual Property Office, the disclosure of which is incorporated by reference herein in its entirety.

BACKGROUND

1. Field

The disclosure relates to a test method and apparatus for evaluating a cognitive function decline.

2. Description of the Related Art

As the aging society continues, the number of dementia patients is rapidly increasing. However, there is no cure for dementia. In this regard, the most innovative counterplan for dementia is preventive treatment by detecting, at an early stage, mild cognitive impairment that is highly likely to develop into dementia. The mild cognitive impairment indicates a state of high-risk group in a pre-dementia stage. About 10 to 15% of mild cognitive impairment patients are reported to have dementia.

However, there is no standardized diagnosis method for mild cognitive impairment, and a doctor treats a patient face-to-face and determines the mild cognitive impairment by comprehensively examining a condition of the patient. General tests for evaluating cognitive function decline mainly consist of tests that evaluate memory. Such tests are effective when Alzheimer's disease characterized by memory decline is evaluated, but may have low accuracy when another dementia characterized by cognitive function decline other than memory is evaluated.

The aforementioned background technology is technical information possessed by the inventor for derivation of the disclosure or acquired by the inventor during the derivation of the disclosure, and is not necessarily prior art disclosed to the public before the application of the disclosure.

SUMMARY

One aspect of the disclosure is to provide a user interface that is explicit and easy to understand during a test for evaluating cognitive function decline online.

One aspect of the disclosure is to perform a test by directly involving a user and reduce involvement of a tester, during a test for evaluating cognitive function decline online.

One aspect of the disclosure is to immediately identify a test result after a test for evaluating cognitive function decline online is completed, and enable tracing by identifying a stored past result.

Additional aspects will be set forth in part in the description which follows and, in part, will be apparent from the description, or may be learned by practice of the presented embodiments of the disclosure.

According to an embodiment of the disclosure, a test method for evaluating cognitive function decline is executed by a processor of a test apparatus for evaluating cognitive function decline, and includes performing a testing stage of testing how many missions presented for each of a plurality of test items a user performs, and calculating a test score for each of the plurality of test items, performing a category classifying stage of classifying at least one test item from among the plurality of test items as one neurocognitive category from among a plurality of neurocognitive categories, and performing an evaluating stage of evaluating whether there is cognitive function decline in the one neurocognitive category, based on a test score of the at least one test item classified as the one neurocognitive category.

According to another embodiment of the disclosure, a test apparatus for evaluating cognitive function decline includes a processor, and a memory operatively connected to the processor and storing at least one code performed by the processor, wherein the memory stores at least one code which, when executed through the processor, causes the processor to perform test processes of testing how may missions presented for each of a plurality of test items a user performs, and calculating a test score for each of the plurality of test items, perform a category classification process of classifying at least one test item from among the plurality of test items as one neurocognitive category from among a plurality of neurocognitive categories, and perform an evaluation process of evaluating whether there is cognitive function decline in the one neurocognitive category, based on a test score of the at least one test item classified as the one neurocognitive category.

In addition, provided are another method for implementing the disclosure, another system for implementing the disclosure, and a computer-readable recording medium having stored therein a computer program for executing the method.

Other aspects, features, and advantages may become clear from the following drawings, the claims, and the detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 4, 5A through 5H, 6A through 6H, 7A through 7K, 8A through 8H, 9A through 9O, 10A through 10G, 11A through 11U, 12A through 12N, 13A through 13I, 14A through 14G, 15A through 15J illustrate examples of screens provided on a user terminal to execute a test for evaluating cognitive function decline, according to an embodiment;

FIGS. 17 through 20 are flowcharts of test methods for evaluating cognitive function decline, according to embodiments.

DETAILED DESCRIPTION

Figure 1:
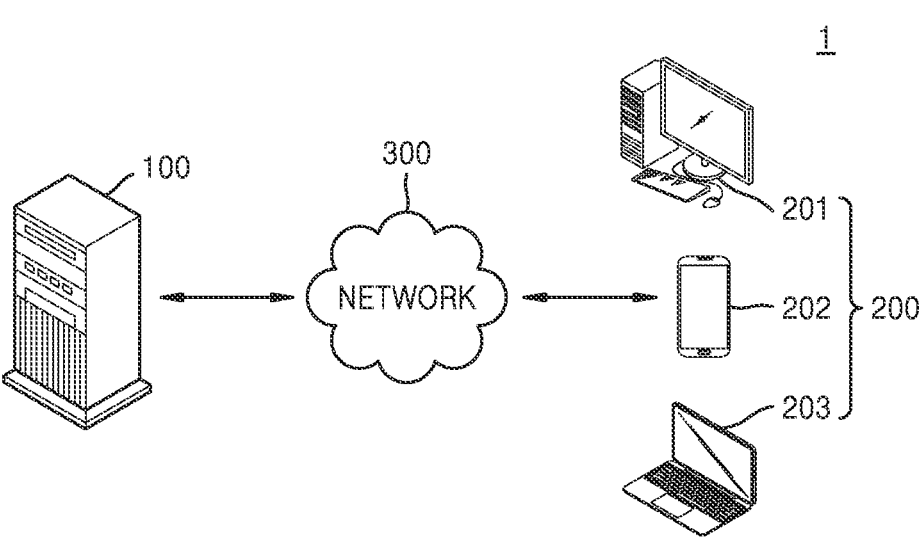
FIG. 1 is a diagram of a test environment for evaluating cognitive function decline, according to an embodiment.

Advantages and features of the disclosure and methods of accomplishing the same may be understood more readily by reference to the following detailed description of the embodiments and the accompanying drawings. However, it should be understood that the disclosure is not limited to the embodiments presented below, but may be implemented in various different forms, and include all transformations, equivalents, and substitutes included in the spirit and scope of the disclosure. The embodiments presented below are provided to complete the disclosure and to fully inform one of ordinary skill in the art of the scope of the disclosure. In the description of the disclosure, certain detailed explanations of related art are omitted when it is deemed that they may unnecessarily obscure the essence of the disclosure.

Also, the terms used in the present specification are only used to describe specific embodiments, and are not intended to limit the disclosure. An expression used in the singular encompasses the expression in the plural, unless it has a clearly different meaning in the context. In the present specification, it is to be understood that terms such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. While such terms as "first", "second", etc., may be used to describe various components, such components are not limited to the above terms. The above terms are used only to distinguish one component from another.

Furthermore, in the specification, the term "unit" or "-or/er" may be a hardware component such as a processor or circuit and/or a software component that is executed by a hardware component such as a processor.

One or more embodiments will be described below in more detail with reference to the accompanying drawings. Those components that are the same or are in correspondence with each other are rendered the same reference numeral regardless of the figure number, and redundant explanations are omitted.

FIG. 1 is a diagram of a test environment 1 for evaluating cognitive function decline, according to an embodiment. Referring to FIG. 1, the test environment 1 for evaluating cognitive function decline may include a test apparatus 100 for evaluating cognitive function decline, a user terminal 200, and a network 300.

The test apparatus 100 may perform test processes of testing how many missions presented for each of a plurality of test items a user performs, and calculating a test score for each of the plurality of test items. In the present embodiment, the test processes may be represented as a testing stage in the claims described below.

In the present embodiment, the test apparatus 100 may perform the test processes including a first test process through an tenth test process.

The first test process may include a process of performing a test for a first test item, in which it is evaluated how many words corresponding to a pre-set presented category are uttered within a pre-set time limit (for example, 30 seconds), and calculating a first test score. Here, the first test item may include a fluency test.

The fluency test may be performed to measure the cognitive flexibility that constitutes executive functioning. The fluency test is a test that evaluates how much cognitive flexibility is naturally calculated within a limited time. The fluency test may include a language fluency test in which a category task and a spelling task are given to produce as many words as possible within a given time, and a visual perceptual fluency test in which shapes are drawn as many as possible by connecting given dots. Language fluency requires both language function and executive Function, and patients with frontotemporal dementia and progressive non-fluent aphasia frequently show significant impairment in both types of language fluency and tasks.

The 1st test process may include a process of performing a test for a 1st test item, in which it is evaluated how many words corresponding to the pre-set presented category are uttered within a first time limit, and calculating a 1st test score. Here, the 1st test item may include a language fluency test. In this regard, the 1st test process may include a process of performing the language fluency test on a user and calculating the 1st test score.

A difference between the fluency test included in the first test process according to the present embodiment and a general fluency test may be as follows. In the general fluency test, a tester writes down words utterred by a user on a test sheet. On the other hand, the fluency test according to the present embodiment uses a speech recognition module (not shown) to record a user's speech, convert the speech into a text in real time, and apply a fluency evaluation model thereto, thereby determining the user's language fluency level. It is possible to prevent a reaction of the user from being inaccurately converted into a text by putting a weight in the process of converting a speech into a text using a speech recognition module. Words to which the user needs to respond will be words corresponding to a certain category, e.g., animals, fruits, and clothes, and any category may be applied as long as the category may include several noun words.

The scoring process and the interpretation of a fluency test included in a first test process are as follows. The number of words answered during a first pre-set time period (e.g., 30 seconds) may be used as a score. Scores may be obtained by counting not only the total number of words uttered during the first pre-set time period but also the number of words answered per second pre-set time period (e.g., 5 seconds or various other time periods). A first weight may be applied to the number of words answered in the first half of the first pre-set time period (e.g., from 0 to 15 seconds), and a second weight may be applied to the number of words answered in the second half of the first pre-set time period (e.g., from 16 to 30 seconds). Here, the first weight may be generated by multiplying the number of answered words by a first value (e.g., 2), wherein the first value is not limited to 2 and may be any number between 1.5 and 2. Also, the second weight may be generated by multiplying the number of answered words by a second value (e.g., 1.5), wherein the first value is not limited to 1.5 and may be any number between 1.5 and 2. The second test process may be performed after the performing of the first test process is completed. The second test process may include a process of performing a test for a second test item, in which words or images are learned while indicating a pre-set category clue and it is evaluated how many learned words or images are recalled after a pre-set time (for example, 20 minutes), and calculating a second test score. Here, the second test item may include a language clue memory test.

Long-term memory, including episodic memory, may be formed through the processes of 1) registration or encoding, 2) storage and retention, and 3) retrieval. Based on detailed and comprehensive evaluation of these three stages, a memory evaluation may determine whether episodic memory is damaged, the extent of the damage, or the characteristics of the damage. By determining whether it is a retrieval failure or a memory strategy problem through the language clue memory test, it is possible to accurately grasp the memory function. Also, the language clue memory test may have diagnostic value in discriminating types of dementia.

In the present embodiment, the second test process may include a (2-1)th test process and a (2-2)th test process.

The (2-1)th test process may include a process of performing a test for a (2-1)th test item, in which it is evaluated how much ability to learn words or images is performed while indicating a pre-set category clue, and calculating a (2-1)th test score. Here, the (2-1)th test item may include a learning test among the language clue memory test. In this regard, the (2-1)th test process may include a process of performing the learning test among the language clue memory test on the user and calculating the (2-1)th test score.

The (2-2)th test process may be performed when a pre-set time has elapsed after the performing of the (2-1)th test process is completed. In the present embodiment, other test processes may be performed from a time when the performing of the (2-1)th test process is completed to the pre-set time. For example, the (2-2)th test process is not performed after the performing of the (2-1)th test process is completed, but the (2-2)th test process may be performed after the performing of the (2-1)th test process is completed and then the third test process is performed.

The (2-2)th test process may include a process of performing a test for a (2-2)th test item, in which it is evaluated how many words or images learned in the (2-1)th test process are recalled after the pre-set time has elapsed, and calculating the (2-2)th test score. Here, the (2-2)th test item may include a recognition test among the language clue memory test. In this regard, the (2-2)th test process may include a process of performing the recognition test among the language clue memory test on the user and calculating the (2-2)th test score.

In the language clue memory test included in the second test process according to the present embodiment, a one-time memory and a long-term memory may be formed through processes of 1) registering or encoding, 2) storing and retaining, and 3) retrieving. Also, memory evaluation, including determination on whether the one-time memory is damaged, and severity or characteristics of the damage, may be performed based on detailed and comprehensive evaluation on these three processes. A memory function may be accurately determined through the language clue memory test according to the present embodiment, and a diagnostic value for evaluating a dementia type may be secured. Here, the accurately determining of the memory function may include determining whether there is a retrieval failure issue or a memory scheme issue.

A difference between the language clue memory test included in the second test process according to the present embodiment and a general language clue memory test may be as follows. The general language clue memory test may be test of instructing a plurality of words and determining how many words are recalled. However, in the language clue memory test according to the present embodiment, a clue indicating a category of a word or an image is provided and learned, and a question is asked while instructing a category of a word even during free recall.

A normal group and mild cognitive impairment, and a normal group and Alzheimer's disease may be evaluated through the language clue memory test included in the second test process according to the present embodiment. The language clue memory test according to the present embodiment may exhibit a significant correlation with gray matter volume of parahippocampus that is an area of a brain related to episodic memory. Thus, the language clue memory test according to the present embodiment may accurately evaluate language memory within a short period of time.

According to the present embodiment, the language clue memory test included in the second test process may be developed into a word interference memory test. The word interference memory test is a language memory test that measures recent memory based on the list-learning paradigm. The list-learning paradigm is a paradigm widely used for the latest memory evaluation and may usually include a procedure for recognizing or recalling a list of words by memorization. In the word interference memory test, first, a first word list (list A, hereinafter referred to as a first list) is presented in half, and then the ability to recognize learned words (maximum learning amount) may be measured. Next, a new word list (list B, hereinafter referred to as a second list) that is semantically related to the first word list (list A) is presented, and the ability to recognize newly learned words (interference suppression) may be measured. When learning and retrieving the second list, the first list learned in the previous step causes semantic interference and affects the performance of the word interference memory test, which may be referred to as proactive semantic interference. It may be understood that the proactive semantic interference occurs due to problems in the process of storage and consolidation of memories, which are the characteristic of Alzheimer's disease, and is known as an important cognitive marker for predicting the Alzheimer's disease of very early stage. The word interference memory test may be configured to sensitively detect memory problems that may appear in early Alzheimer's disease by measuring the maximum amount of learning and the ability to suppress proactive semantic interference and discriminate new information.

The general test LASSI-L (Loewenstein-Acevedo Scales for Semantic Interference and Learning) prompts to recall a total of 15 words that fall into one of three semantic categories. However, the word interference memory test according to the present embodiment reduced the number of words to be memorized to a total of 8 in consideration of the overall educational attainment and daily functional level of the elderly Koreans. Also, the word interference test is composed of familiar and specific words by applying the concept of shopping list and the shopping cart familiar to the elderly Koreans. Furthermore, to facilitate scoring and scoring in a digital environment, a recognition paradigm (a method of determining whether a presented word is a memorized word by looking at the presented word) rather than a recall paradigm (a method of directly recalling and saying words to remember) used in general tests. Also, the word interference test is designed to measure proactive semantic interference even within the recognition paradigm by presenting words included in the first list as non-target words to be excluded when the second list is recognized.

The scoring process and interpretation of the word interference memory test are as follows. First, a recognition score for a first list, the number of true positive responses, and the number of true negative responses may be calculated. Here, according to an embodiment, the recognition score may be calculated by subtracting a reference value (e.g., 4) from the sum of the number of true positive responses and the number of true negative responses. Second, a recognition score for a second list, the number of true positive responses, the number of true negative responses, and the number of false positive errors may be calculated. Third, the total time elapsed for the word interference memory test may be calculated. As a result of scoring the word interference memory test, it may be evaluated that, the higher the recognition score is, the better the latest language memory is. It may be evaluated that, the higher the recognition score for the first list is, the higher the maximum learnable language memory capacity is. It may be evaluated that, the higher the recognition score for the second list is, the better the ability to suppress proactive interference is. It may be interpreted that, the more false positive errors for the second list are, the more vulnerable the subject of the word interference test is to the influence of the proactive semantic interference.

The third test process may be performed after the performing of the (2-1)th test process is completed. The third test process may include a process of executing a test on the third test item for evaluating how accurately and quickly an arbitrary number matched with a presented symbol image is selected within a pre-set time limit (e.g., 45 seconds) by looking at the presented symbol image and calculating the third test score. Here, the third test item may include a symbol number matching test. In this regard, the third test process may include a process of performing the symbol number matching test on the user and calculating the third test score.

Processing speed, which belongs to executive functions, may be evaluated by quickly and accurately scanning visual information, identifying turns, and discriminating them. The symbol number matching test according to the present embodiment may measure visual motor processing speed, short-term visual memory learning ability, cognitive flexibility, attention, concentration, and synchronization. The symbol number matching test is a test in which a symbol is displayed at the center of a screen and it is prompted to find and touch a number connected to the symbol in a number pad at the bottom of the screen. Total n symbols are alternately presented at the center of the screen, and a number presented at the bottom of the screen is connected to one symbol.

A difference between the symbol number matching test included in the third test process according to the present embodiment and a general symbol number writing test may be as follows. The general symbol number writing test is conducted as a paper-pen test for checking a number-symbol connection table in the upper portion of a paper and handwriting a symbol matched with a number in a blank space below the corresponding number in an answer section in the lower portion of the paper. In the symbol number matching test according to the present embodiment, one of symbols in a symbol set is displayed at the center of a screen, and a number matched with the corresponding symbol is to be touched in an answer section therebelow. A symbol set displayed at the center of a screen is generated as follows. A symbol may be generated as a combination of four vertices that may be generated in the shape of a square and all straight lines and curves passing through ½ points between the four vertices. Since a writing tool is used to write an answer in the general symbol number writing test, writing ability may be required. However, the symbol number matching test according to the present embodiment may focus on the function of processing visual information. Symbols used in the symbol number matching test according to the present embodiment may not be languageized in consideration of the copyright of existing symbols, and newly created simple symbols may be applied. In questions in the beginning, symbols may be arranged in an easy difficulty level, such that symbols close to one another are selected. Difficulty may be increased in later questions by arranging symbols, such that all symbols need to be explored.

The scoring process and the interpretation of a symbol number matching test included in a first test process are as follows. The indicators used for scoring may include 1) the number of numbers touched within a given time, 2) the number of touching numbers connected to a symbol displayed at the center of a screen within a given time, 3) the number of touching numbers not connected to the symbol displayed at the center of the screen within a given time, and 4) an average time and a standard deviation taken to touch each number button.

The fourth test process may be performed after the performing of the (2-2)th test process is completed. The fourth test process may include a process of performing a test for a fourth test item, in which a pre-set presented image is learned and it is evaluated how much the learned presented image is recalled after a pre-set time (for example, 20 minutes), and calculating a fourth test score. Here, the fourth test item may include a visual graphic memory test.

The Free and Cued Selective Reminding Test developed by Buschke (1984) is a language memory test that provides categorical cues related to words, creates associations for retrieval in the learning process, and utilizes them for recall. Existing memory tests based on free recall tasks do not distinguish between memory storage failures based on loss of efficiency and memory structure damage due to the use of inefficient strategies and reductions in processing capacity in the memory process. Also, poor performance on the free recall task may not necessarily be a characteristic of dementia, and the same results may be observed due to aging or depression. However, impairment in a cue recall task may be more likely be a characteristic of an early diagnosis of the Alzheimer's disease. In the learning process, which is the encoding stage, a process of categorizing several words into one semantic cluster and promptly recalling the same needs to be included to prevent the degradation of efficiency in the encoding process, thereby detecting the problem of memory degradation due to abnormality in the memory structure. Most of memory tests using such cued recall tasks use word stimuli and semantic cues. However, picture stimuli may evaluate a patient's visual perception ability and are more familiar and more accessible stimuli to the illiterate elderly as compared to word stimuli. In a visual graphic memory test according to the present embodiment, a visual language memory task was constructed by using picture stimuli to increase the efficiency of memory using picture stimuli and graphic cues. As a result of the study, in the visual graphic memory test according to the present embodiment, immediate free recall was a task to clearly distinguish three groups including normal, mild cognitive impairment, and Alzheimer's disease, and the learning task could distinguish the dementia with Lewy bodies from other groups most clearly based on the property of visual recognition. In the visual graphic memory test according to the present embodiment, differences between groups clearly appeared in sub-tests that were significantly affected by encoding rather than memory storage or retention, e.g., learning, immediate cue recall, and immediate free recall.

In the present embodiment, the fourth test process may include a (4-1)th test process and a (4-2)th test process.

The (4-1)th test process may be performed after the performing of the (2-2)th test process is completed. The (4-1)th test process may include a process of performing a test for a (4-1)th test item, in which a pre-set first presented image is shown and visual perception stimulation is input through a process of determining the number of colors in the first presented image, and calculating a (4-1)th test score. Here, the (4-1)th test item may include a learning test among the visual graphic memory test. In this regard, the (4-1)th test process may include a process of performing the learning test among the visual graphic memory test on the user and calculating the (4-1)th test score.

The (4-2)th test process may be performed when a pre-set time has elapsed after the performing of the (4-1)th test process is completed. In the present embodiment, other test processes may be performed from a time when the performing of the (4-1)th test process is completed to the pre-set time. For example, the (4-2)th test process is not performed after the performing of the (4-1)th test process is completed, but the (4-2)th test process may be performed after the fifth test process through the seventh test process are performed.

In the present embodiment, an order of performing the test processes maybe as follows. First, the first test process may be performed, the (2-1)th test process may be performed next, the 3rd test process may be performed next, the (2-2)th test process may be performed next, the fifth test process through the seventh test process may be sequentially performed next, the (4-2)th test process may be performed next, and then the eighth test process through the tenth test process may be sequentially performed next.

In the present embodiment, the (2-2)th test process may be performed after the performing of the 3rd test process is completed, and the (4-2)th test process are performed necessarily after the performing of the seventh test process is completed, but the disclosure is not limited thereto. In other words, the (2-2)th test process and the (4-2)th test process may be performed after performing of one of the third test process through the tenth test process is completed.

The (4-2)th test process may include a process of performing a test for a (4-2)th test item, in which it is evaluated how many presented images learned in the (4-1)th test process are recalled after the pre-set time has elapsed, and calculating a (3-2)th test score. Here, the (4-2)th test item may include a recognition test among the visual graphic memory test. In this regard, the (4-2)th test process may include a process of performing the recognition test among the visual graphic memory test on the user and calculating the (4-2)th test score.

A difference between the visual graphic memory test included in the fourth test process according to the present embodiment and a general visual graphic memory test may be as follows. In the visual graphic memory test according to the present embodiment, interference caused by semantic memory may be excluded by using an abstract image that is unable to be expressed in language. Also, a set of images may be configured by changing a color, a pattern, or an overlapping degree. Also, when performing the recognition test among the visual graphic memory test, an image included in a same set as a learned image may be presented as an interference image. Also, by choosing and presenting an arbitrary image in a set including a same clue, a learning effect of choosing a familiar image according to past tests may be excluded.

The fifth test process may be performed after the performing of the (4-1)th test process is completed. The fifth test process may include a process of performing a test for a fifth test item, in which it is evaluated whether a pre-set presented word and a color of the pre-set presented word are accurately uttered, and calculating a fifth test score. Here, the fifth test item may include a Stroop test.

In the present embodiment, the fourth test process may include a (4-1)th test process and a (4-2)th test process.

The Stroop test may measure the ability to maintaining a goal by suppressing responses unrelated to a goal response. The Stroop test shows a significant difference in test execution ability between dementia patients and normal elderly people, and thus the Stroop test may be an effective indicator for distinguishing between dementia patients and normal elderly people.

The (5-1)th test process may include a process of performing a test for a (5-1)th test item, in which it is evaluated whether a pre-set word is accurately uttered, and calculating a (5-1)th test score. Here, the (5-1)th test item may include a first Stroop test. In this regard, the (5-1)th test process may include a process of performing the first Stroop test on the user and calculating the (5-1)th test score.

The (5-2)th test process may include a process of performing a test for a (5-2)th test item, in which it is evaluated whether a color of a pre-set presented word is accurately uttered, and calculating a (5-2)th test score. Here, the (5-2)th test item may include a second Stroop test. In this regard, the (5-2)th test process may include a process of performing the second Stroop test on the user and calculating the (5-2)th test score.

A difference between the Stroop test included in the fourth test process according to the present embodiment and a general Stroop test may be as follows. In the general Stroop test, a test is performed by using a questionnaire to read provided words continuously, and the number of words that have been accurately read is counted to calculate a test score. However, the Stroop test according to the present embodiment may include a word reading task of choosing a same word as a word indicating a name of a color, and a color reading task of choosing a word matching a color of a word. The Stroop test according to the present embodiment may reduce a performance time considering a time that may show significant test results, and evaluate the number of positive responses during the performance time.

A difference between the line angle perception test included in the fifth test process according to the present embodiment and a general line angle perception test may be as follows. The line angle perception test according to the present embodiment may be a test of finding a choice line corresponding to a presented line by comparing a pair of presented lines with a pre-presented plurality of choice lines. In the line angle perception test according to the present embodiment, a decline level of visuospatial perception may be evaluated while reducing an angle (gradient) difference between the pair of presented lines and the plurality of choice lines.

The sixth test process may be performed after the performing of the fifth test process is completed. The sixth test process may include a process of performing a test for the sixth test item, in which it is evaluated whether a state of emotion appearing in a pre-set face presented image is recognized, and calculating an sixth test score. Here, the sixth test item may include a face emotion test. In this regard, the sixth test process may include a process of performing the face emotion test on the user and calculating the sixth test score.

Generally, a dementia patient may have an emotion recognition disorder due to a change in a cognitive function. Also, the dementia patient may experience a difficulty in exchanging emotions with others compared to normal people, and have a low empathy ability in personal relations. In particular, frontotemporal dementia may exhibit changes in interpersonal behavior, such as insensitivity, a social processing error, and damage to social perception. Compared to a normal group, the frontotemporal dementia may exhibit low face emotion recognition. In this regard, the face emotion test according to the present embodiment may provide a plurality of first face presented images including six basic emotions (joy, fear, sadness, anger, disgust, and surprise), and a plurality of second face presented images that do not include emotions, i.e., emotionless, and determine whether an emotion included in each facial expression is sensitively perceived.

A difference between the face emotion test included in the sixth test process according to the present embodiment and a general face emotion test may be as follows. The general face emotion test was a method of finding an accurate emotion by looking at a photograph of a facial expression. However, the face emotion test according to the present embodiment may present the intensity of emotion in each step and evaluate an emotion that matches. Also, the face emotion test may evaluate the degree of discrimination between a weak emotion and a strong emotion and the difference between a positive emotion and a negative emotion. Also, contrasts calculated from the face emotion test may be useful in differentiating a major depressive disorder and an FTD. In the face emotion test, stimuli may be presented with the ratio of men and women matched to exclude gender bias for stimuli.

The seventh test process may be performed after the performing of the sixth test process is completed. The seventh test process may include a process of executing a test on the seventh test item for evaluating how accurately and quickly a presented number is selected within a pre-set time limit and presenting numbers and days and evaluating how accurately and quickly a day corresponding to a number is selected and calculating a seventh test score. Here, the seventh test item may include a trail making test.

The trail making test may be a test designed to evaluate visual concept and visual motor ability. The trail making test may include a number trail making test and a number-alphabet trail making test. Here, the number-alphabet trail making test is a test of alternately connecting circles with numerical numbers or alphabet letters according to orders thereof. The trail making test may comprehensively require visual perception ability, visual exploration, movement speed, complex visual scanning, and agility. Also, the number-alphabet trail making test may require the ability of converting cognitive functions (e.g., the ability to switch sets), retrograde inhibition, and the ability to maintain two types of parallel thinking.

In the present embodiment, the seventh test process may include a (7-1)th test process and a (7-2)th test process.

The (7-1)th test process may include a process of executing a test on the (7-1)th test item for evaluating how accurately and quickly a random number marked as start is selected within a (7-1)th time limit and how accurately and quickly other presented numbers are selected in descending or ascending order and calculating the (7-1)th test score. Here, the (7-1)th test item may include a number trail making test. In this regard, the (7-1)th test process may include a process of performing the language number trail making test on the user and calculating the (7-1)th test score.

The (7-2)th test process may include a process of executing a test on the (7-2)th test item for presenting numbers and days and evaluating how accurately and quickly a day corresponding to a number is selected within the (7-2)th time limit and calculating the (7-2)th test score. Here, the (7-2)th test item may include a number-day trail making test. In this regard, the (7-2)th test process may include a process of performing the design number-day trail making test on the user and calculating the (7-2)th test score.

Unlike the general trail making test, the trail making test according to the present embodiment is a digital version of a Korean trail making test for the elderly developed by replacing alphabets with familiar days (Mon, Tue, Wed, Thu, Fri, Sat, Sun) in consideration of the characteristics of Korean elderly people.

The eighth test process may be performed after the performing of the (4-2)th test process is completed. The eighth test process may perform a test for a eighth test item, in which it is evaluated whether sizes and weights of pre-set presented objects are arranged in a descending order, and calculate a eighth test score. Here, the eighth test item may include a size weight test.

The size weight test may be a language test for evaluating semantic memory by presenting three animals and three objects and arranging stimuli thereof according to sizes and weights. The size weight test was developed as a Korean version of which animal and object stimuli are modified to be familiar to Korean elderly people and was evaluated whether it could be used appropriately. As a result of the study, the test scores showed a significant difference between a normal group and a Alzheimer's disease (AD) group, allowing the two groups to be discriminated from each other. Also, the test scores showed a significant difference between Alzheimer's disease dementia and semantic primary progressive aphasia (SV-PPA), allowing the two clinical groups to be discriminated from each other. In brain imaging results of SV-PPA patients, a significant correlation was found between the gray matter volume and test scores of the right inferior frontal cortex and bilateral temporal cortices, which is a brain region involved in retrieving semantic information.

In the present embodiment, the eighth test process may include a (8-1)th test process and a (8-2)th test process.

In the (8-1)th test process, a test for a (8-1)th test item, in which it is evaluated whether sizes of pre-set presented objects are arranged in a descending order or an ascending order, may be performed, and a (8-1)th test score may be calculated. Here, the (8-1)th test item may include a size test. In this regard, the (8-1)th test process may include a process of performing the size test on the user and calculating the (8-1)th test score.

In the (8-2)th test process, a test for a (8-2)th test item, in which it is evaluated whether weights of pre-set presented objects are arranged in a descending order or an ascending order, may be performed, and a (8-2)th test score may be calculated. Here, the (8-2)th test item may include a weight test. In this regard, the (8-2)th test process may include a process of performing the weight test on the user and calculating the (8-2)th test score.

A difference between the size weight test included in the eighth test process according to the present embodiment and a general size weight test may be as follows. In the size weight test according to the present embodiment, objects according to sizes and objects according to weights may each be classified according to a plurality of categories (for example, 5), and difficulty levels may be set to low/medium/high by bundles of levels between categories. Combinations of categories, in which a weight difference and a size difference are large, may have low difficulty levels. Combinations of categories, in which a weight difference and a size difference are small, may have high difficulty levels. Also, questions may be easy in the beginning and become difficult towards the end. An image of an object may be configured such that features the object (for example, an animal or a thing) are presented well in a line drawing. Also, an object that is not familiar to aged Korean people may be excluded.

The ninth test process may be performed after the performing of the eighth test process is completed. The ninth test process may include a process of executing a test on a ninth test item for providing an arbitrary image and a narration for the arbitrary image and, after the narration is provided, determining a degree of social situation understanding based on a result of collecting correct responses to questions and calculating a ninth test score. Here, the ninth test item may include a theory of mind test. In this regard, the ninth test process may include a process of performing the theory of mind test on the user and calculating the ninth test score.

Social cognition is the ability to perceive, interpret, and process social information constantly encountered in daily life. The theory of mind refers to the ability to decipher or infer other people's state of mind, such as their beliefs, needs, and intentions, and may enable a person to understand other people and predict their behavior. The theory of mind tests may include a cognitive aspect and an affective aspect. The theory of mind test may be configured to evaluate understanding and handling skills in social situations based on the theory of mind.

A difference between the theory of mind test included in the ninth test process according to the present embodiment and a general theory of mind test may be as follows. The general WAIS-R is a test for checking understanding of social situations by arranging given pictures in order according to the flow of a story. However, it is difficult for the elderly to perform the general WAIS-R due to the difficulty level thereof. Therefore, the theory of mind test according to the present embodiment may be configured as a test in which a story is modified to be elderly-friendly and the intention, the understanding of social situations, and the emotion of a character are asked in contents presented for each scene.

The tenth test process may be performed after the performing of the ninth test process is completed. The tenth test process may include a process of performing a test for a tenth test item, in which it is evaluated whether a figure having a color different from a color of a pre-set presented figure is found, and calculating a tenth test score. Here, the tenth test item may include a color perception test. In this regard, the tenth test process may include a process of performing the color perception test on the user and calculating the tenth test score.

A difference between the color perception test included in the tenth test process according to the present embodiment and a general color perception test may be as follows. The Farnsworth Munsell 100 hue test, as the general color perception test, distinguishes and lists similar colors in four color ranges, based on hue, chroma, and brightness, i.e., three attributes of colors. It is verified whether the user distinguishes differences in colors by arranging an order of colors, based on colors at both ends. On the other hand, in the color perception test according to the present embodiment, colors may be selected and configured based on color systems of green and blue series, considering that dementia patients with Parkinson's disease have difficulty in distinguishing between blue and green. Unlike the general test in which all colors are listed, the color perception test according to the present embodiment may be configured by selecting two colors and setting a difficulty level high when a color difference is small and a difficulty level low when a color difference is large.

After the performing of the first test process through the tenth test process is completed, the test apparatus 100 may a category classification process of classifying at least one test item from among a plurality of test items as one neurocognitive category from among a plurality of neurocognitive categories. The category classification process according to the present embodiment may be represented as a category classifying stage in the claims described below.

The test apparatus 100 may classify the second test item (language clue memory test) and the fourth test item (visual graphic memory test) as a first neurocognitive category for evaluating cognitive function decline regarding memory.

The test apparatus 100 may classify the sixth test item (face emotion test) and ninth test item(theory of mind test) as a second neurocognitive category for determining a neurocognitive disorder regarding social cognition. Here, the second neurocognitive category is newly added to a test for evaluating the cognitive function decline, according to the present embodiment.

The test apparatus 100 may classify the eighth test item (size weight test) as a third neurocognitive category for evaluating cognitive function decline regarding language.

The test apparatus 100 may classify the tenth test item (color perception test) as a fourth neurocognitive category for evaluating cognitive function decline regarding perception.

The test apparatus 100 may classify the first test item (fluency test), the third test item (symbol number matching test), the fourth test item (Stroop test), and the seventh test item (trail making test) as a fifth neurocognitive category for evaluating cognitive function decline regarding attention execution.

After the performing of the category classification process is completed, the test apparatus 100 may perform an evaluation process of evaluating whether there is cognitive function decline in a neurocognitive category, based on a test score of a test item classified as the neurocognitive category. In the present embodiment, the evaluation process may be represented as an evaluating stage in the claims described below.

The test apparatus 100 may perform a first evaluation process of evaluating whether there is cognitive function decline in the first neurocognitive category as the memory, based on the second test score (language clue memory test score) and the fourth test score (visual graphic memory test score).

The test apparatus 100 may perform a second evaluation process of evaluating whether there is cognitive function decline in the second neurocognitive category as the social cognition, based on the sixth test score (face emotion test score) and ninth test score (theory of mind test).

The test apparatus 100 may perform a third evaluation process of evaluating whether there is cognitive function decline in the third neurocognitive category as the language, based on the eighth test score (size weight test score).

The test apparatus 100 may perform a fourth evaluation process of evaluating whether there is cognitive function decline in the fourth neurocognitive category as the perception, based on the tenth test score (color perception test score).

The test apparatus 100 may perform a fifth evaluation process of evaluating whether there is cognitive function decline in the fifth neurocognitive category as the attention execution, based on the first test score (fluency test score), the third test score (symbol number matching test score), the fifth test score (Stroop test score), and the seventh test score (trail making test score).

In the present embodiment, the test apparatus 100 may be present independently in the form of a server, or a test function for evaluating cognitive function decline, provided by the test apparatus 100, may be realized in the form of an application and mounted on the user terminal 200.

The user terminal 200 may receive a test service for evaluating cognitive function decline by accessing a test application for evaluating cognitive function decline and/or a test website for evaluating cognitive function decline, provided by the test apparatus 100. Here, the user terminal 200 may include a terminal possessed by a user to be tested, i.e., a testee.

The user terminal 200 may include a communication terminal for performing functions of a computing device (not shown), and may include, in addition to a desktop computer 201, a smartphone 202, and a laptop computer 203 operated by the user, a tablet personal computer (PC), a smart television (TV), a mobile phone, a personal digital assistant (PDA), a media player, a micro-server, a global positioning system (GPS) device, an electronic book terminal, a digital broadcasting terminal, a navigation device, a kiosk, an MP3 player, a digital camera, a home appliance, and other mobile or non-mobile computing devices, but is not limited thereto. Also, the user terminal 200 may include a wearable device, such as a watch, glasses, a hair band, and a ring, including a communication function and a data processing function. The user terminal 200 is not limited by the above-described details, and a terminal capable of web browsing may be unlimitedly employed. The user terminal 200 may include a microphone for recording the voice of a user, and a GPS sensor for locating the user terminal 200.

The network 300 may connect the test apparatus 100 and the user terminal 200 to each other. Examples of the network 300 include wired networks, such as a local area network (LAN), a wide area network (WAN), a metropolitan area network (MAN), and an integrated service digital network (ISDN), and a wireless network, such as wireless LAN (WLAN), code-division multiple access (CDMA), and satellite communication, but the scope of the disclosure is not limited thereto. Also, the network 300 may transmit/receive information by using short-range communication and/or long-range communication. Here, the short-range communication may include Bluetooth, radio frequency identification (RFID), infrared data association (IrDA), ultra-wideband (UWB), ZigBee, or Wi-Fi technology, and the long-range communication may include code-division multiple access (CDMA), frequency-division multiple access (FDMA), time-division multiple access (TDMA), orthogonal frequency-division multiple access (OFDMA), or single carrier frequency-division multiple access (SC-FDMA) technology.

The network 300 may include a connection of network elements, such as a hub, a bridge, a router, or a switch. The network 300 may include one or more connected networks including a public network, such as the Internet, and a private network, such as a safe corporate private network, for example, a multi-network environment. An access to the network 300 may be provided through one or more wired or wireless access networks.

In addition, the network 300 may support controller area network (CAN) communication, vehicle-to-infrastructure (V2I) communication, vehicle-to-everything (V2X) communication, and wireless access in vehicular environment (WAVE) communication technology, and an Internet of things (IoT) network, in which information is exchanged between distributed components, such as things, and processed, and/or 5th generation (5G) communication.

Figure 2:
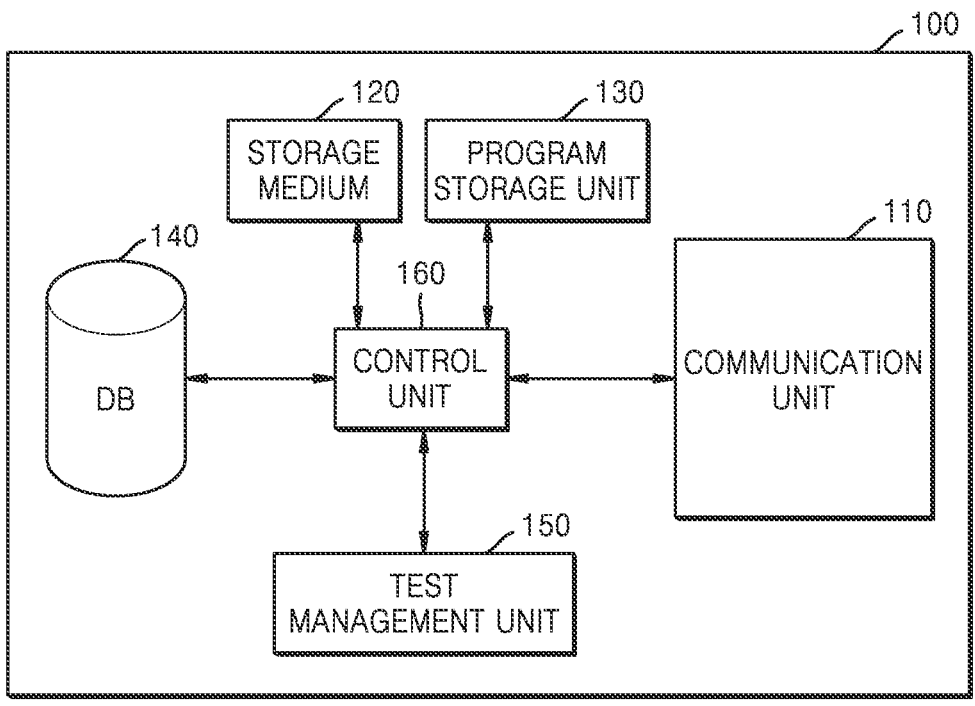
FIG. 2 is a block diagram for schematically describing a configuration of a test apparatus for evaluating cognitive function decline, according to an embodiment.

FIG. 2 is a block diagram for schematically describing a configuration of the test apparatus 100 for evaluating cognitive function decline, according to an embodiment. In the descriptions below, descriptions about details overlapping those of FIG. 1 are omitted. Referring to FIG. 2, the test apparatus 100 may include a communication unit 110, a storage medium 120, a program storage unit 130, a database 140, a test management unit 150, and a control unit 160.

The communication unit 110 may provide a communication interface required to provide, in the form of packet data, a transmission/reception signal between the test apparatus 100 and the user terminal 200, in association with the network 300. In addition, the communication unit 110 may transmit request information of the test management unit 150 to the user terminal 200, and receive response information of the user terminal 200. Here, a communication network is a medium performing a function of connecting the test apparatus 100 and the user terminal 200 to each other, and may include a path that provides an access path for the user terminal 200 to access the test apparatus 100 and then transmit/receive information. Also, the communication unit 110 may be a device including hardware and software required to transmit/receive a signal, such as a control signal or a data signal, through a wired/wireless connection with another network device.

The storage medium 120 performs a function of temporarily or permanently storing data processed by the control unit 160. Here, the storage medium 120 may include a magnetic storage medium or a flash storage medium, but the scope of the disclosure is not limited thereto. The storage medium 120 may include an internal memory and/or an external memory, and may include a volatile memory, such as a dynamic random-access memory (DRAM), a static RAM (SRAM), or a synchronous DRAM (SDRAM), a non-volatile memory, such as a one-time programmable read-only memory (OTPROM), a programmable ROM (PROM), an erasable and programmable ROM (EPROM), an electrically EPROM (EEPROM), a mask ROM, a flash ROM, a NAND flash memory, or a NOR flash memory, a flash drive, such as a solid state drive (SSD), a compact flash (CF) card, a secure digital (SD) card, a micro-SD card, a mini-SD card, an extreme digital (XD) card, or a memory stick, or a storage medium, such as a hard disk drive (HDD).

The program storage unit 130 may be equipped with control software for executing a task of performing the test process of testing how many missions presented for each of a plurality of test items the user performs, and calculating a test score of each of the plurality of test items, a task of performing the category classification process of classifying at least one test item from among the plurality of test items as a neurocognitive category from among a plurality of neurocognitive categories, and a task of performing the evaluation process of evaluating whether there is cognitive function decline in a neurocognitive category, based on a test score of a test item classified as the neurocognitive category.

The database 140 may include a management database storing test information for evaluating cognitive function decline. For example, the management database may store information about the first test process through the tenth test process, information about a first neurocognitive category classification process through a fifth neurocognitive category classification process, information about the first evaluation process through the fifth evaluation process, information about a process of evaluating Alzheimer's disease, information about a process of evaluating frontotemporal dementia, and information about a process of evaluating Parkinson's disease and dementia with Lewy bodies.

Also, the management database may store a correct answer corresponding to an instruction described below. For example, the management database may store a correct text corresponding to a 1st instruction, a correct word or a correct image corresponding to a (2-1)th instruction, a correct word or a correct image corresponding to a (2-2)th instruction, a correct answer corresponding to a 3rd instruction, correct answers corresponding to a (4-1)th instruction and a (4-2)th instruction, a correct answers corresponding to a (5-1)th instruction and (5-2)th instruction, a correct answer corresponding to a sixth instruction, correct answers corresponding to a (7-1)th instruction and a (7-2)th instruction, a correct answer corresponding to a (8-1)th instruction and a (8-2)th instruction, a correct number of word segments corresponding to a ninth instruction, correct answers corresponding to a 10th instruction.

Also, the management database may store a method of calculating a test score. According to the present embodiment, a series of inputs received from the user terminal 200 in response to an instruction may be compared with correct answers, and a test score may be calculated by counting the number of wrong answers compared to all correct answers. Here, the test score may decrease when the number of wrong answers increases, and the test score may increase when the number of wrong answers decreases.

In the present embodiment, a test score may vary depending on a result of counting a spent time described below. For example, the test score may further decrease when the result of counting the spent time exceeds a time limit.

Also, the management database may store a reference score for evaluating cognitive function decline. A process of calculating a reference score may be as follows.

During a first process, the first through tenth test processes may be performed on a normal group. Here, the normal group is a group of normal people without cognitive function decline, and may be differently classified according to gender/education/age. The first through tenth test scores of the normal group may be calculated as results of performing the first through tenth test processes on the normal group.

During a second process, first through tenth average values and first through tenth standard deviations may be calculated for the first through tenth test scores of the normal group.

During a third process, at least one of the first through tenth test items of the normal group may be classified as one of the first neurocognitive category through the fifth neurocognitive category. The second test item and fourth test item of the normal group may be classified as the first neurocognitive category, the sixth test item and ninth test item of the normal group may be classified as the second neurocognitive category, the eighth test item of the normal group may be classified as the third neurocognitive category, the tenth test item of the normal group may be classified as the fourth neurocognitive category, and the first test item, the third test item, the fifth test item, and the seventh test item of the normal group may be classified as the fifth neurocognitive category.

During a fourth process, first through tenth Z-scores may be calculated by using the first through tenth average values and the first through tenth standard deviations for the first through tenth test scores. Here, a Z-score may be a score for determining how far a test score is from an average value in units of standard deviation.

According to the present embodiment, when the Z-score is equal to or less than the first standard deviation (for example, −1.5 SD), it may be evaluated that there is cognitive function decline in a neurocognitive category including a corresponding test item. In this regard, the reference score may be the test score of the normal group, in which the Z-score is the first standard deviation (for example, −1.5 SD). In the present embodiment, the reference score may include a first reference score through an tenth reference score. In the present embodiment, the Z-score may also include the first Z-score through the tenth Z-score.

According to a selective embodiment, the reference score may be represented as a criterion cut-off score. Here, the criterion cut-off score may be the test score of the normal group, in which the Z-score is the first standard deviation (for example, −1.5 SD). In the present embodiment, the criterion cut-off score may include a first criterion cut-off score through an tenth criterion cut-off score.

In the present embodiment, the reference score may be periodically updated. The reference score may be updated in real time whenever the user executes a test application for evaluating cognitive function decline or accesses a test website for evaluating cognitive function decline through the user terminal 200, to perform a test for evaluating cognitive function decline.

Previously, to calculate a reference score, a process of conducting tests on a large number of subjects and collecting result scores takes a lot of manpower and time, and, even when a new result is generated, it takes a long time for the new result to be reflected in the reference score.

On the other hand, according to the present embodiment, since test results collected in real time are stored in the database 140 and a reference score is immediately updated, the latest reference score may always be maintained. Through the real-time reference score update, it is possible to help a user to always get a diagnosis of a cognitive state based on an accurate reference score. Also, since a test process is performed online, it is possible to assist in diagnosis based on the latest reference score without restrictions on the place and the time of the test. Also, the database 140 may store a user database storing information about the user who is to receive a test service for evaluating cognitive function decline. The information about the user may include unique information about the user, including a name, affiliation, personal data, gender, age, education, contact number, email address, address, and image of the user, information about authentication (login) of the user, such as an identification (ID) (or an email address) and a password, and access-related information, such as an access country, an access location, information about a device used for access, and an accessed network environment.

Also, the user database may store the information about the user, information received by the user who accessed the test application for evaluating cognitive function decline or the test website for evaluating cognitive function decline, and/or a category history, information about a configuration set by the user, information about resource usage used by the user, and charging and payment information corresponding to the resource usage of the user.

The test management unit 150 may perform the test processes of testing how many missions presented for each of the plurality of test items the user performs, and calculating the test score for each of the plurality of test items.

The test management unit 150 may perform the category classification process of classifying at least one test item from among the plurality of test items as a neurocognitive category from among the plurality of neurocognitive categories, after the performing of the test processes is completed.

After the performing of the category classification process is completed, the test management unit 150 may perform the evaluation process of evaluating whether there is cognitive function decline in a neurocognitive category, based on a test score of a test item classified as the neurocognitive category.

After the performing of the evaluation process is completed, the test management unit 150 may transmit an evaluation result to the user terminal 200 and/or a terminal (not shown) of a practitioner (for example, a doctor).

The control unit 160 is a type of a central processing unit, and may control all operations of the test apparatus 100 by driving the control software mounted on the program storage unit 130. The control unit 160 may include any type of devices capable of processing data, such as a processor. Here, the "processor" may denote, for example, a data processing device embedded in hardware, which includes a physically structured circuit to perform a function expressed in code or instruction included in a program. Examples of the data processing device embedded in hardware may include processing devices, such as a microprocessor, a central processing unit (CPU), a processor core, a multiprocessor, an application-specific integrated circuit (ASIC), and a field programmable gate array (FPGA), but the scope of the disclosure is not limited thereto.

Figure 3:
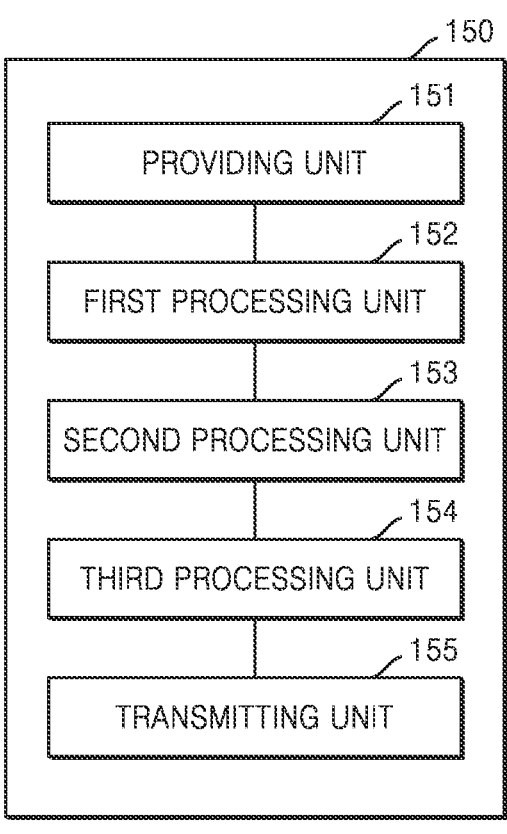
FIG. 3 is a block diagram for schematically describing a configuration of a test management unit in the test apparatus of FIG. 2 for evaluating cognitive function decline.

FIG. 3 is a block diagram for schematically describing a configuration of the test management unit 150 in the test apparatus 100 of FIG. 2 for evaluating cognitive function decline, and FIGS. 4 through 15J illustrate examples of screens provided on the user terminal 200 to execute a test for evaluating cognitive function decline, according to an embodiment. In the descriptions below, descriptions about details overlapping those of FIGS. 1 and 2 are omitted. Referring to FIGS. 3 through 15, the test management unit 150 according to the present embodiment may include a providing unit 151, a first processing unit 152, a second processing unit 153, a third processing unit 154, and a transmitting unit 155.

The providing unit 151 may provide various types of information for a test to the user terminal 200 that accessed the test application for evaluating cognitive function decline and/or the test website for evaluating cognitive function decline. Hereinafter, the diagrams in FIGS. 4 through 15 may be screens output on the user terminal 200 through processing by the providing unit 151.

Figure 4:
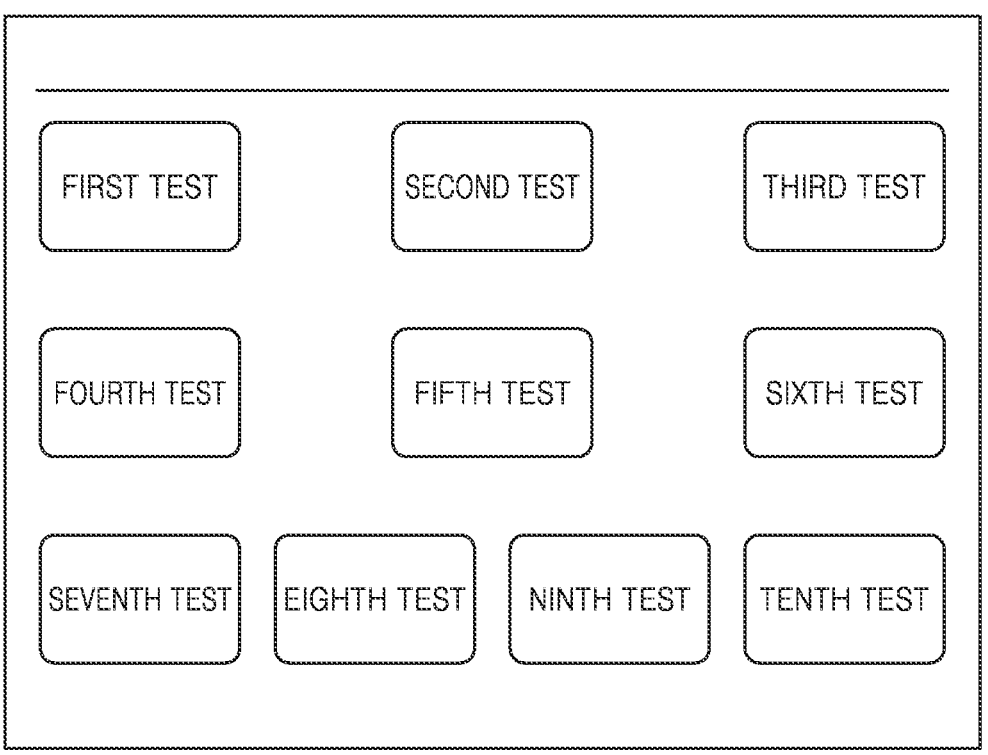

FIG. 4 illustrates an example of a first screen provided to the user terminal 200 by the providing unit 151 so as to perform a test for evaluating cognitive function decline. Referring to FIG. 4, the first screen may include an icon and a text representing a test. According to an embodiment, the providing unit 151 may provide, to the user terminal 200, an icon and a text (first test) indicating a first test, with respect to the first test process. Here, the first test indicated in the text is an abbreviation of the first test process and may be simply and plainly provided considering aged people. In such a manner, the providing unit 151 may provide, to the user terminal 200, icons and texts indicating a second test through an tenth test, with respect to the second test process through the tenth test process.

Pieces of data processed by the first processing unit 152 through the third processing unit 154 may be provided to the user terminal 200 by the providing unit 151. In particular, a series of data provided by the first processing unit 152 is originally provided by the providing unit 151, but for convenience of descriptions, it is assumed that the series of data is provided by the first processing unit 152.

The first processing unit 152 may perform the first test process. According to the present embodiment, the first processing unit 152 may perform the first test process a plurality of times, excluding a practice test.

When the first test process is performed, the first processing unit 152 may provide, to the user terminal 200, the first instruction, in which it is instructed to utter at least one word corresponding to a pre-set presented category within the first time limit.

The first processing unit 152 may receive an utterance result of the at least one word corresponding to the pre-set presented category in response to the first instruction, and convert the utterance result into an utterance text.

The first processing unit 152 may calculate the first test score by comparing the utterance text with a correct text. According to the present embodiment, the first test score may be calculated to be high when there are many utterance texts determined to be correct answers compared to the total number of times the first test processes have been performed.

According to the present embodiment, before the (1-1)th test process is performed, the first processing unit 152 may provide, in at least one of a text and an instruction screen, a method of performing the (1-1)th test process to the user terminal 200, and perform a practice test for the (1-1)th test process.

According to the present embodiment, it may be evaluated that fluency is good when the first test score is higher than the first criterion cut-off score, and is declined when the first test score is lower than the first criterion cut-off score.

FIGS. 5A through 5H illustrate examples of screens provided to the user terminal 200 to perform the first test process. In the present embodiment, FIGS. 5A through 5H illustrate examples of screens for describing the first test process.

Figure 5A:
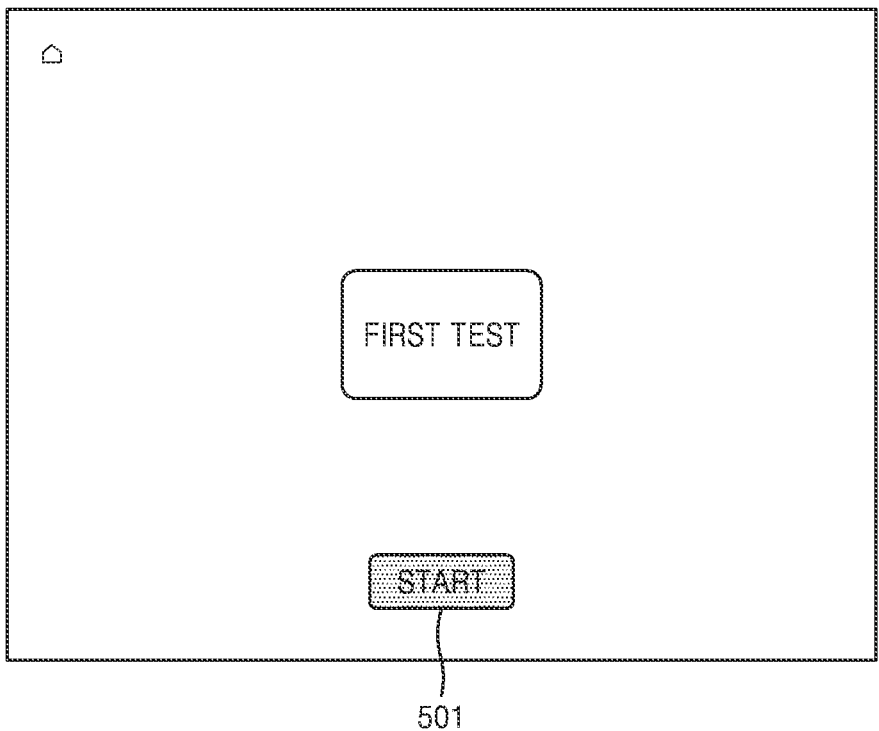

FIG. 5A illustrates a start screen of the first test process. When an input of a start button 501 is received, a next screen may be displayed.

Figure 5B:
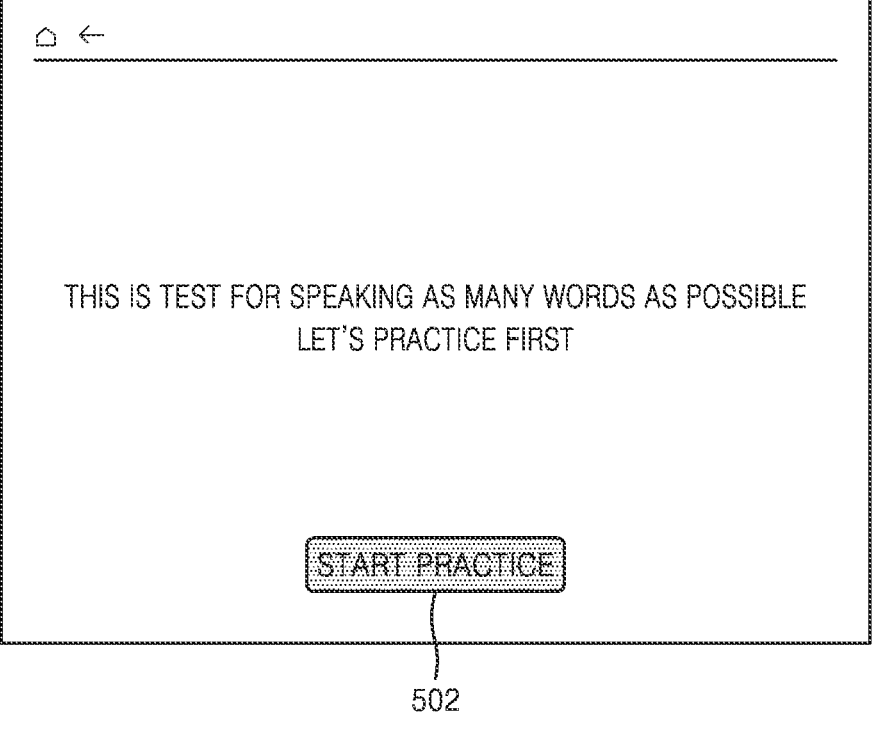

FIG. 5B illustrates a screen in which a method of performing the first test process is provided in a text and a start of a practice test process (first practice test process) for the first test process is notified. When a practice start button 502 is input, a next screen may be displayed.

Figure 5C:
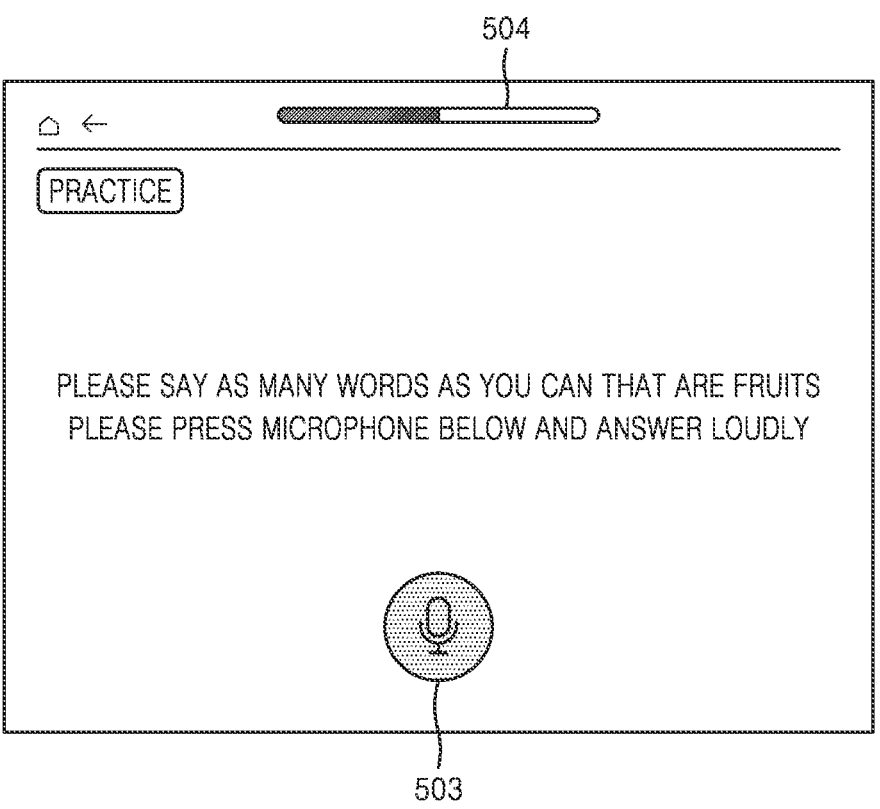

FIG. 5C illustrates a screen for performing the first practice test process. The user may check a first practice instruction, input a microphone button 503, and utter words while looking at a progress bar 504. In the present embodiment, the progress bar 504 may perform at least one of a function of counting a time limit and a function of illustrating a work progress degree.

Figure 5D:
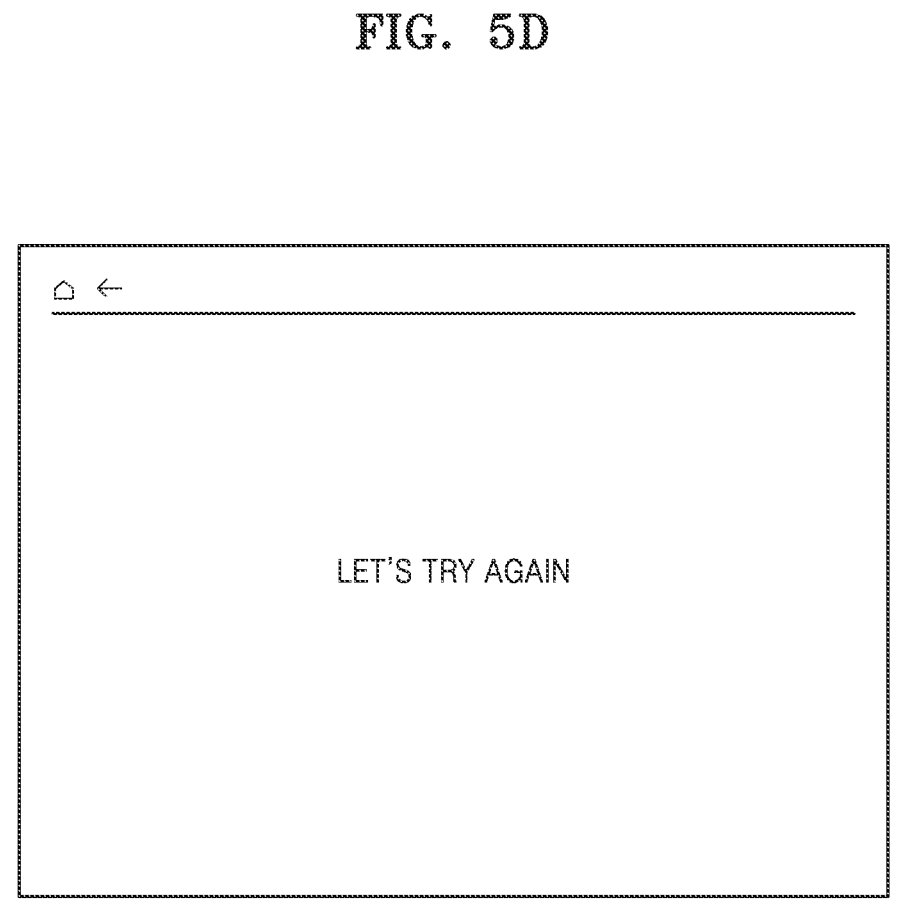

FIG. 5D illustrates a screen indicating a rerun of the first practice test process. The first practice test process may be rerun when the user has not input the microphone button 503, the number of uttered words is less than a pre-set number (for example, 3), or uttered voice volume is low.

Figure 5E:
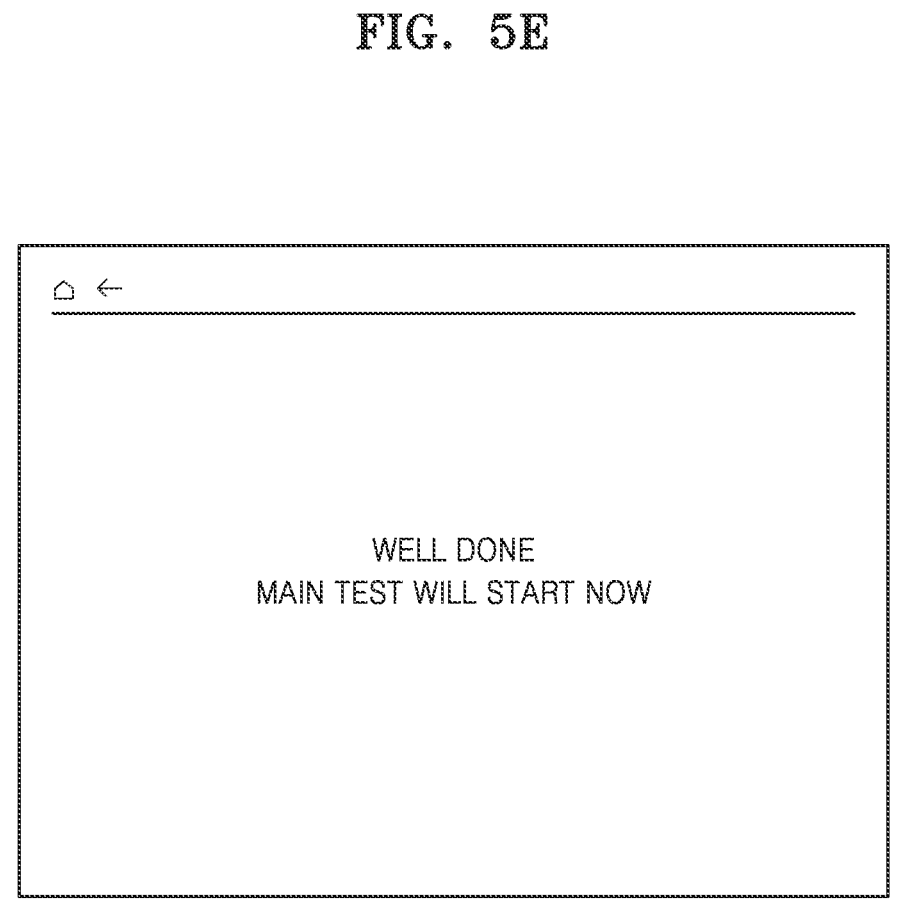

FIG. 5E illustrates a screen indicating completion of the performing of the first practice test process, and performing of a main test.

Figure 5F:
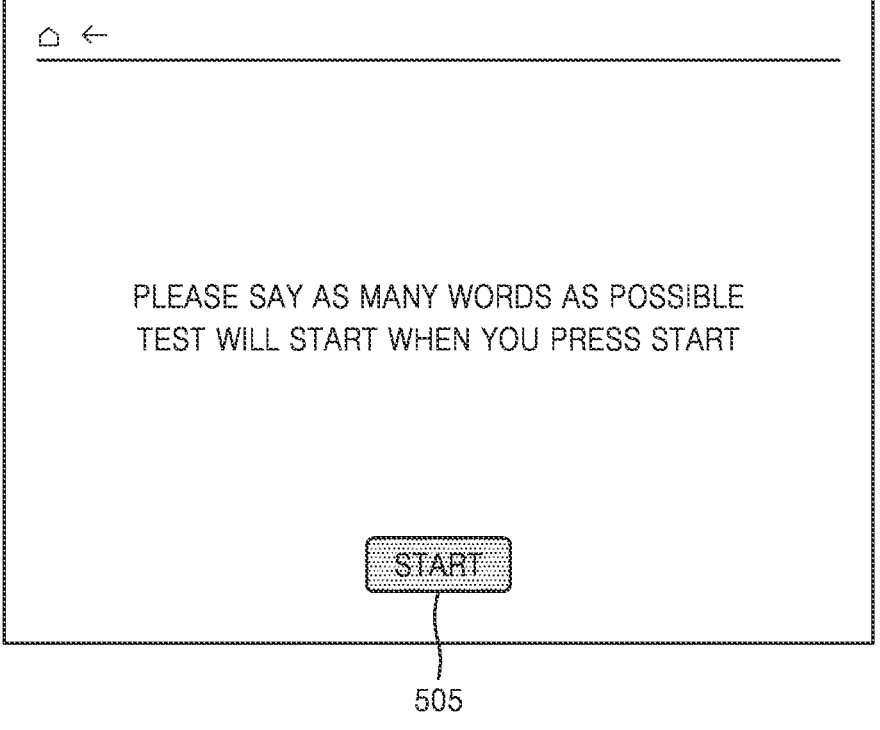

FIG. 5F illustrates a screen indicating the first instruction and a start of the first test process. When a start button 505 is input, a next screen may be displayed.

Figure 5G:
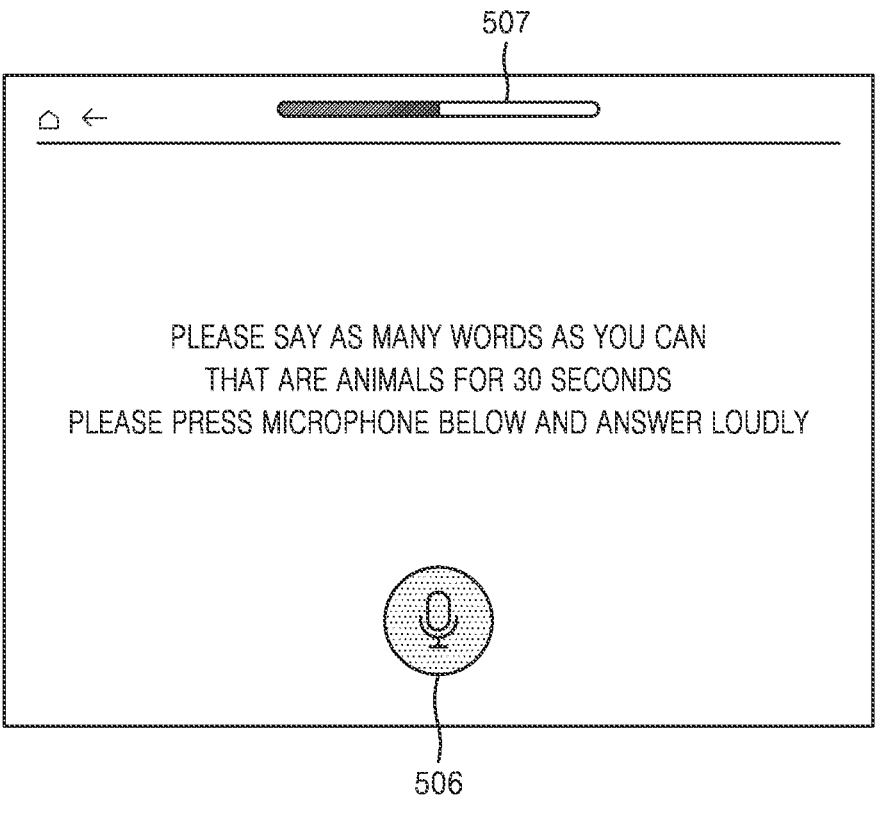

FIG. 5G illustrates a screen for performing the first test process. The user may check the first instruction, input a microphone button 506, and utter words while looking at a progress bar 507, in response to the first instruction. The recorded voice may be transmitted from the user terminal 200 to the test apparatus 100. The control unit 160 of the test apparatus 100 may convert the voice data to a text using a speech recognition algorithm and count the number of words included in the text.

Figure 5H:
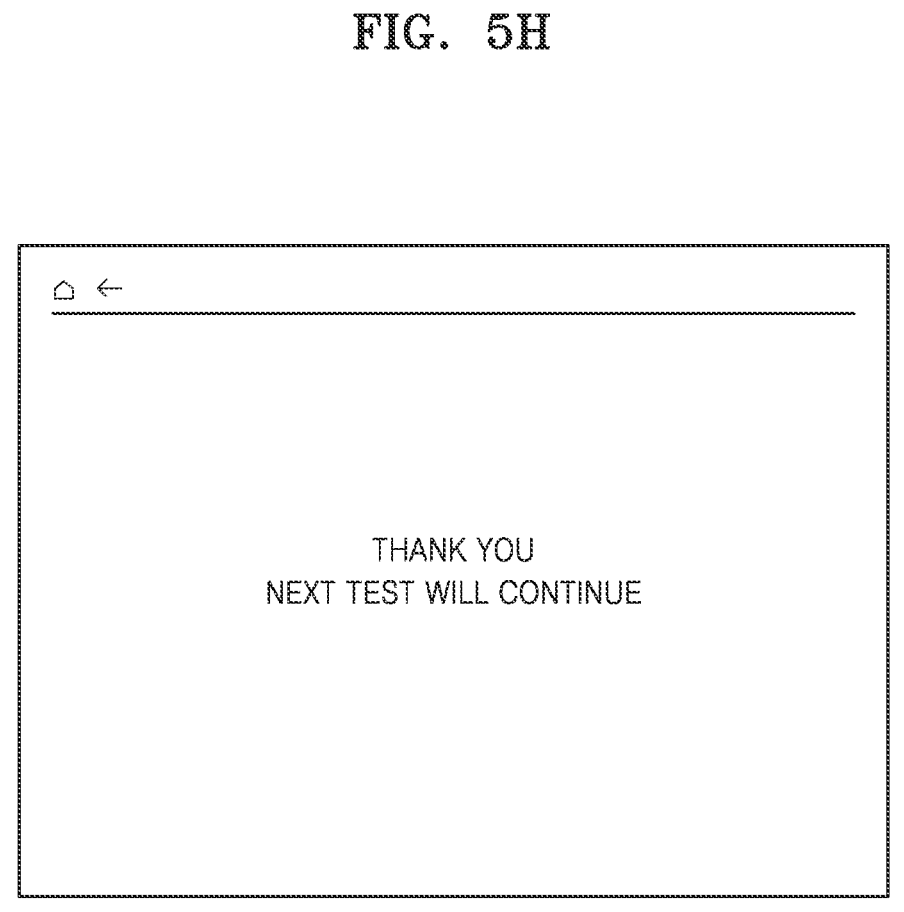

FIG. 5H illustrates a screen indicating completion of the performing of the first test process and a start of a next test process.

When the (2-1)th test process is performed, the first processing unit 152 displays a plurality of presented words or a plurality of presented images and may provide a (2-1)th instruction to choose a word or a image corresponding to a pre-set category clue from among the plurality of presented words or the plurality of presented images to the user terminal 200.

The first processing unit 152 may receive, from the user terminal 200, a word or image choice result of choosing one word or image from among the plurality of presented words or the plurality of presented images in response to the (2-1)th instruction.

The first processing unit 152 may calculate the (2-1)th test score by comparing a word or picture choice result with a correct word or a correct image. According to the present embodiment, the (2-1)th test score may be calculated to be high when there are many word choice results determined to be correct answers compared to the total number of times (2-1)th test processes have been performed.

According to the present embodiment, before the (2-1)th test process is performed, the first processing unit 152 may provide, in at least one of a text and an instruction screen, a method of performing the (2-1)th test process to the user terminal 200.

The first processing unit 152 may perform the (2-2)th test process when a pre-set time has elapsed after the performing of the (2-1)th test process is completed.

When the (2-2)th test process is performed, the first processing unit 152 may provide a (2-2)th instruction prompting to choose whether a pre-set presented word or a pre-set presented picture is a word or a picture seen in a previous test to the user terminal 200, together with the pre-set presented word or the pre-set presented picture.

In response to the (2-2)th instruction, the first processing unit 152 may compare a result of choosing whether the pre-set presented word or the pre-set presented picture is a word or a picture seen in a previous test with a correct word or a correct picture and calculate a (2-2)th test score. According to the present embodiment, the (2-2)th test score may be calculated to be high when there are many results determined to be correct answers compared to the total number of times the (2-2)th test processes have been performed.

According to the present embodiment, before the (2-2)th test process is performed, the first processing unit 152 may provide, in at least one of a text and an instruction screen, a method of performing the (2-2)th test process to the user terminal 200.

According to a selective embodiment, the first processing unit 152 may calculate the second test score by adding at least one of the (2-1)th test score and the (2-2)th test score. Alternatively, the first processing unit 152 may use each of the (2-1)th test score and the (2-2)th test score to evaluate cognitive function decline, without adding the (2-1)th test score and the (2-2)th test score. According to the present embodiment, it may be evaluated that language memory is good when the second test score is higher than the second criterion cut-off score, and is declined when the second test score is lower than the second criterion cut-off score.

FIGS. 6A through 6H illustrate examples of screens provided to the user terminal 200 to perform the second test process. FIGS. 6A through 6D illustrate examples of screens for describing the (2-1)th test process and FIGS. 6E through 6H illustrate examples of screens for describing the (2-2)th test process. For convenience of explanation, the second test process according to the present embodiment is described by using words as an example, and pictures may be included instead of words.

Figure 6A:
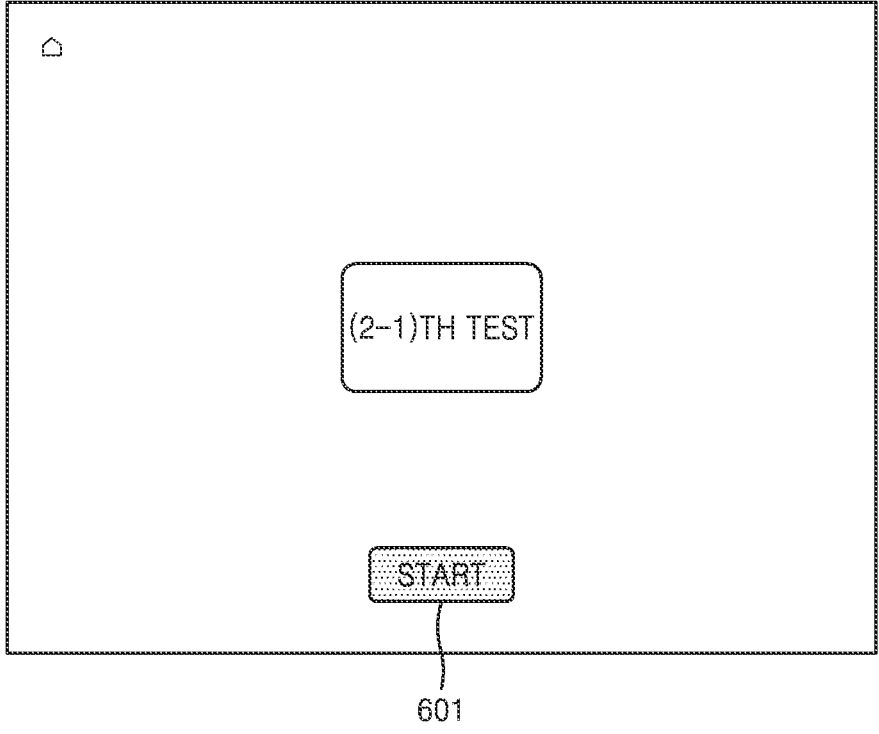

FIG. 6A illustrates a start screen of the (2-1)th test process. When an input of a start button 601 is received, a next screen may be displayed.

Figure 6B:

FIG. 6B illustrates a screen providing, in a text, a method of performing the (2-1)th test process, and indicating a start of the (2-1)th test process. When a start button 602 is input, a next screen may be displayed.

Figure 6C:
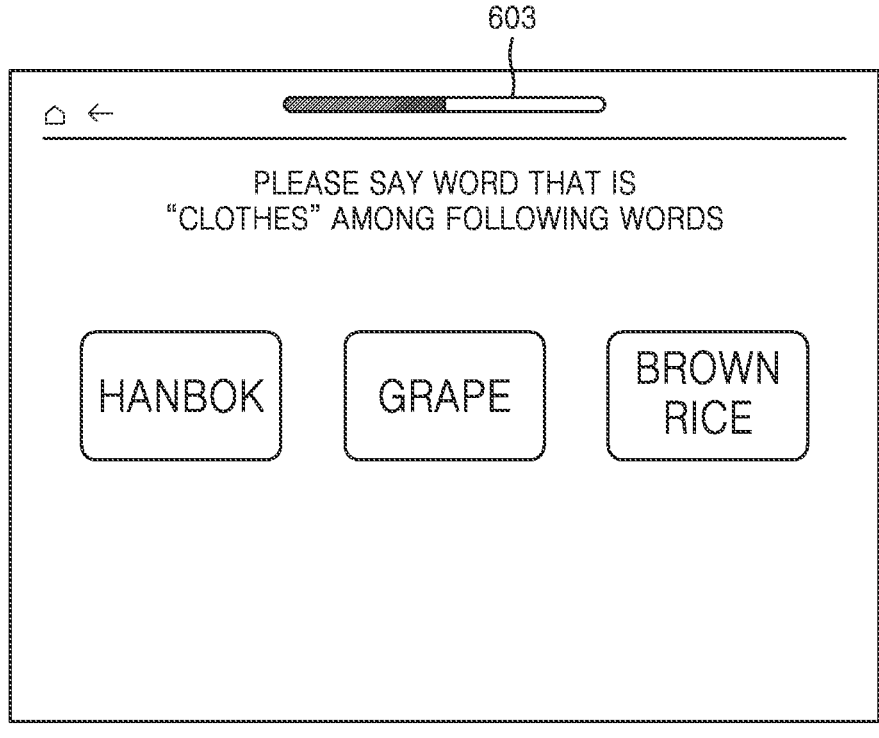

FIG. 6C illustrates a screen for performing a part of the (2-1)th test process. The user may check the (2-1-1)th instruction, and then choose a word from among a plurality of presented words while looking at a progress bar 603.

Figure 6D:
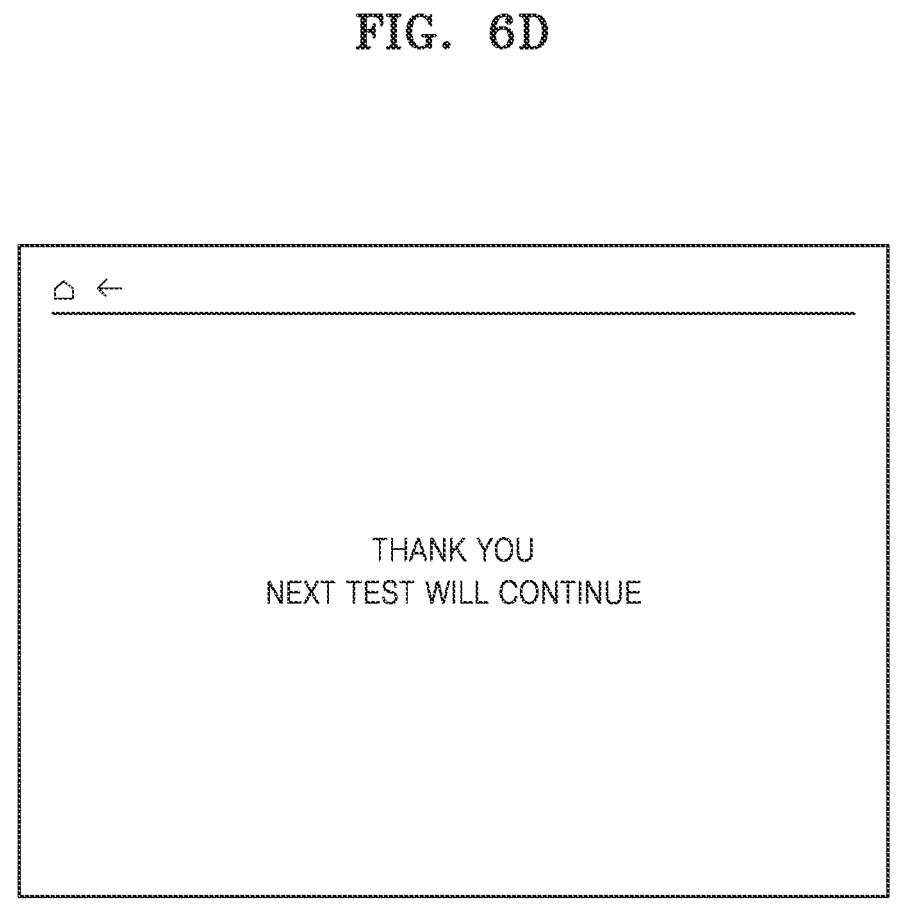

FIG. 6D illustrates a screen indicating completion of the performing of the (2-1)th test process and a start of a next test process.

Figure 6E:
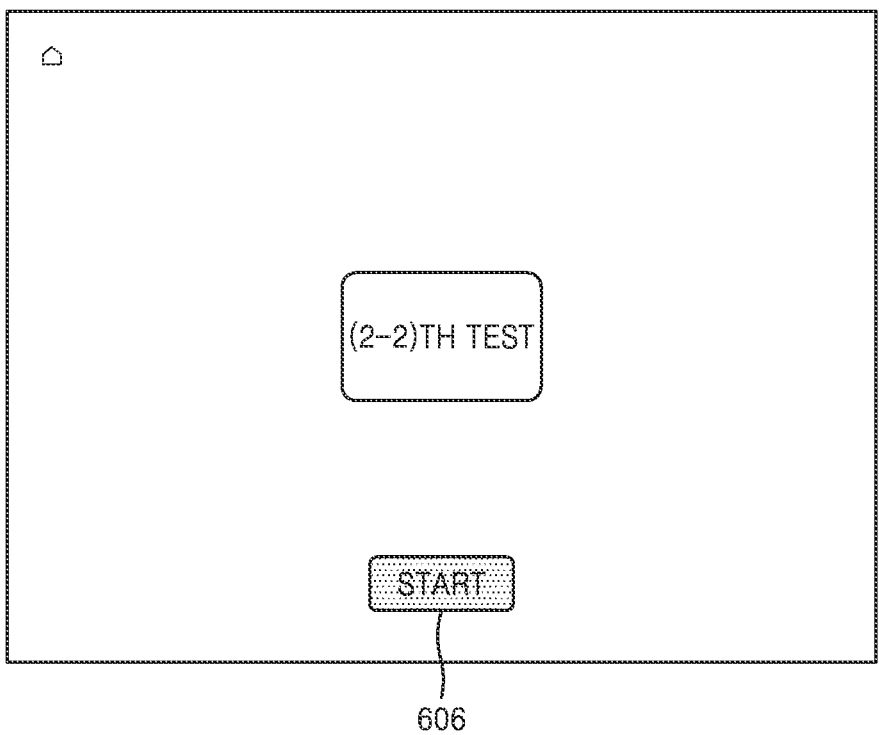

FIG. 6E illustrates a start screen of the (2-2)th test process. When an input of a start button 606 is received, a next screen may be displayed. Here, the start screen of the (2-2)th test process may be provided to the user terminal 200 after the performing of the seventh test process is completed.

Figure 6F:
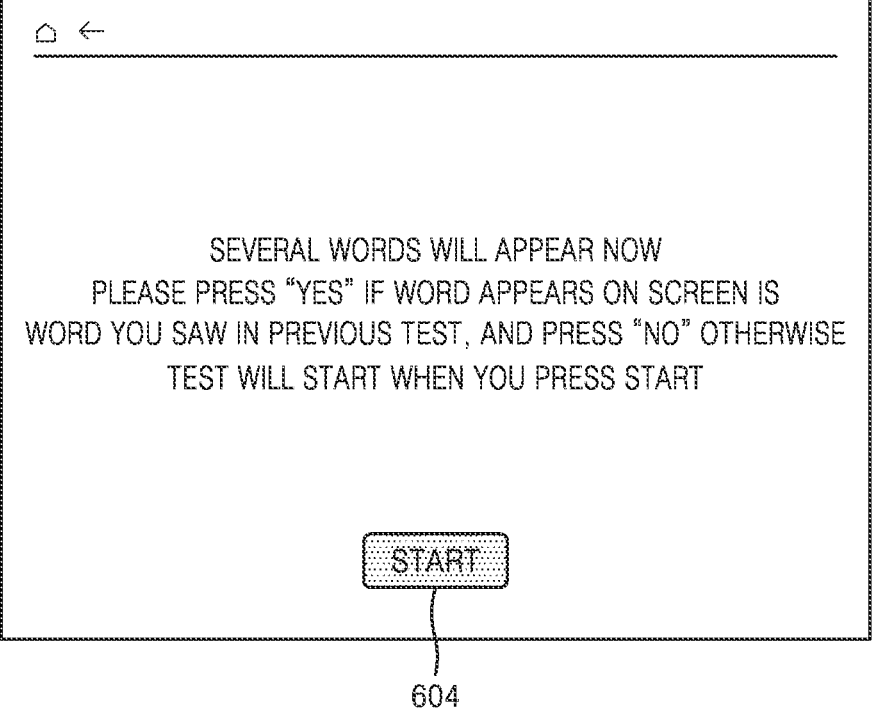

FIG. 6F illustrates a screen providing, in a text, a method of performing the (2-2)th test process, and indicating a start of the (2-2)th test process. When a start button 604 is input, a next screen may be displayed.

Figure 6G:
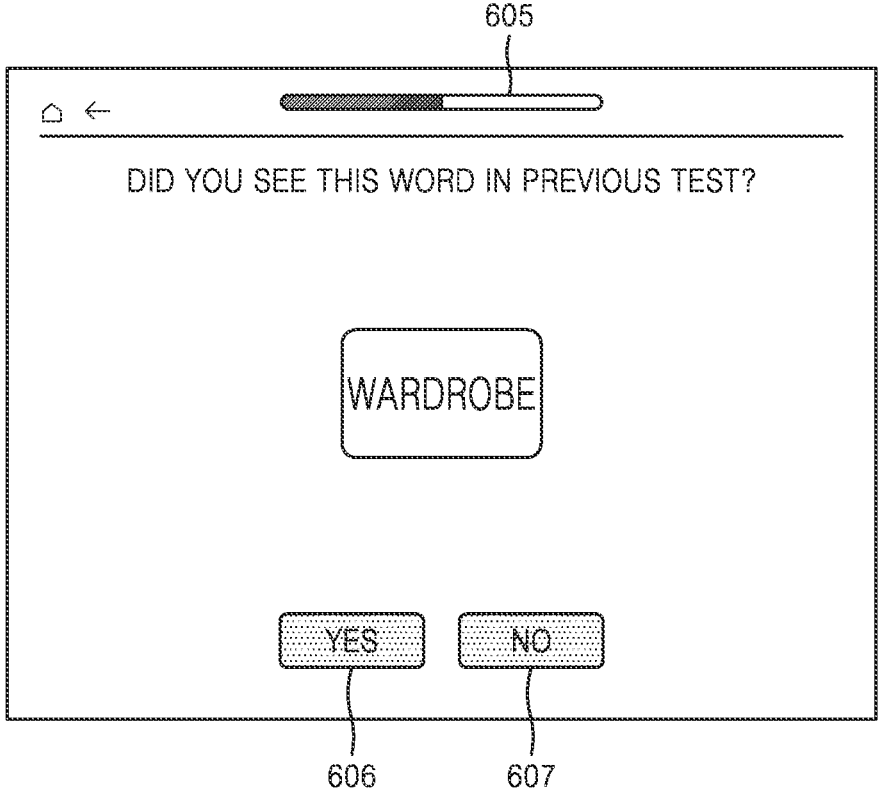

FIG. 6G illustrates a screen for performing the (2-2)th test process. The user may check the (2-2)th instruction and choose one of a Yes button 606 and a No button 607 while looking at a progress bar 612.

Figure 6H:
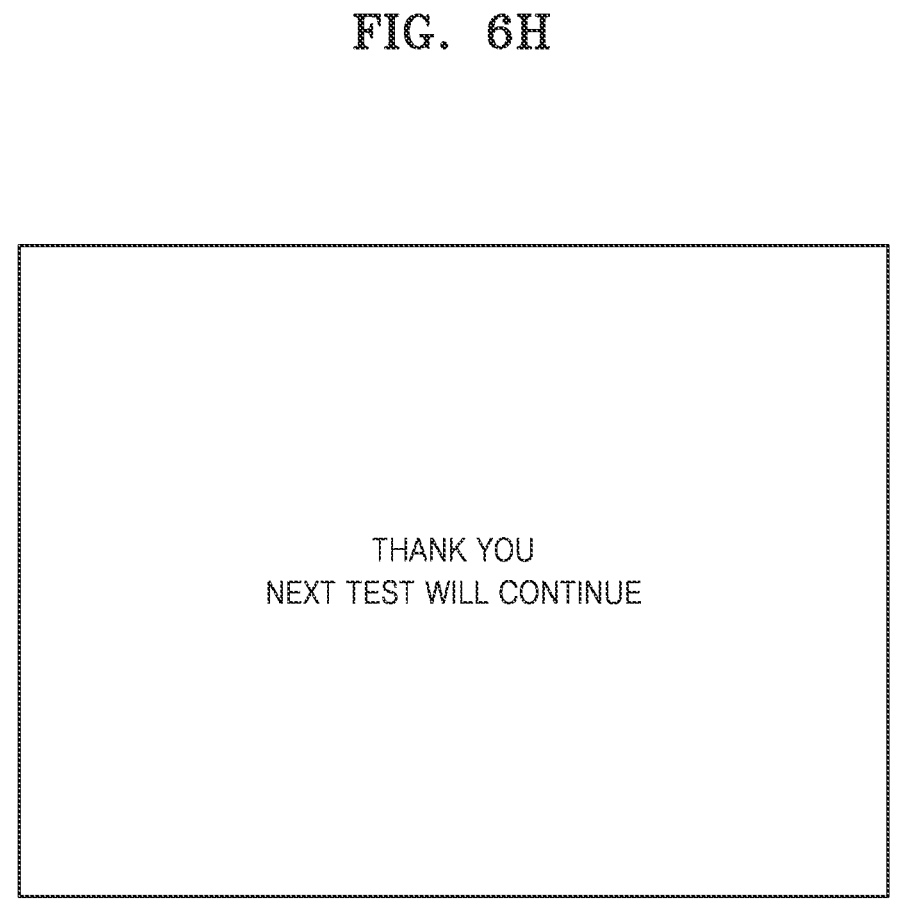

FIG. 6H illustrates a screen indicating completion of the performing of the (2-2)th test process and a start of a next test process.

Referring back to FIG. 3, the first processing unit 152 may perform the third test process including the third test process. According to the present embodiment, the first processing unit 152 may perform the third test process a plurality of times, excluding a practice test.

When the third test process is performed, the first processing unit 152 may display an arbitrary symbol image in the center of a screen and provide a third instruction to choose an arbitrary number matched with an image identical to the arbitrary symbol image within a third time limit to the user terminal 200.

The first processing unit 152 may receive a choice result for the arbitrary number matched with the image identical to the arbitrary symbol image in response to the third instruction from the user terminal 200 and calculate a third test score by comparing the choice result with a correct answer. In the present embodiment, the larger the number of choice results determined as correct answers, the higher the third test score may be.

According to the present embodiment, before the third test process is performed, the first processing unit 152 may provide, in at least one of a text and an instruction screen, a method of performing the third test process to the user terminal 200, and perform a practice test for the third test process.

According to the present embodiment, it may be evaluated that an executive function is good when the third test score is higher than the third criterion cut-off score, and is declined when the third test score is lower than the third criterion cut-off score.

FIGS. 7A through 7K illustrate examples of screens provided to the user terminal 200 to perform the third test process.

Figure 7A:
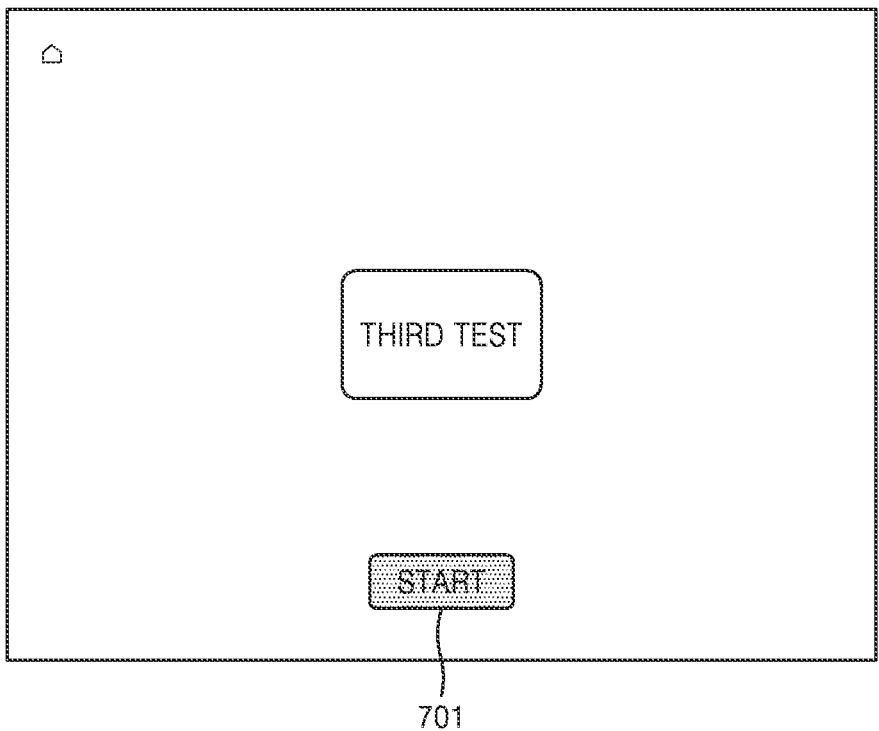

FIG. 7A illustrates a start screen of the fifth test process. When an input of the start button 701 is received, a next screen may be displayed and an instruction screen may be displayed.

Figure 7B:
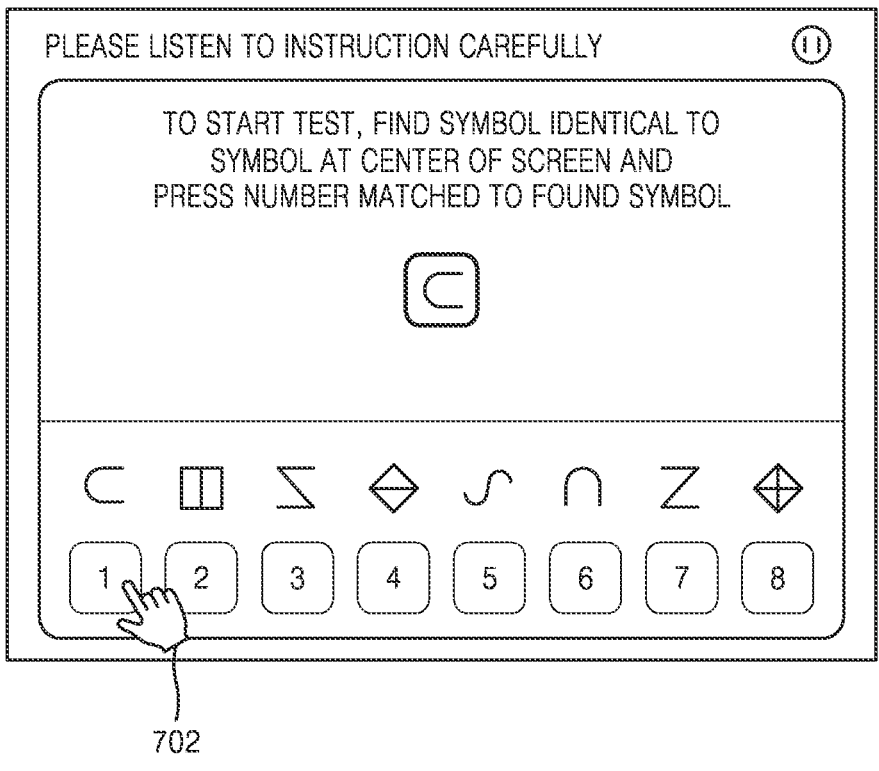
Figure 7C:
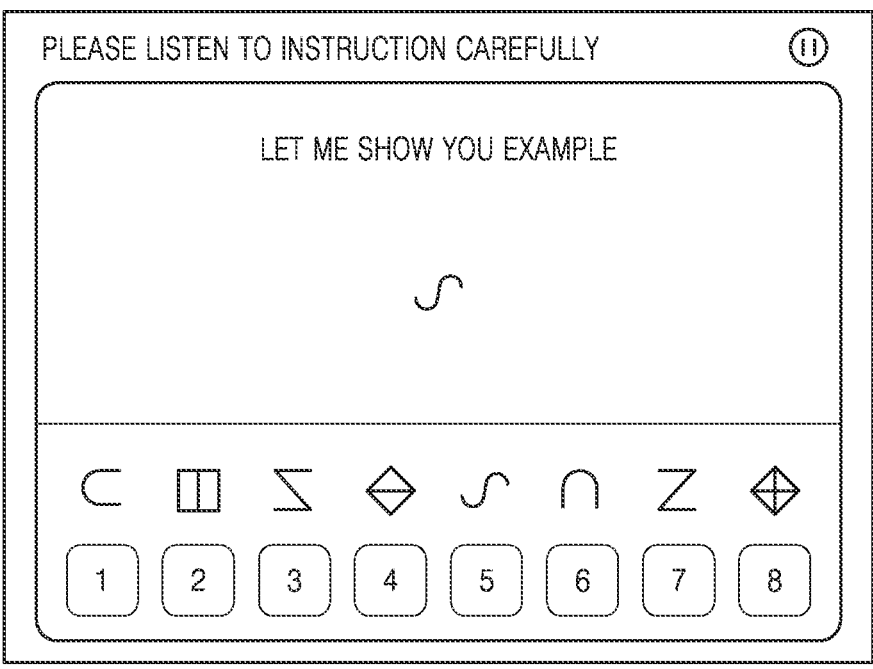
Figure 7D:
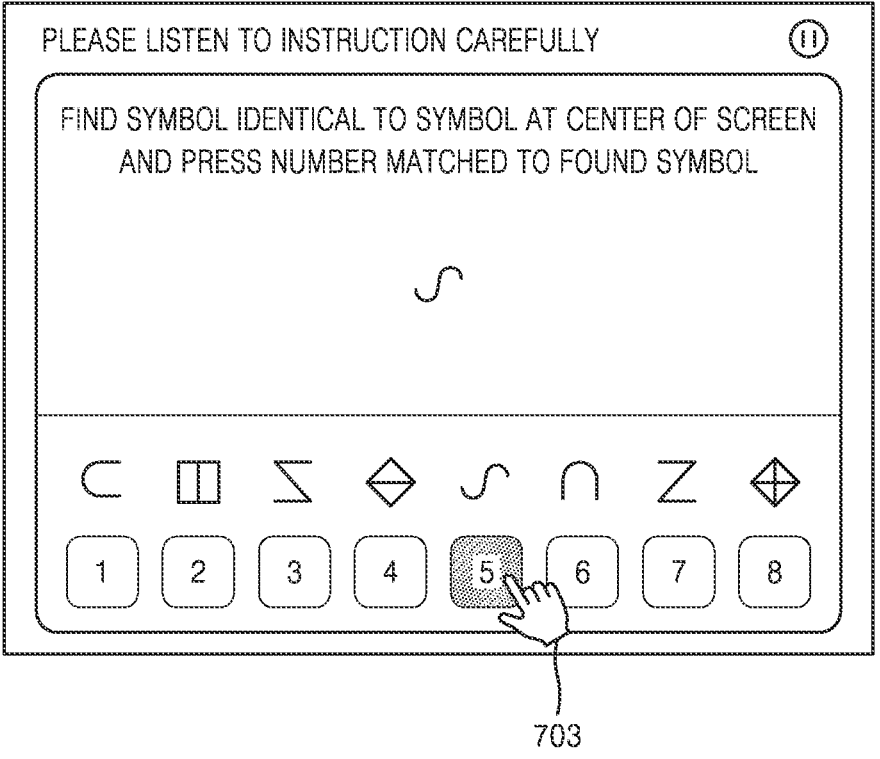

FIGS. 7B to 7D illustrate instruction screens for the third test process. FIGS. 7B to 7D may be displayed all at once or sequentially, and may be switched to a next screen when a predetermined time is elapsed. FIG. 7B illustrates that a symbol image is displayed in the center of a screen and a hand image 702 moves according to an instruction and selects the number 1. In FIG. 7C, another symbol image is displayed in the center of the screen. FIG. 7D illustrates that a hand image 703 moves according to an instruction and selects the number 5.

Figure 7E:
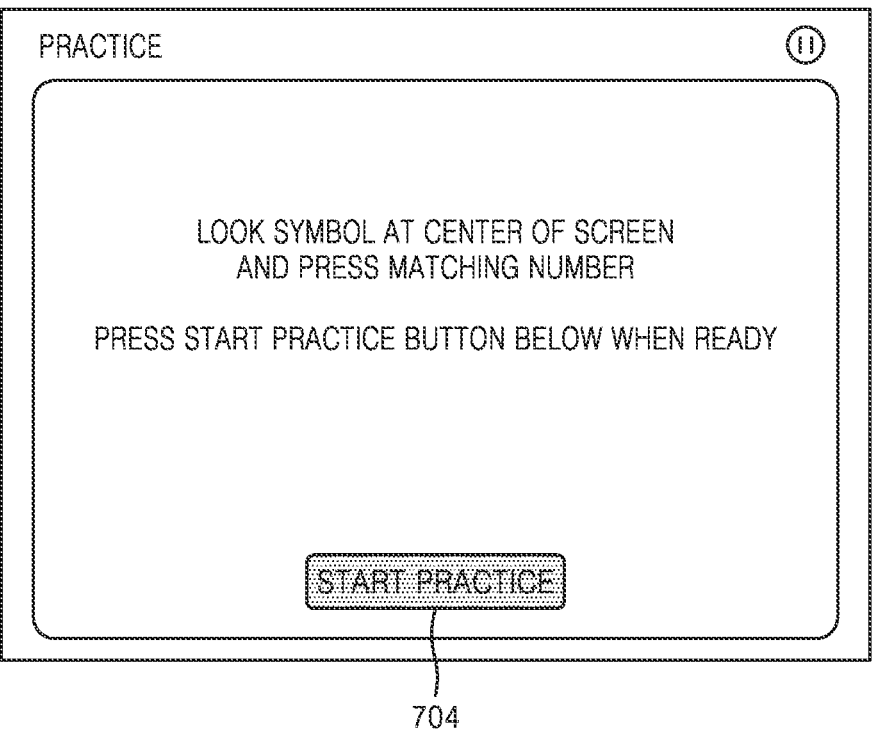

FIG. 7E illustrates a screen indicating a start of a practice test process (third practice test process) for the third test process. When a practice start button 704 is input, a next screen may be displayed.

Figure 7F:
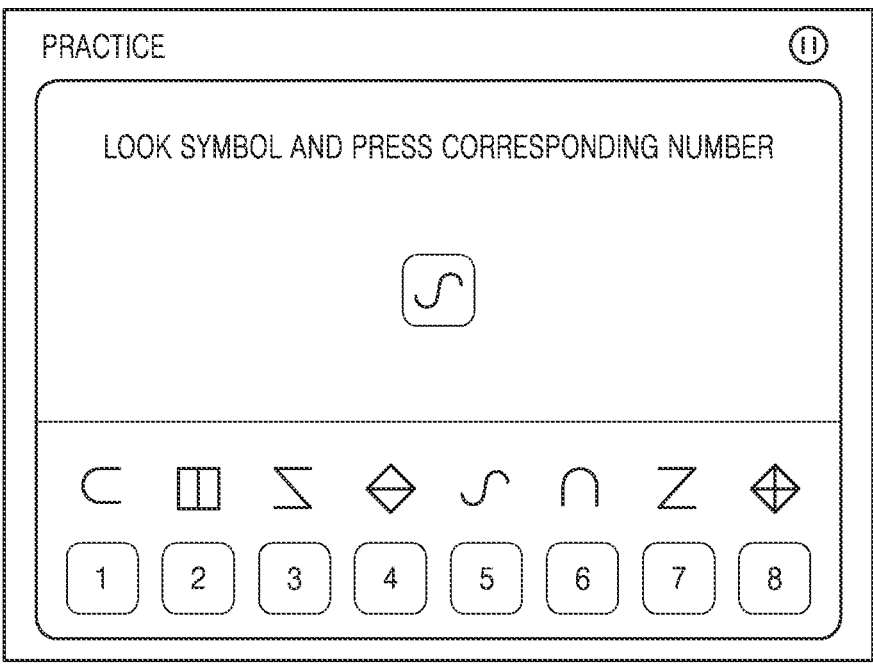

FIG. 7F illustrates a screen for performing the third practice test process. The screen of FIG. 7F may include a third practice instruction, a symbol image displayed in the center of the screen, a plurality of symbol images displayed at the bottom of the screen, and a plurality of numbers respectively matched with the plurality of symbol images. A user may check the third practice instruction, search for a symbol image most similar to the symbol image displayed in the center of the screen, and choose a number matched with a found symbol image. In FIG. 7F, the symbol image displayed in the center of the screen and the plurality of symbol images displayed at the bottom of the screen may not respond to a touch. In FIG. 7F, the plurality of numbers respectively matched with the plurality of symbol images may respond to a touch.

Figure 7G:
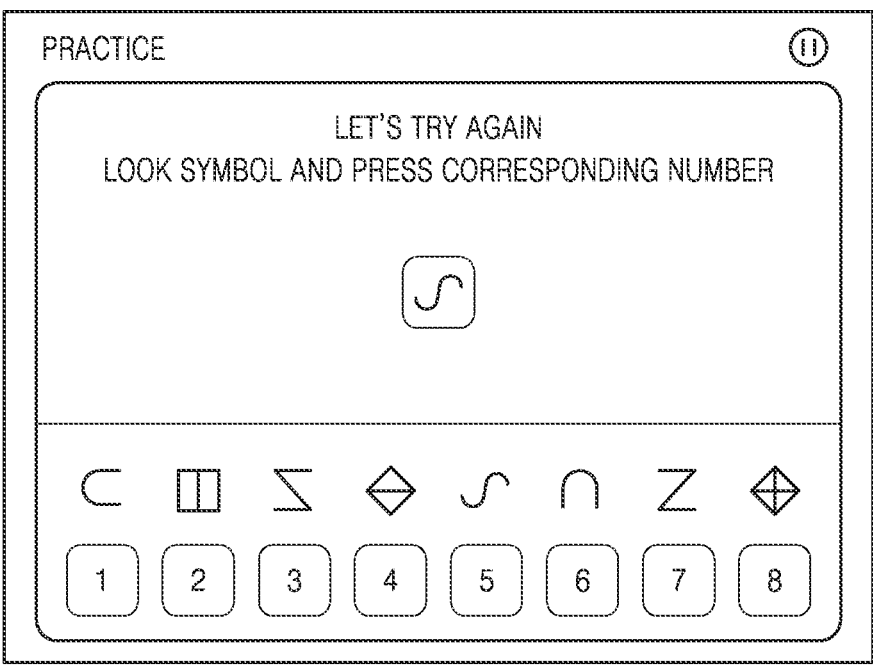
Figure 7H:
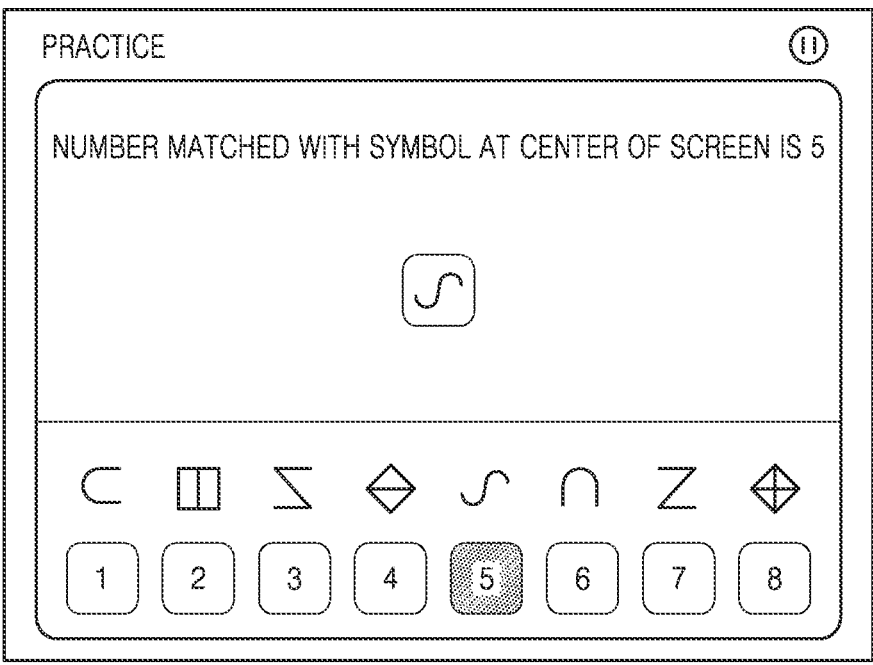

FIG. 7G shows a screen provided when an incorrect practice answer is given, and FIG. 7H illustrates a screen provided when consecutive incorrect practice answers are given. In FIGS. 7G and 7H, an instruction to choose a number corresponding to a symbol image again may be displayed.

Figure 7I:
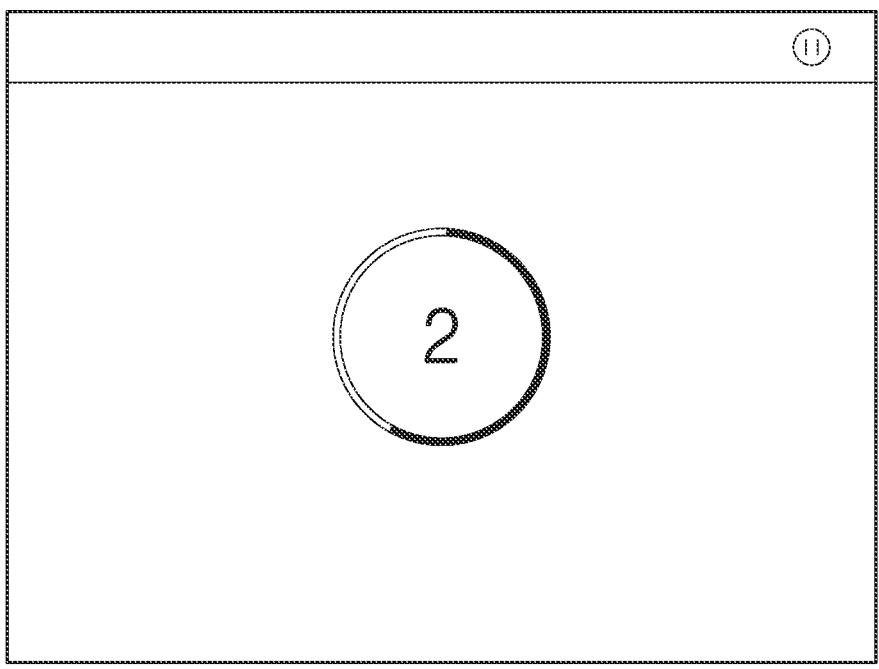

FIG. 7I illustrates a countdown for terminating the third practice test process and executing the third test process. In FIG. 7I, counts 3, 2, and 1 and a start screen may be displayed before the third test process starts.

Figure 7J:
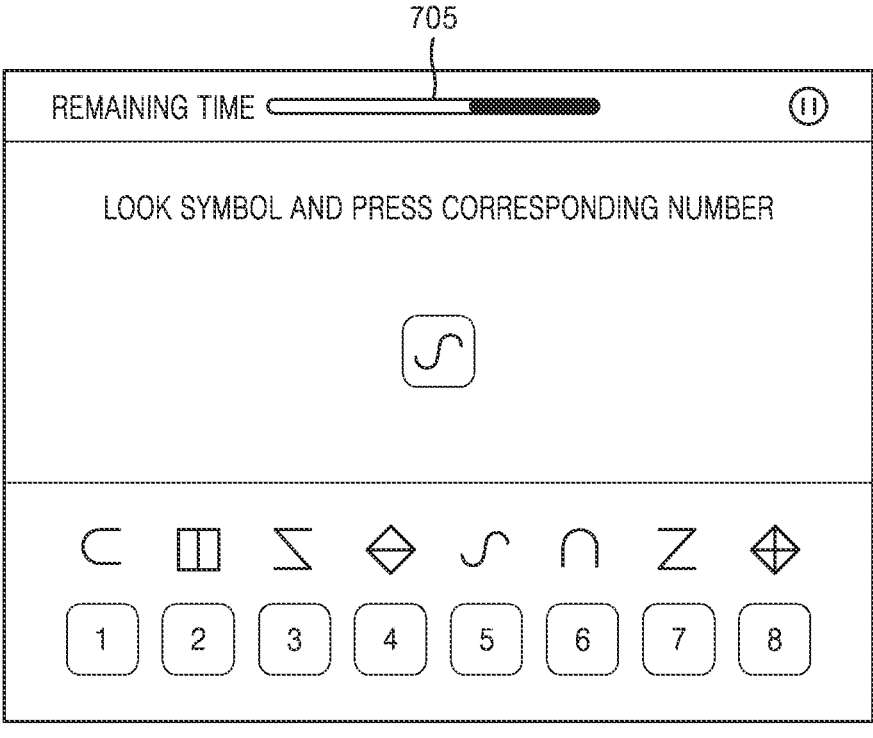

FIG. 7J illustrates an execution screen of the third test process. The screen of FIG. 7J may include a third instruction, a symbol image displayed in the center of the screen, a plurality of symbol images displayed at the bottom of the screen, and a plurality of numbers respectively matched with the plurality of symbol images. A user may check the third instruction, search for a symbol image most similar to the symbol image displayed in the center of the screen, and choose a number matched with a found symbol image. In FIG. 7J, time elapsed until the user chooses a number may be counted by a progress bar 705.

Figure 7K:
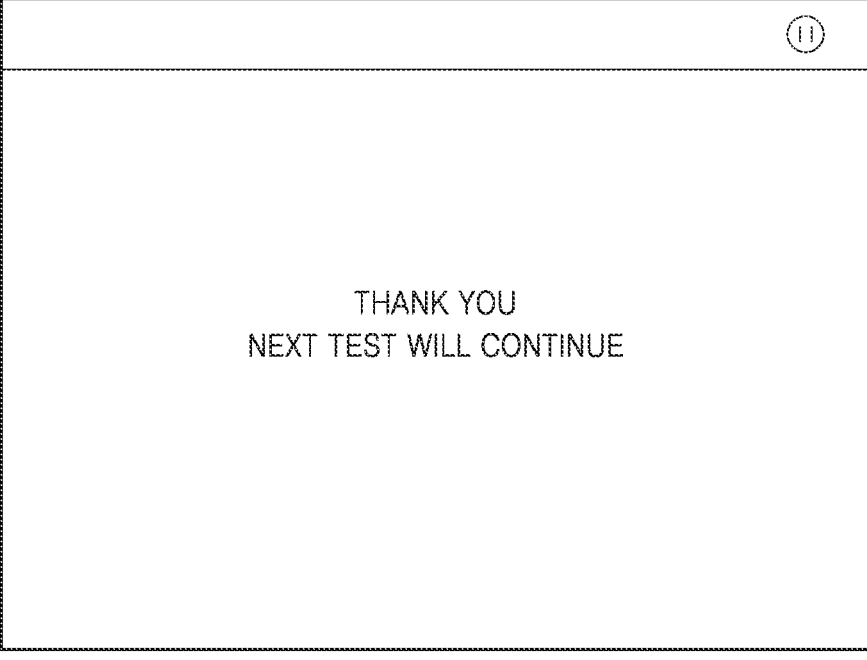

FIG. 7K illustrates a screen indicating completion of the performing of the third test process and a start of a next test process.

Referring back to FIG. 3, the first processing unit 152 may perform the third test process including the (4-1)th test process and the (4-2)th test process. According to the present embodiment, the first processing unit 152 may perform the third test process a plurality of times.

When the (4-1)th test process is performed, the first processing unit 152 may illustrate a pre-set first presented image and provide, to the user terminal 200, the (4-1)th instruction, in which it is instructed to choose whether the number of colors in the pre-set first presented image is equal to or greater than a pre-set number.

The first processing unit 152 may receive, from the user terminal 200, a result of choosing whether the number of colors in the pre-set first presented image is equal to or greater than the pre-set number in response to the (4-1)th instruction, and calculate the (4-1)th test score by comparing the result with a correct answer. According to the present embodiment, the (4-1)th test score may be calculated to be high when there are many results determined to be correct answers compared to the total number of times the (4-1)th test processes have been performed.

According to the present embodiment, before the (4-1)th test process is performed, the first processing unit 152 may provide, in at least one of a text and an instruction screen, a method of performing the (4-1)th test process to the user terminal 200.

The first processing unit 152 may perform the (4-2)th test process when a pre-set time has elapsed after the performing of the (4-1)th test process is completed.

When the (4-2)th test process is performed, the first processing unit 152 may illustrate a pre-set second presented image and provide, to the user terminal 200, the (4-2)th instruction, in which it is instructed to choose whether the pre-set second presented image is the same as the pre-set first presented image shown previously.

The first processing unit 152 may receive, from the user terminal 200, a result of choosing whether the pre-set second presented image is the same as the pre-set first presented image shown previously, in response to the (4-2)th instruction, and compare the result with a correct answer.

The first processing unit 152 may count a first spent time from when the (4-2)th instruction is provided to when it is chosen whether the pre-set second presented image is the same as the pre-set first presented image shown previously.

The first processing unit 152 may calculate the (4-2)th test score by reflecting a result of the comparing and a result of the counting. According to the present embodiment, the (4-2)th test score may be calculated differently according to the results of choosing determined to be correct answers compared to the total number of times the (4-2)th test processes have been performed, and the result of counting. Even when there are many results of choosing, determined to be correct answers, compared to the total number of times the (4-2)th test processes have been performed, the (4-2)th test score may be low when the result of counting the first spent time is high. Alternatively, even when there are few results of choosing, determined to be correct answers, compared to the total number of times the (4-2)th test processes have been performed, the (4-2)th test score may be high when the result of counting the first spent time is low.

According to the present embodiment, before the (4-2)th test process is performed, the first processing unit 152 may provide, in at least one of a text and an instruction screen, a method of performing the (4-2)th test process to the user terminal 200.

According to a selective embodiment, the first processing unit 152 may calculate the third test score by adding the (4-1)th test score and the (4-2)th test score. Alternatively, the first processing unit 152 may not add the (4-1)th test score and the (4-2)th test score, but may use the (4-1)th test score and the (4-2)th test score each to evaluate cognitive function decline. According to the present embodiment, it may be evaluated that visual perception memory is good when the third test score is higher than the third criterion cut-off score, and is declined when the third test score is lower than the third criterion cut-off score.

FIGS. 8A through 8H illustrate examples of screens provided to the user terminal 200 to perform the fourth test process. FIGS. 8A through 8D illustrate examples of screens for describing the (4-1)th test process and FIGS. 8E through 8H illustrate examples of screens for describing the (3-2)th test process.

Figure 8A:
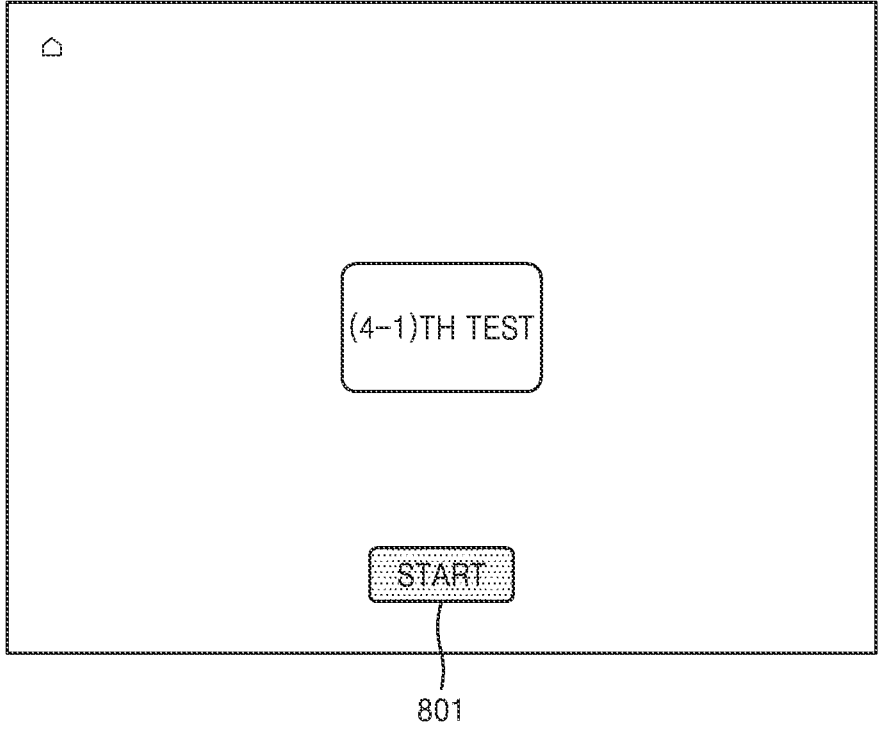

FIG. 8A illustrates a start screen of the (4-1)th test process. When an input of a start button 801 is received, a next screen may be displayed.

Figure 8B:
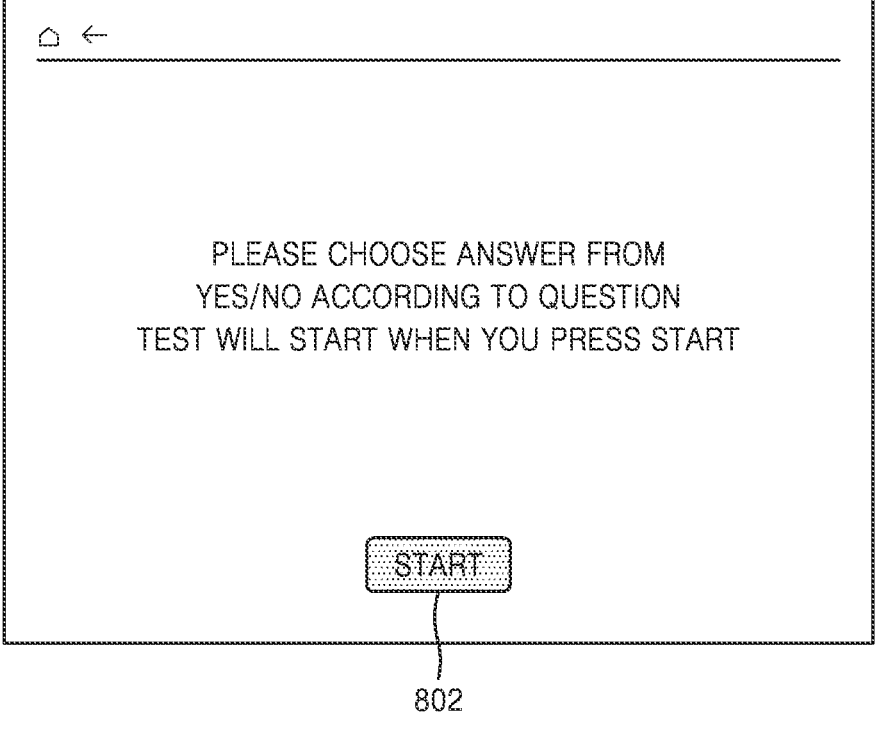

FIG. 8B illustrates a screen providing, in a text, a method of performing the (4-1)th test process, and indicating a start of the (4-1)th test process. When a start button 802 is input, a next screen may be displayed.

Figure 8C:
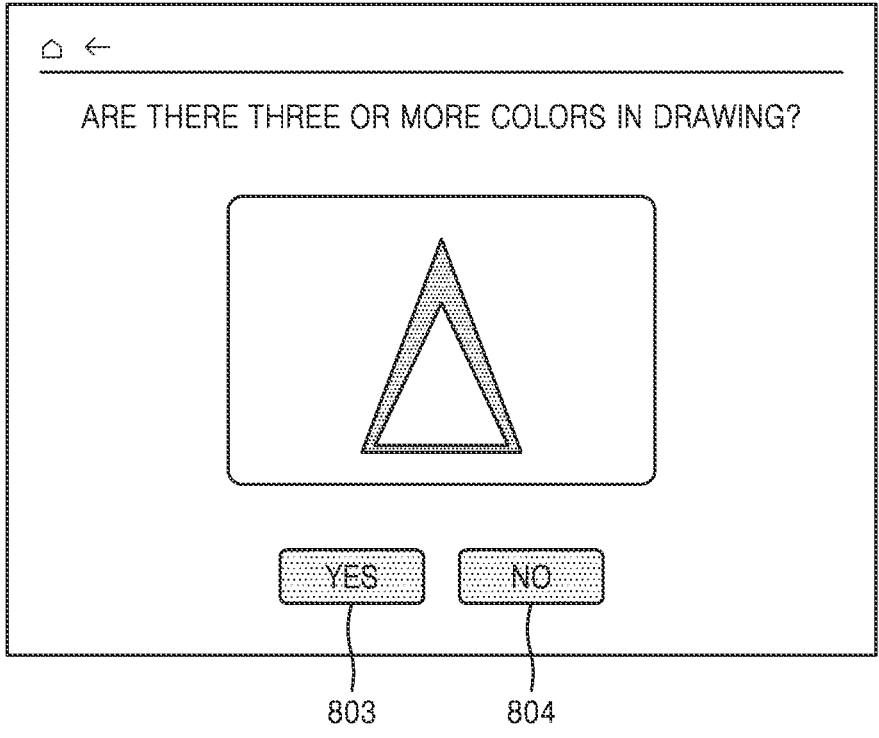

FIG. 8C illustrates a screen for performing the (4-1)th test process. The user may check the (4-1)th instruction and choose one of a Yes button 803 and a No button 804 in response to whether the number of colors in the first presented image is equal to or greater than a pre-set number. Here, a progress bar (not shown) performing at least one of a function of counting a time limit and a function of illustrating a work progress degree may be further provided.

Figure 8D:
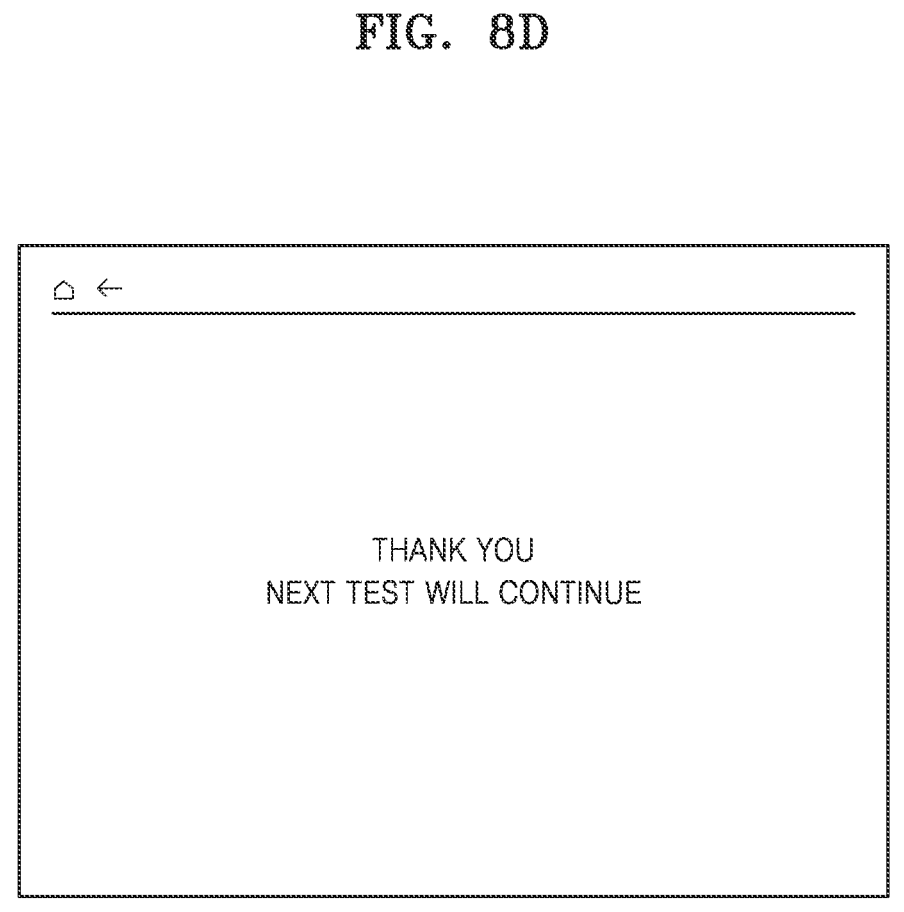

FIG. 8D illustrates a screen indicating completion of the performing of the (4-1)th test process and a start of a next test process.

Figure 8E:
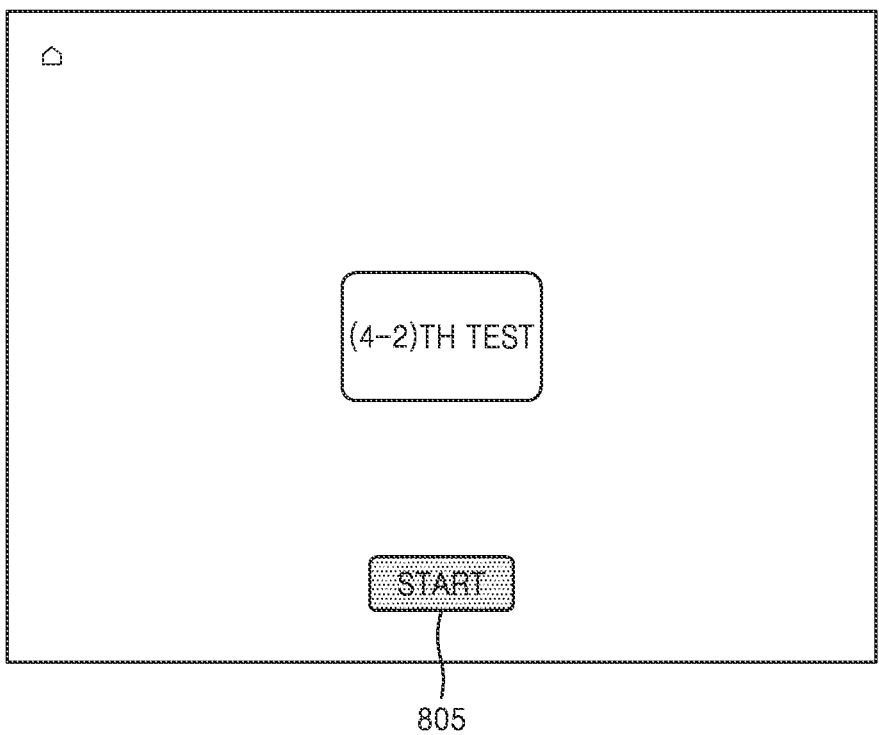

FIG. 8E illustrates a start screen of the (3-2)th test process. When an input of a start button 805 is received, a next screen may be displayed. Here, the start screen of the (3-2)th test process may be provided to the user terminal 200 after the performing of the (2-2)th test process is completed.

Figure 8F:
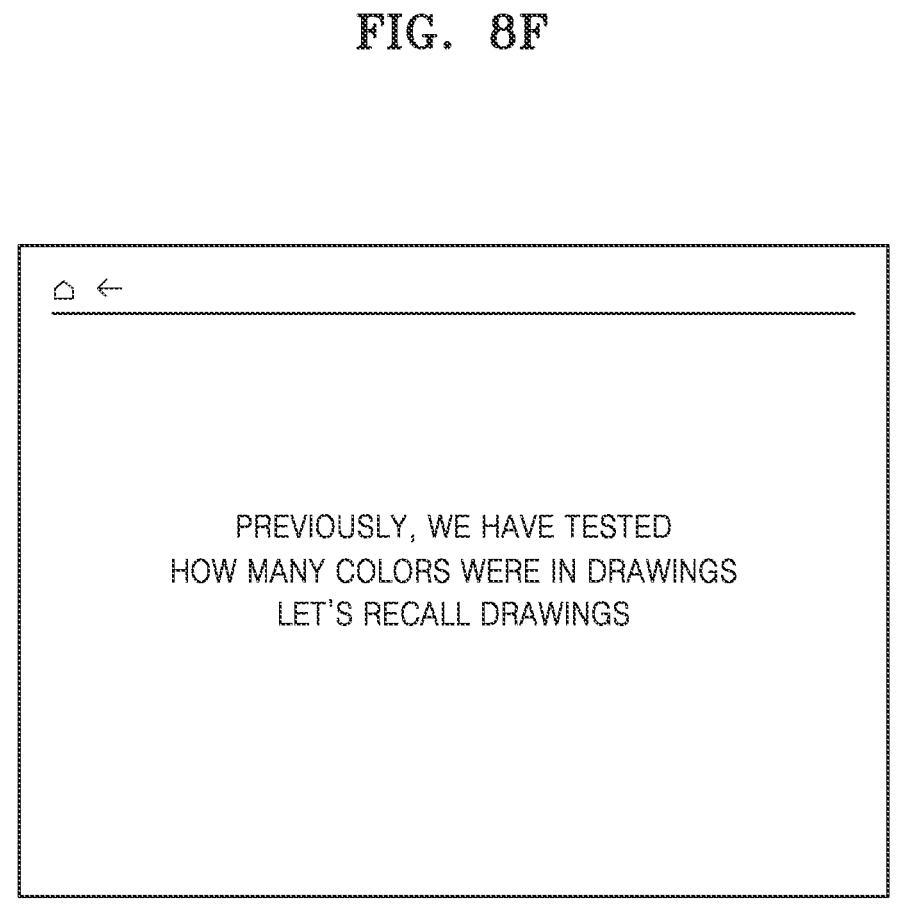

FIG. 8F illustrates a screen recommending to recall the first presented image provided while the (4-1)th test process was performed.

Figure 8G:
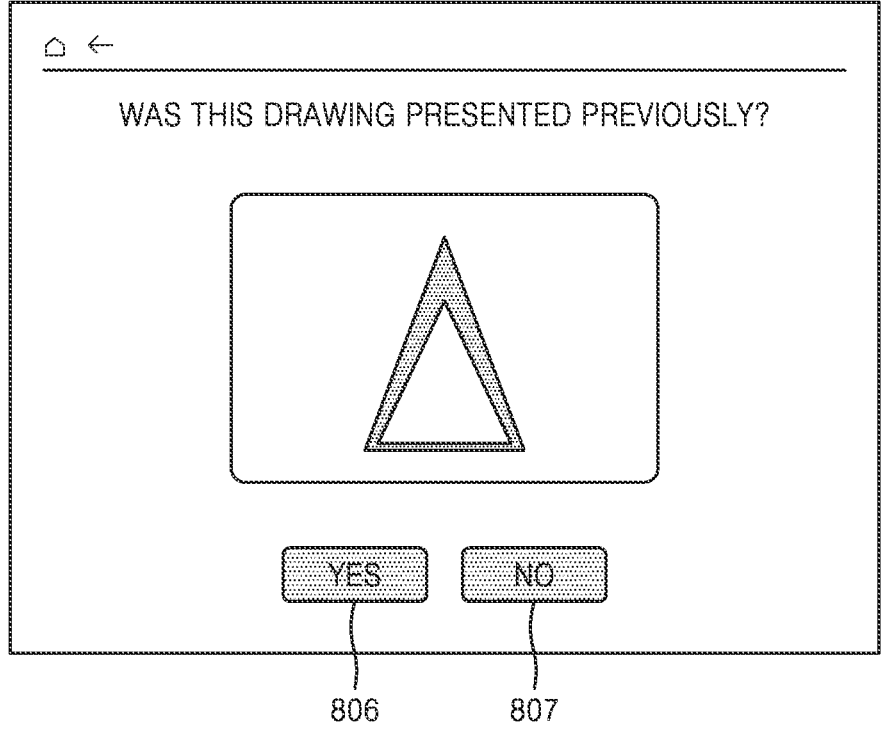

FIG. 8G illustrates a screen for performing the (3-2)th test process. The user may check the (3-2)th instruction and choose one of a Yes button 806 and a No button 807 in response to whether the second presented image is the same as the first presented image. Here, a progress bar (not shown) performing at least one of a function of counting a time limit and a function of illustrating a work progress degree may be further provided.

Figure 8H:
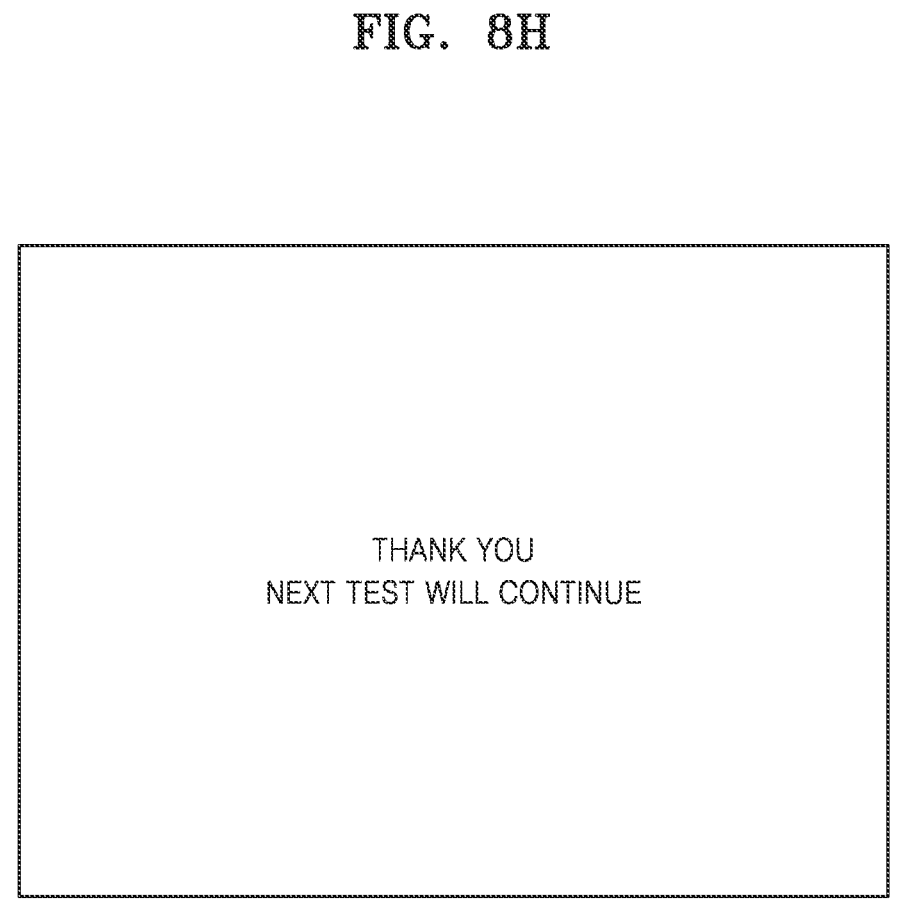

FIG. 8H illustrates a screen indicating completion of the performing of the (3-2)th test process and a start of a next test process.

Referring back to FIG. 3, the first processing unit 152 may perform the fourth test process including the (5-1)th test process and the (5-2)th test process. According to the present embodiment, the first processing unit 152 may perform the fourth test process a plurality of times, excluding a practice test.

When the (5-1)th test process is performed, the first processing unit 152 may illustrate a pre-set presented word and two choice words, and provide, to the user terminal 200, the (5-1)th instruction, in which it is instructed to choose a same word as the pre-set presented word from among the two choice words.

The first processing unit 152 may receive, from the user terminal 200, a result of choosing the same word as the pre-set presented word from among the two choice words, in response to the (5-1)th instruction, and calculate the (5-1)th test score by comparing the result with a correct answer. According to the present embodiment, the (5-1)th test score may be calculated to be high when there are many results determined to be correct answers compared to the total number of times the (5-1)th test processes have been performed.

According to the present embodiment, before the (5-1)th test process is performed, the first processing unit 152 may provide, in at least one of a text and an instruction screen, a method of performing the (5-1)th test process to the user terminal 200, and perform a practice test for the (5-1)th test process.

The first processing unit 152 may perform the (5-2)th test process after the performing of the (5-1)th test process is completed.

When the (5-2)th test process is performed, the first processing unit 152 may illustrate a pre-set presented word and two color choice words and provide, to the user terminal 200, the (5-2)th instruction, in which it is instructed to choose a word having a same color as the pre-set presented word from among the two color choice words.

The first processing unit 152 may receive, from the user terminal 200, a result of choosing the word having the same color as the pre-set presented word from among the two color choice words, in response to the (5-2)th instruction, and calculate the (5-2)th test score by comparing the result with a correct answer. According to the present embodiment, the (5-2)th test score may be calculated to be high when there are many results determined to be correct answers compared to the total number of times the (5-2)th test processes have been performed.

According to the present embodiment, before the (5-2)th test process is performed, the first processing unit 152 may provide, in at least one of a text and an instruction screen, a method of performing the (5-2)th test process to the user terminal 200, and perform a practice test for the (5-2)th test process.

According to a selective embodiment, the first processing unit 152 may calculate the fourth test score by adding the (5-1)th test score and the (5-2)th test score. Alternatively, the first processing unit 152 may not add the (5-1)th test score and the (5-2)th test score, but may use the (5-1)th test score and the (5-2)th test score each to evaluate cognitive function decline. According to the present embodiment, it may be evaluated that an inhibitory function is good when the fourth test score is higher than the fourth criterion cut-off score, and is declined when the fourth test score is lower than the fourth criterion cut-off score.

Figure 9A:
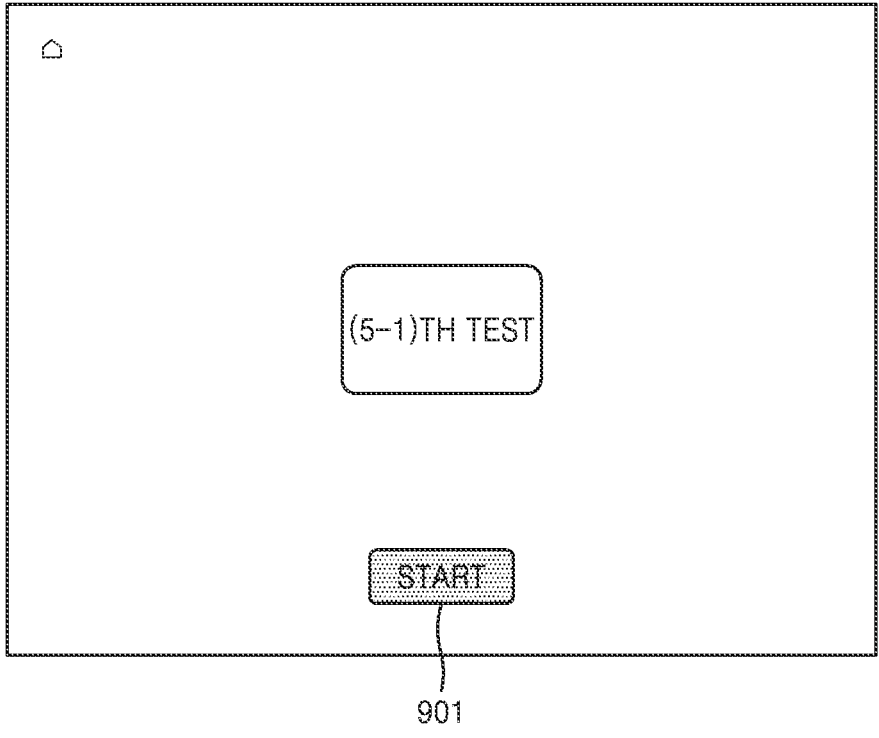

FIGS. 9A through 9O illustrate examples of screens provided to the user terminal 200 to perform the fourth test process. FIGS. 9A through 9I illustrate examples of screens for describing the (5-1)th test process and FIGS. 9J through 9O illustrate examples of screens for describing the (5-2)th test process.

FIG. 9A illustrates a start screen of the (5-1)th test process. When an input of a start button 901 is received, a screen for the (5-1)th test process may be displayed.

Figure 9B:
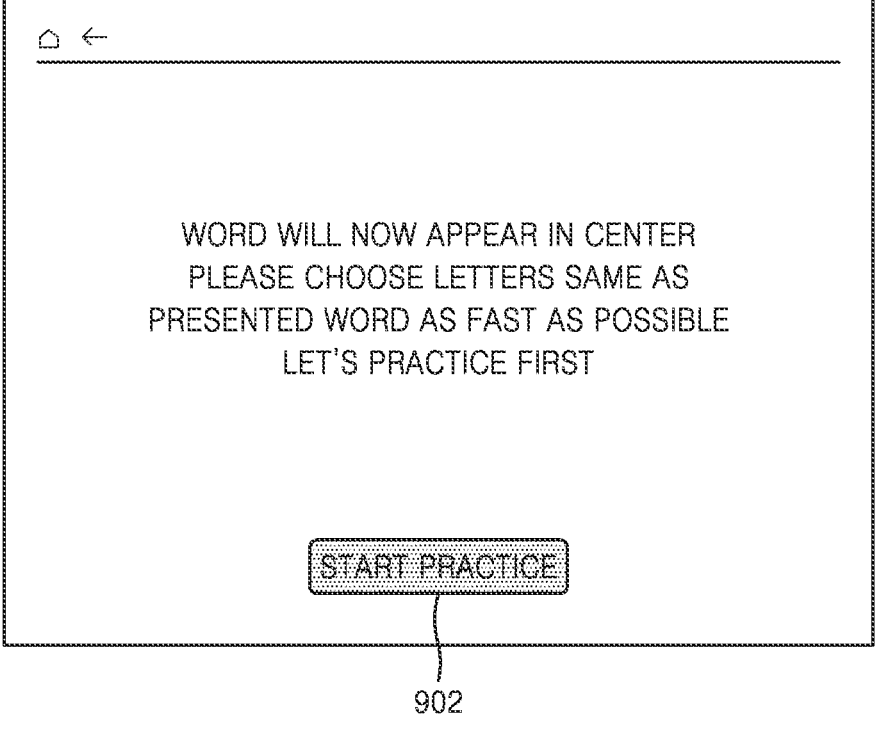

FIG. 9B illustrates a screen in which a method of performing the (5-1)th test process is provided in a text and a start of a practice test process (5-1)th practice test process) for the (5-1)th test process is notified. When a practice start button 902 is input, a next screen may be displayed.

Figure 9C:
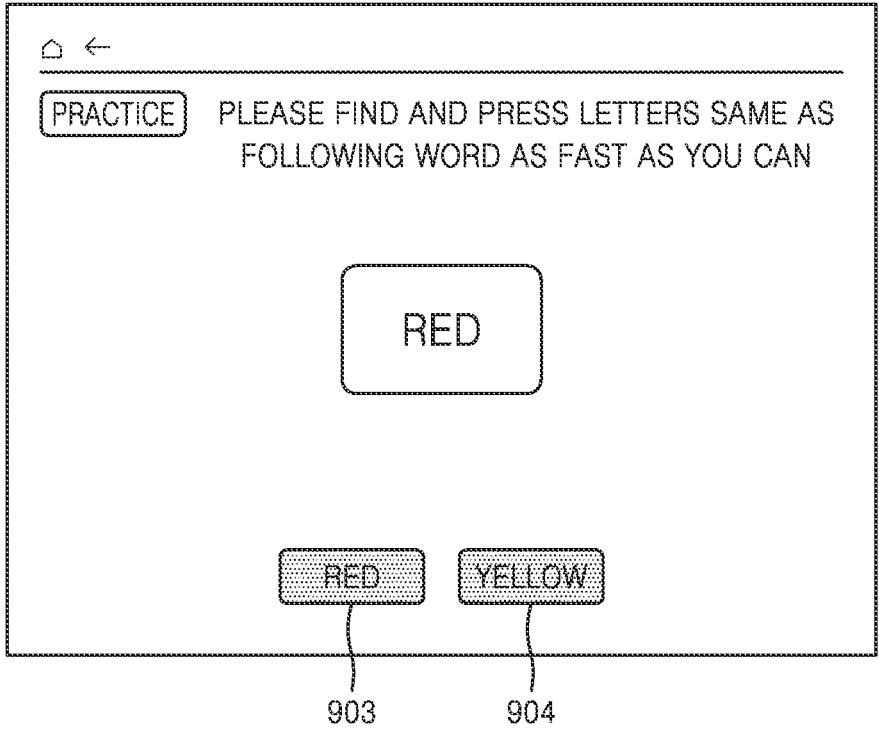

FIG. 9C illustrates a screen for performing the (5-1)th practice test process. After checking a (5-1)th practice instruction, the user may choose a same word as a presented word from among a first choice word 903 and a second choice word 904. Here, a progress bar (not shown) performing at least one of a function of counting a time limit and a function of illustrating a work progress degree may be further provided.

Figure 9D:
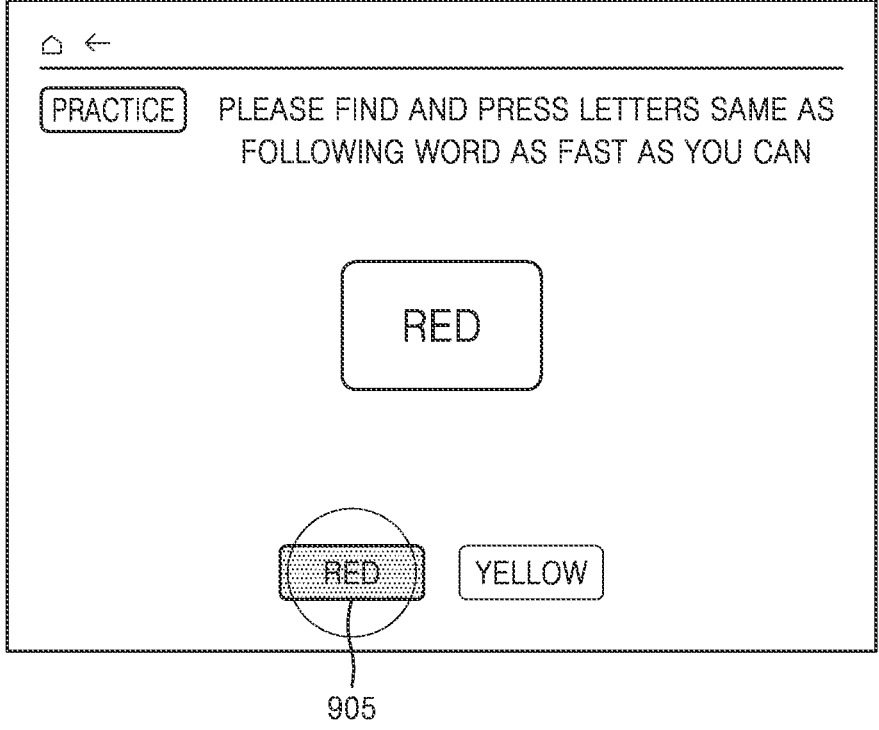

FIG. 9D illustrates a screen indicating whether a result of choosing a first choice word 905 from FIG. 9C is a correct answer. Here, the first choice word 905 is the same as the first choice word 903 of FIG. 9C.

Figure 9E:
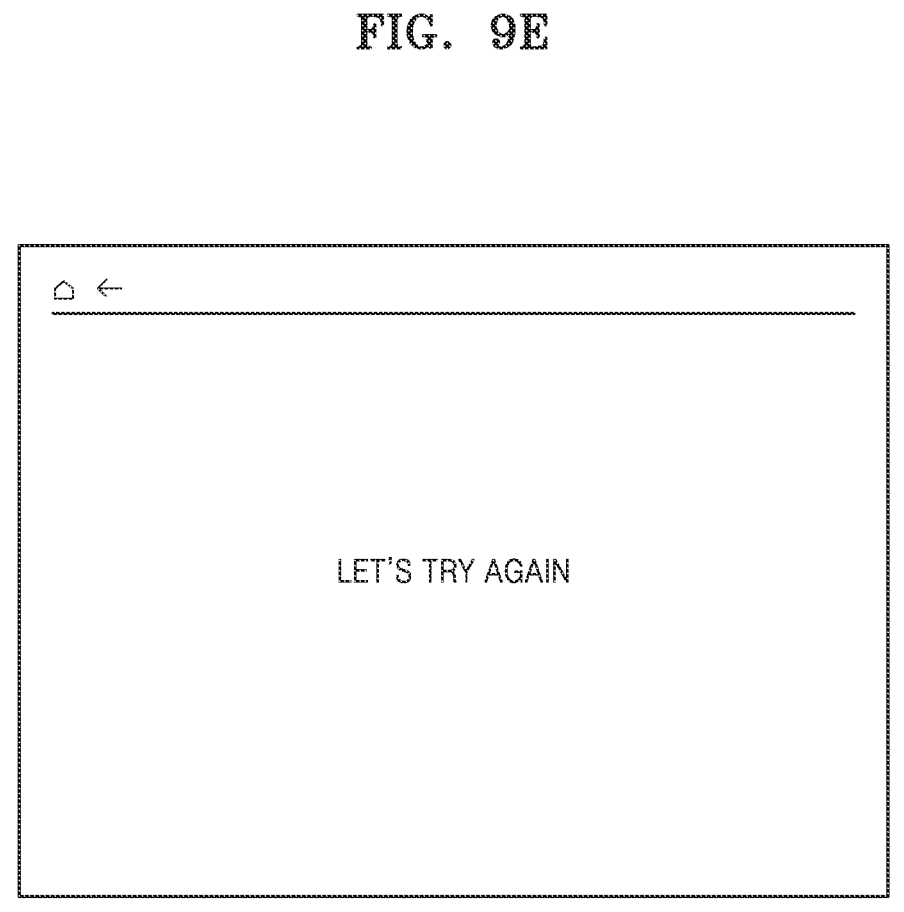

FIG. 9E illustrates a screen indicating a rerun of the (5-1)th practice test process. The (5-1)th practice test process may be rerun when a result of performing the (5-1)th practice test process is a wrong answer.

Figure 9F:
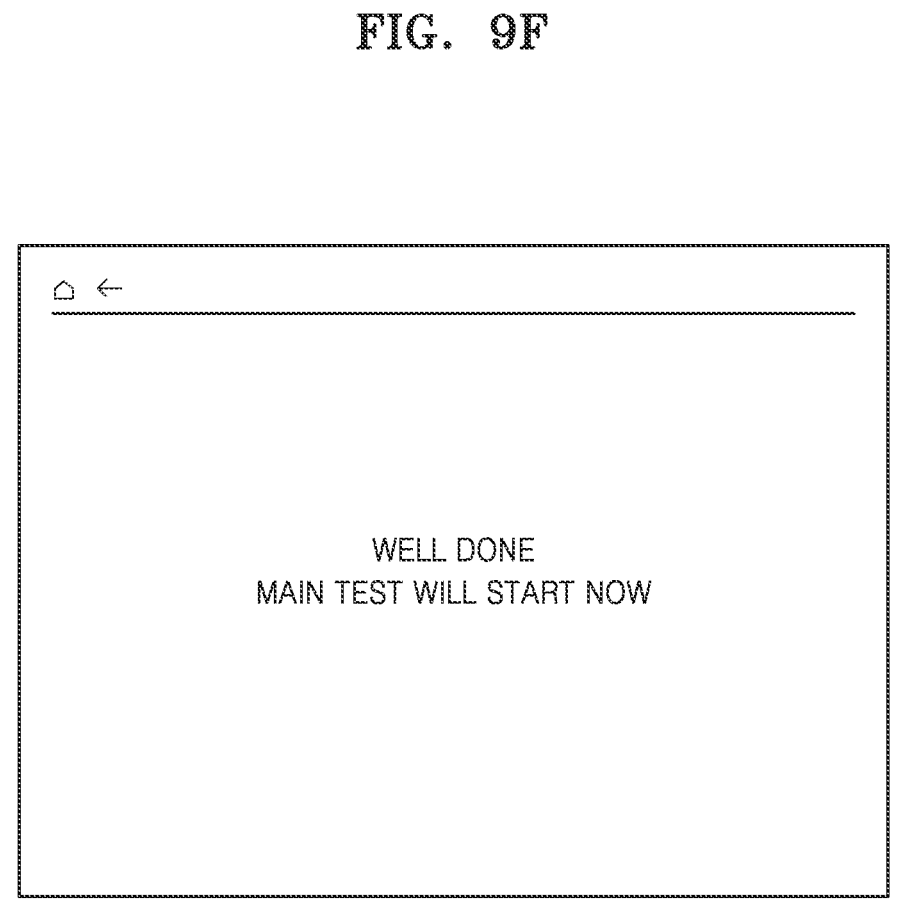

FIG. 9F illustrates a screen indicating completion of the performing of the (5-1)th practice test process, and performing of a main test.

Figure 9G:
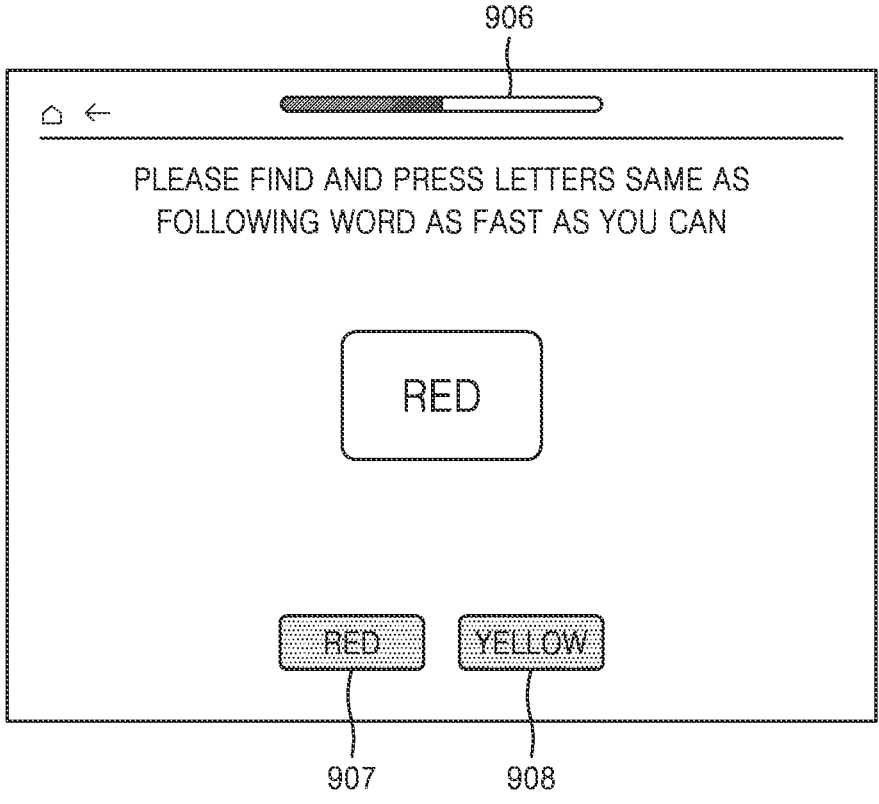

FIG. 9G illustrates a screen for performing the (5-1)th test process. After checking the (5-1)th instruction, the user may choose a same word as a presented word from among a first choice word 907 and a second choice word 908, while looking at a progress bar 906.

Figure 9H:
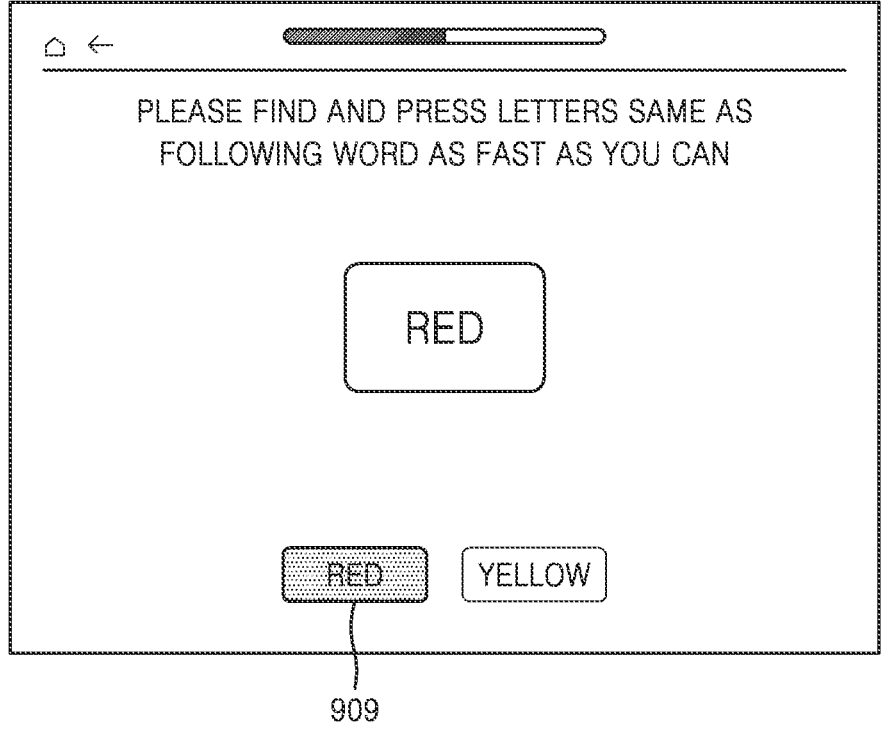

FIG. 9H illustrates a screen indicating whether a result of choosing a first choice word 909 from FIG. 9G is a correct answer. Here, the first choice word 909 is the same as the first choice word 907 of FIG. 9G.

Figure 9I:
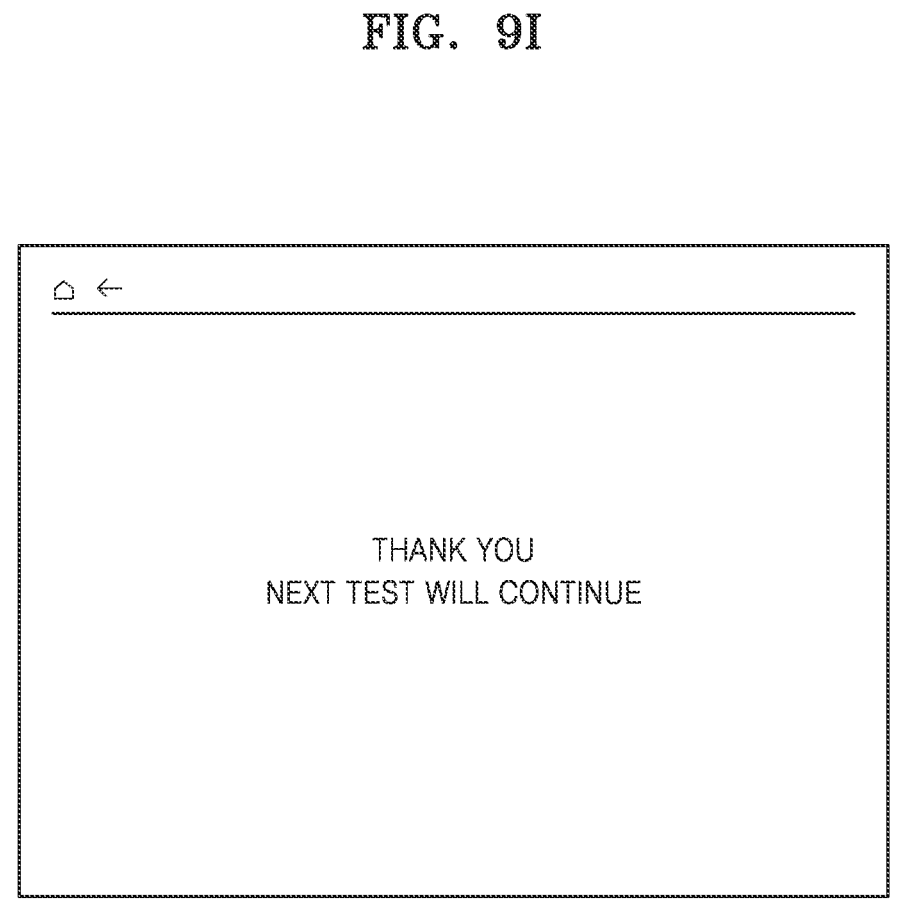

FIG. 9I illustrates a screen indicating completion of the performing of the (5-1)th test process and a start of a next test process.

Figure 9J:
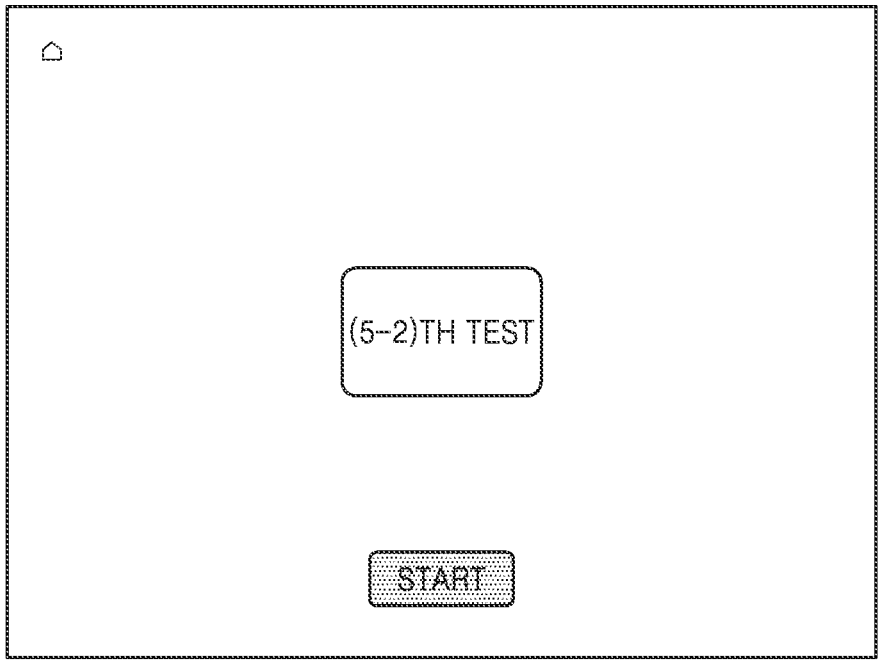

FIG. 9J illustrates a start screen of the (5-2)th test process.

Figure 9K:
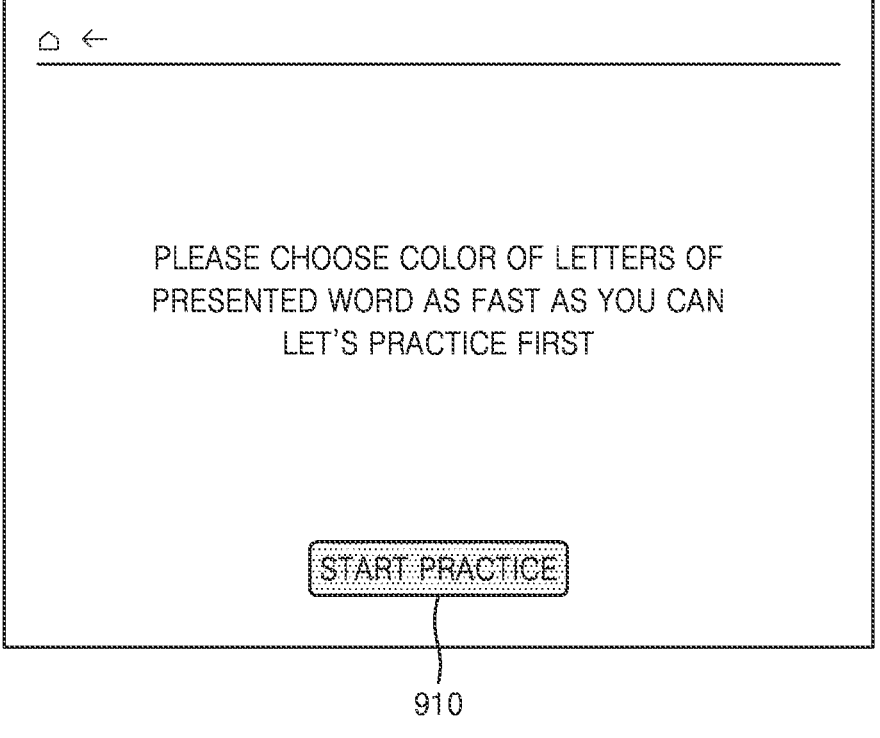

FIG. 9K illustrates a screen in which a method of performing the (5-2)th test process is provided in a text and a start of a practice test process ((5-2)th practice test process) for the (5-2)th test process is notified. When a practice start button 910 is input, a next screen may be displayed.

Figure 9L:
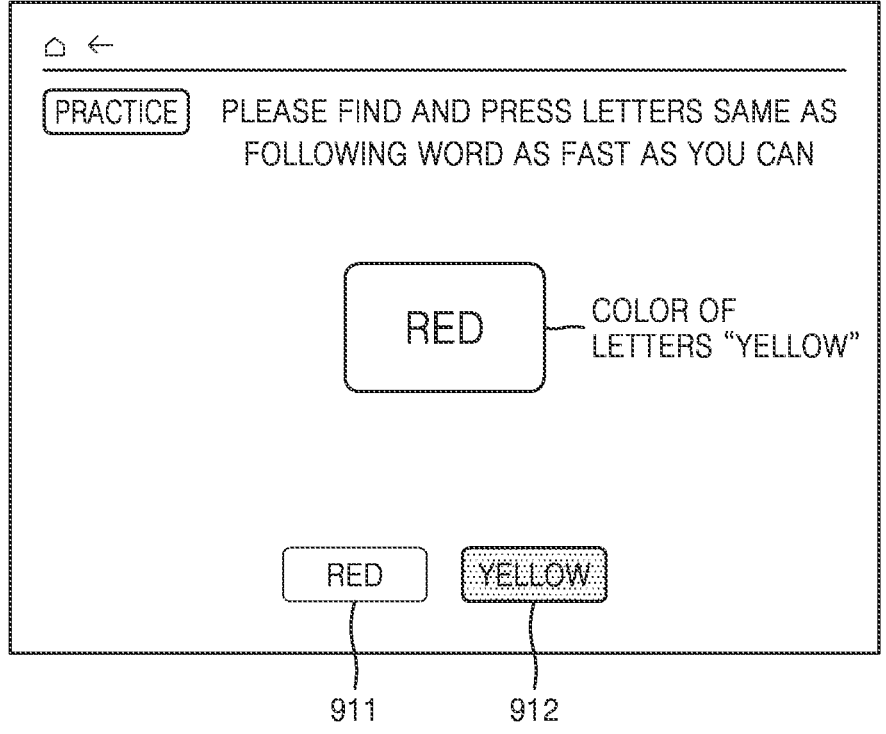

FIG. 9L illustrates a screen for performing the (5-2)th practice test process. After checking a (5-2)th practice instruction, the user may choose a word having a same color as a presented word from among a first choice word 911 and a second choice word 912. Here, a progress bar (not shown) performing at least one of a function of counting a time limit and a function of illustrating a work progress degree may be further provided. FIG. 9L illustrates an example in which the user chose the second choice word 912.

Figure 9M:
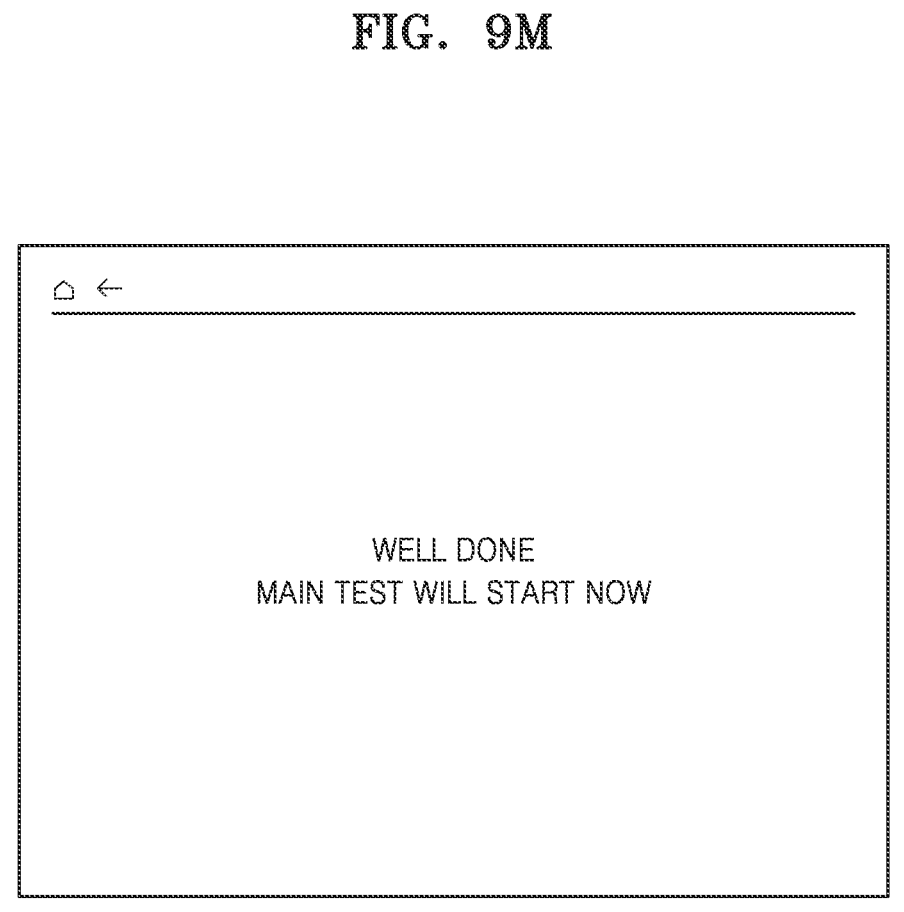

FIG. 9M illustrates a screen indicating completion of the performing of the (5-2)th practice test process, and performing of a main test.

Figure 9N:
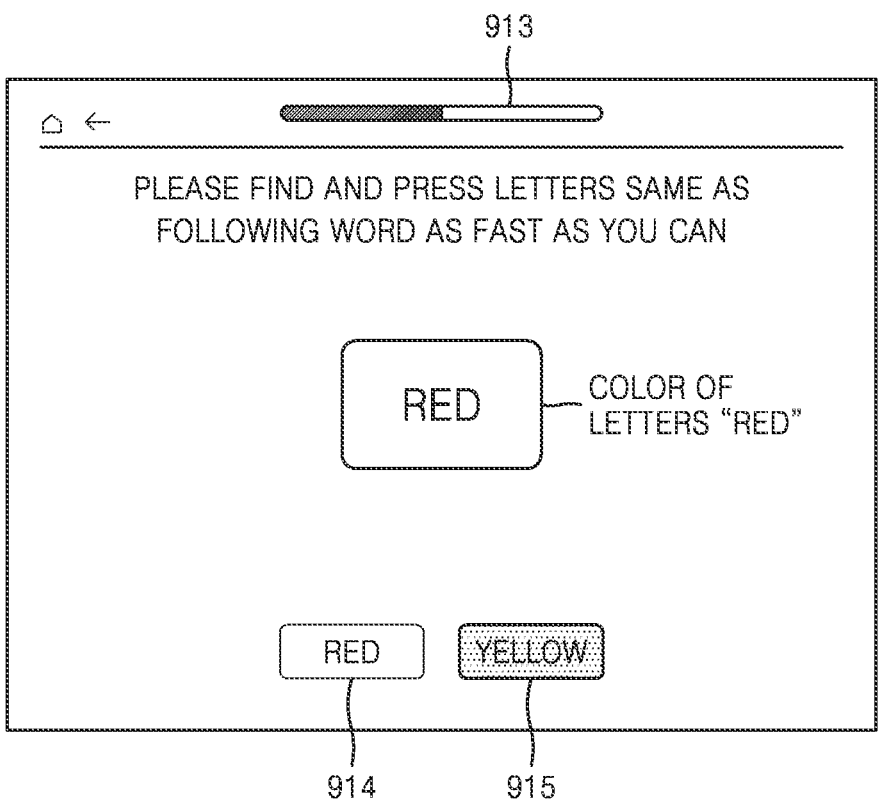

FIG. 9N illustrates a screen for performing the (5-2)th test process. After checking the (5-2)th instruction, the user may choose a word having a same color as a presented word from among a first choice word 914 and a second choice word 915, while looking at a progress bar 913. FIG. 9N illustrates an example in which the user chose the second choice word 915.

FIG. 9O illustrates a screen indicating completion of the performing of the (5-2)th test process and a start of a next test process.

Referring back to FIG. 3, the first processing unit 152 may perform the sixth test process. According to the present embodiment, the first processing unit 152 may perform the sixth test process a plurality of times, excluding a practice test.

When the sixth test process is performed, the first processing unit 152 may provide the pre-set face presented image in which an emotion is expressed and a plurality of emotion buttons for choosing a state of the emotion appearing in the pre-set face presented image. The first processing unit 152 may provide a sixth instruction to choose the state of the emotion appearing in the pre-set face presented image by using any one of the plurality of emotion buttons to the user terminal 200. Here, the plurality of emotion buttons may include happiness button, surprise button, sadness button, fear button, anger button, and neutrality button.

The first processing unit 152 may receive a result of choosing the state of the emotion appearing in the pre-set face presented image by using any one of the plurality of emotion buttons in response to the sixth instruction and calculate a sixth test score by comparing a choice result with a correct answer. According to the present embodiment, the sixth test score may be calculated to be high when there are many results determined to be correct answers compared to the total number of times the sixth test processes have been performed.

According to the present embodiment, before the sixth test process is performed, the first processing unit 152 may provide, in at least one of a text and an instruction screen, a method of performing the sixth test process to the user terminal 200, and perform a practice test for the sixth test process.

According to the present embodiment, it may be evaluated that emotion intensity cognitive power is good when the sixth test score is higher than the sixth criterion cut-off score, and is declined when the sixth test score is lower than the sixth criterion cut-off score.

FIGS. 10A through 10G illustrate examples of screens provided to the user terminal 200 to perform the sixth test process.

Figure 10A:
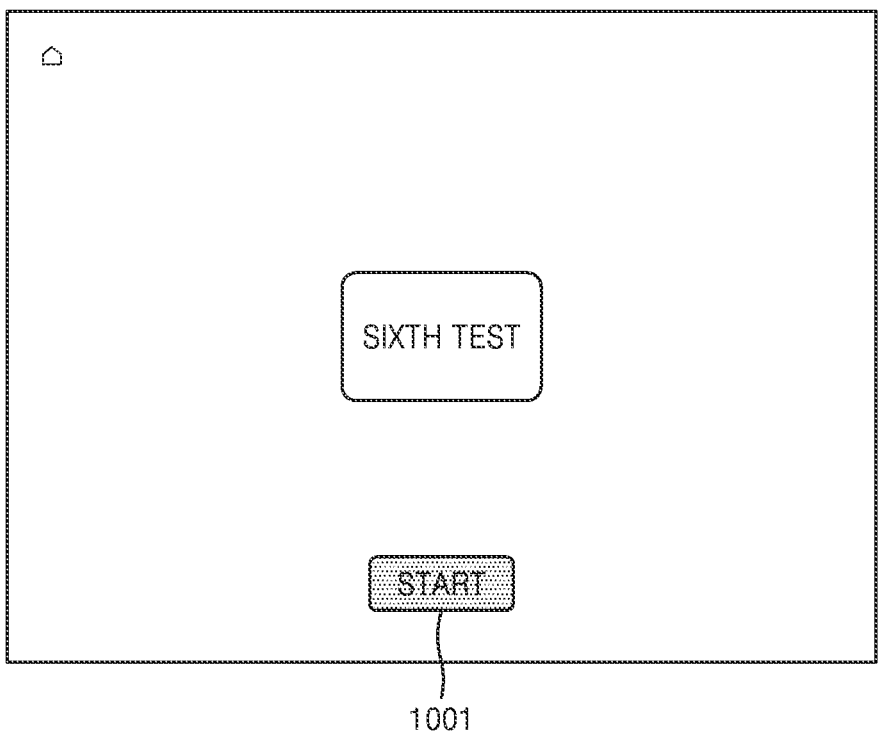

FIG. 10A illustrates a start screen of the sixth test process. When an input of a start button 1001 is received, a next screen may be displayed.

Figure 10B:
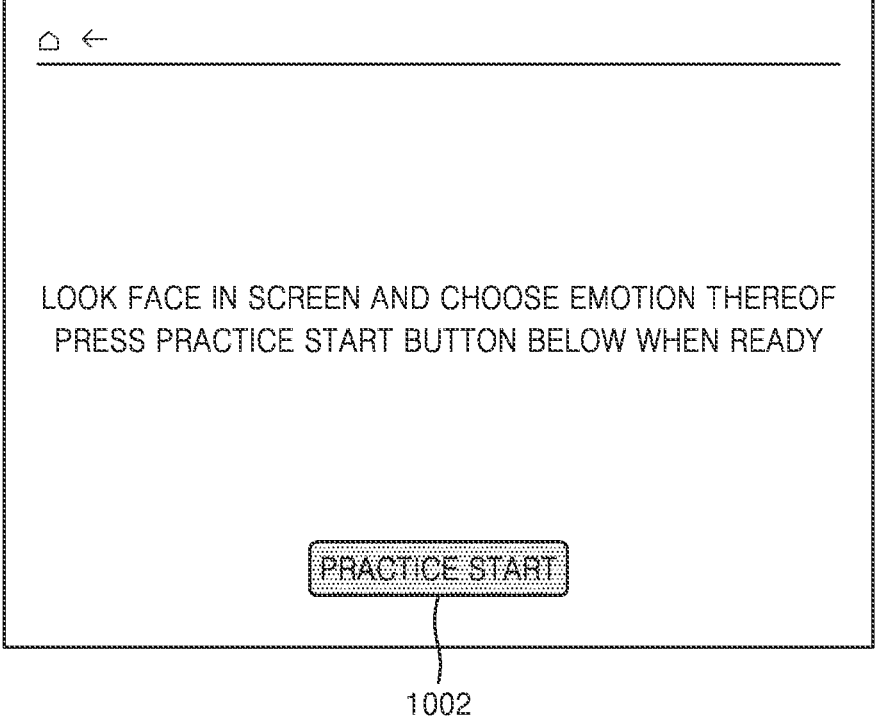

FIG. 10B illustrates a screen in which a method of performing the sixth test process is provided in a text and a start of a practice test process (sixth practice test process) for the sixth test process is notified. When a practice start button 1002 is input, a next screen may be displayed.

Figure 10C:
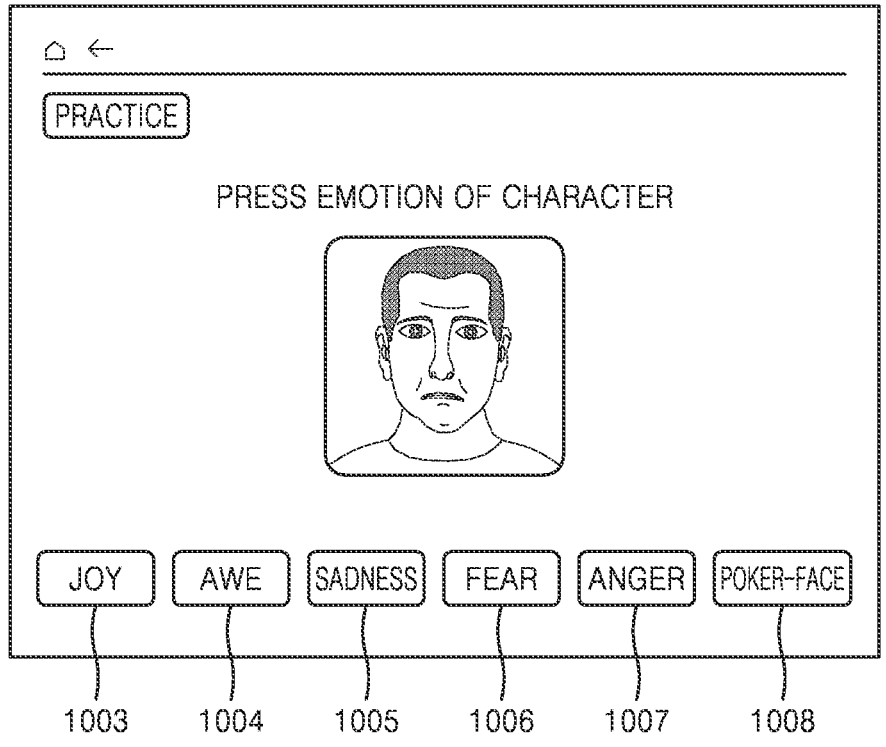

FIG. 10C illustrates a screen for performing the sixth practice test process. The user may check an sixth practice instruction, and then choose one of a plurality of buttons (1003 to 1008) as a state of the emotion shown on a face presented image. Here, a progress bar (not shown) performing at least one of a function of counting a time limit and a function of illustrating a work progress degree may be further provided.

Figure 10D:
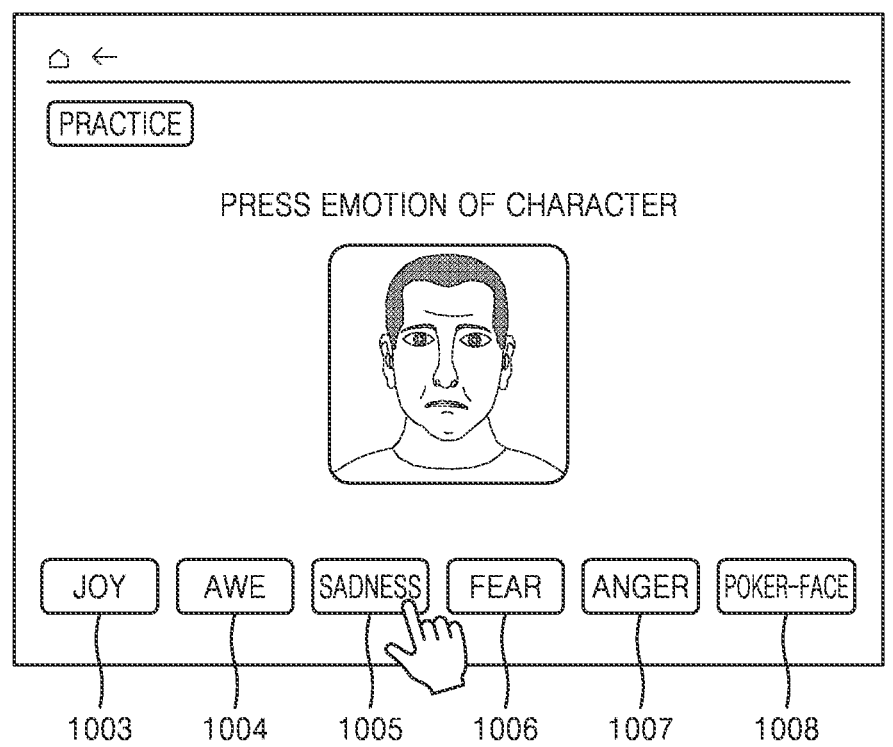

FIG. 10D illustrates a screen showing a result of performing the sixth test process. As an example, it illustrates a case where the user has chosen the sadness button (1005) among a plurality of buttons (1003 to 1008).

Figure 10E:
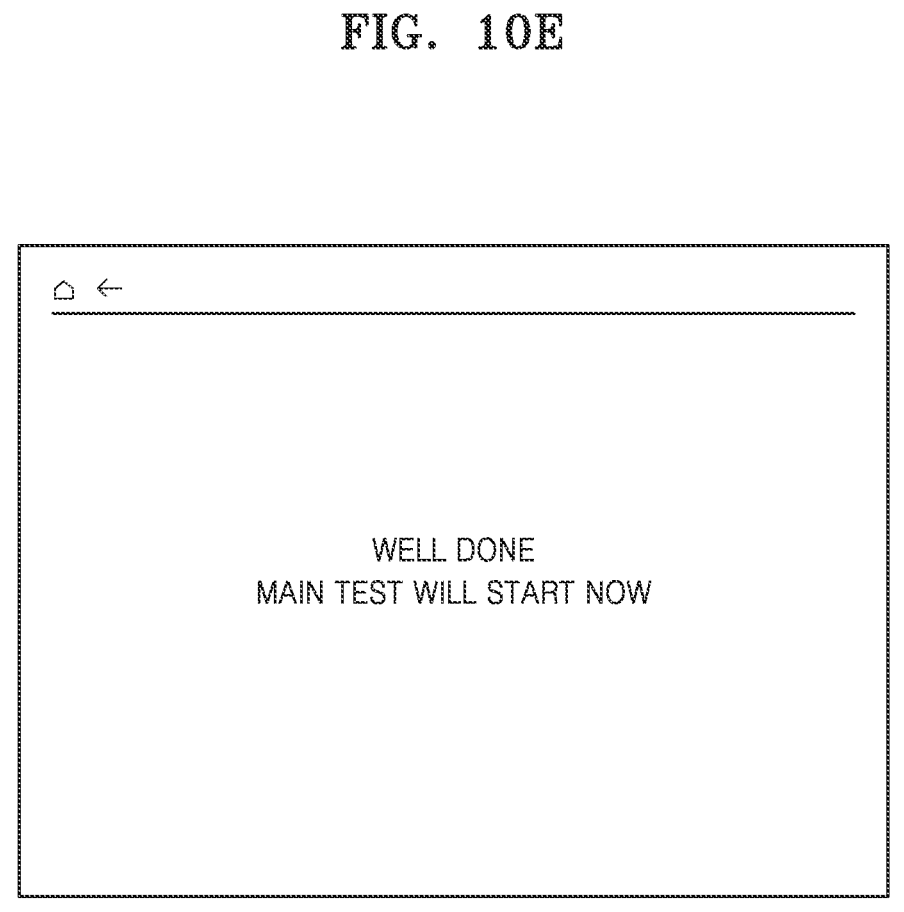

FIG. 10E illustrates illustrates a screen indicating completion of the performing of the sixth practice test process, and performing of a main test.

Figure 10F:
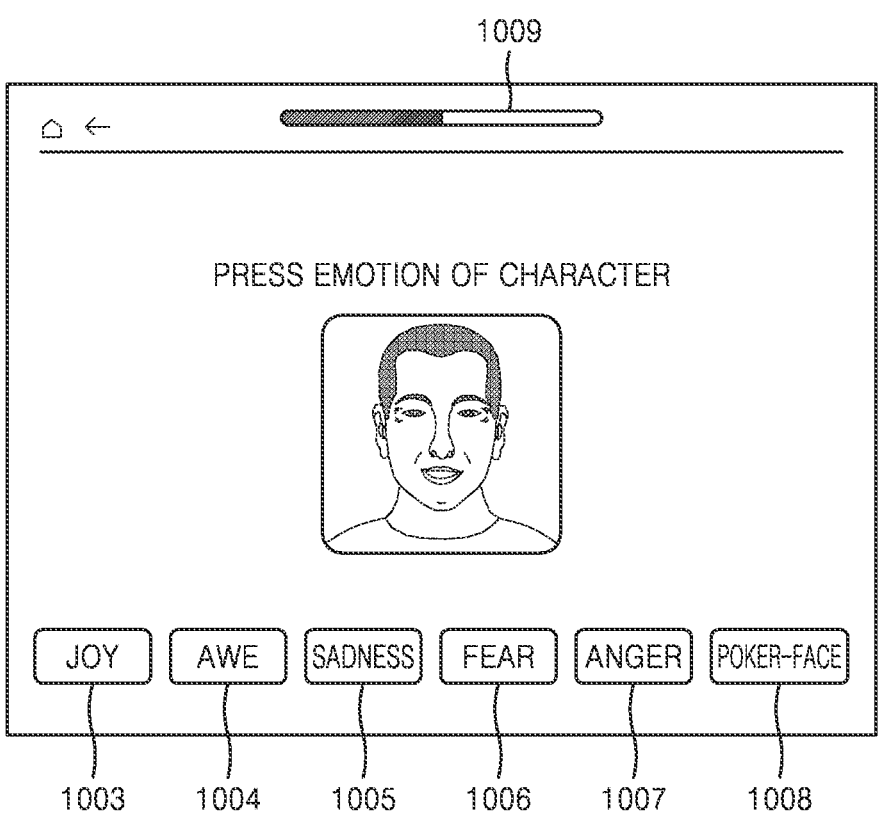

FIG. 10F illustrates an embodiment of a screen for performing the eighth test process. The user may check the sixth instruction, and then choose one of a plurality of emotion buttons (1003 to 1008) as the state of the emotion appearing in the presented image while looking at a progress bar 1009. Here, the time count until one of the plurality of emotion buttons (1003 to 1008) is selected may be output to the first processing unit 152.

Figure 10G:
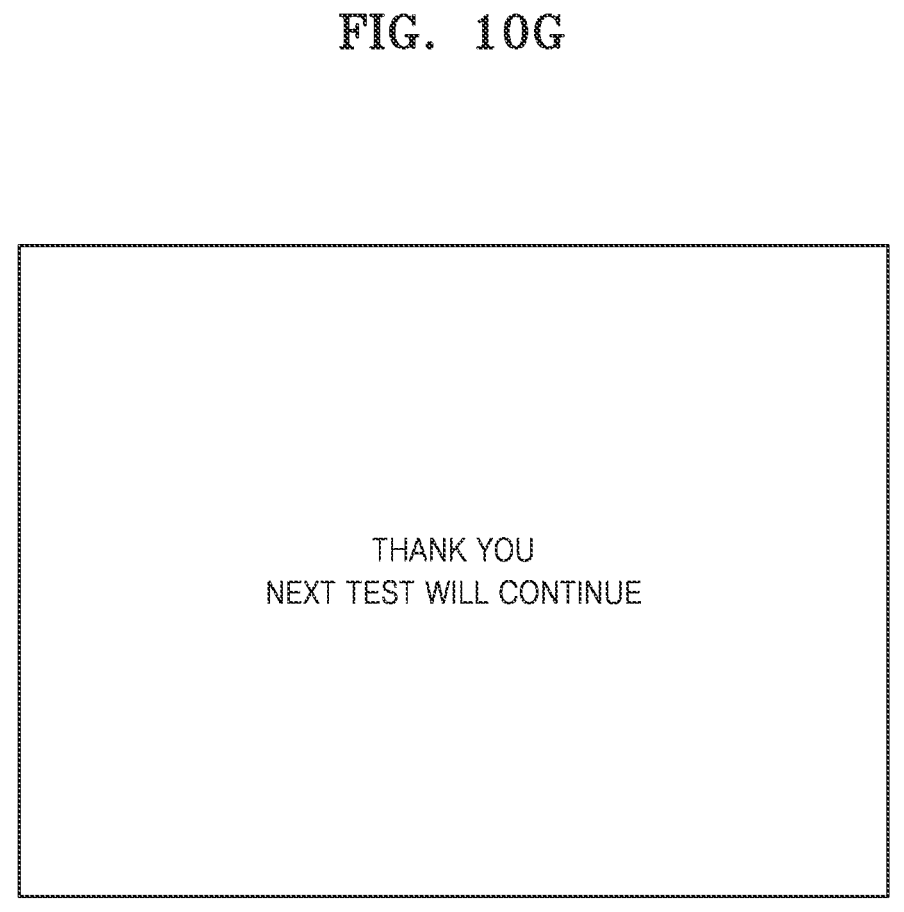

FIG. 10G illustrates a screen indicating completion of the performing of the sixth test process and a start of a next test process.

Referring back to FIG. 3, the first processing unit 152 may perform the second test process including the (7-1)th test process and the (7-2)th test process. In the present embodiment, the first processing unit 152 may perform the (7-1)th test process and the (7-2)th test process a plurality of number of times, excluding practice tests.

When the (7-1)th test process is performed, the first processing unit 152 may provide a (7-1)th instruction to choose an arbitrary number marked as start and choose other presented numbers in descending order or ascending order within a (7-1)th time limit (e.g., 300 seconds) to the user terminal 200.

The first processing unit 152 may receive a result of choosing an arbitrary number marked as start and choosing the other presented numbers in descending or ascending order in response to the (7-1)th instruction from the user terminal 200.

The first processing unit 152 may calculate a (7-1)th test score by counting a time elapsed until a result of choosing the other presented numbers in descending or ascending order becomes a correct answer. In other words, time for performing a task without errors within the (7-1)th time limit may be calculated as the (7-1)th test score. The shorter the time spent performing the task without error, the better the executive function may be evaluated as. Also, when 5 or more incorrect choices are made within the (7-1)th time limit, it may be considered that the (7-1)th test process failed.

According to the present embodiment, before the (7-1)th test process is performed, the first processing unit 152 may provide, in at least one of a text and an instruction screen, a method of performing the (7-1)th test process to the user terminal 200, and perform a practice test for the (7-1)th test process.

The first processing unit 152 may perform the (7-2)th test process when a pre-set time has elapsed after the performing of the (7-1)th test process is completed.

When the (7-2)th test process is performed, the first processing unit 152 may provide a (7-2)th instruction to alternately choose an arbitrary number and a day corresponding to the arbitrary number from among presented numbers and presented days within a (7-2)th time limit to the user terminal 200.

The first processing unit 152 may receive a result of alternately choosing an arbitrary number and a day corresponding to the arbitrary number in response to the (7-2)th instruction from the user terminal 200.

The first processing unit 152 may calculate a (7-2)th test score by counting a time elapsed until a result of choosing the other presented numbers in descending or ascending order becomes a correct answer. In other words, time for performing a task without errors within the (7-2)th time limit may be calculated as the (7-2)th test score. The shorter the time spent performing the task without error, the better the executive function may be evaluated as. Also, when 5 or more incorrect choices are made within the (7-2)th time limit, it may be considered that the (7-2)th test process failed.

According to the present embodiment, before the (7-2)th test process is performed, the first processing unit 152 may provide, in at least one of a text and an instruction screen, a method of performing the (7-2)th test process to the user terminal 200, and perform a practice test for the (7-2)th test process.

According to a selective embodiment, the first processing unit 152 may calculate the seventh test score by adding the (7-1)th test score and the (7-2)th test score. Alternatively, the first processing unit 152 may not add the (7-1)th test score and the (7-2)th test score, but may use the (7-1)th test score and the (7-2)th test score each to evaluate executive function. In the present embodiment, when a result of summing the (7-1)th test score and the (7-2)th test score is higher than the seventh criterion cut-off score, it may be determined that the executive function is good. On the other hand, when the second test score is lower than the seventh criterion cut-off score, it may be determined that the executive function declined.

Figure 11A:
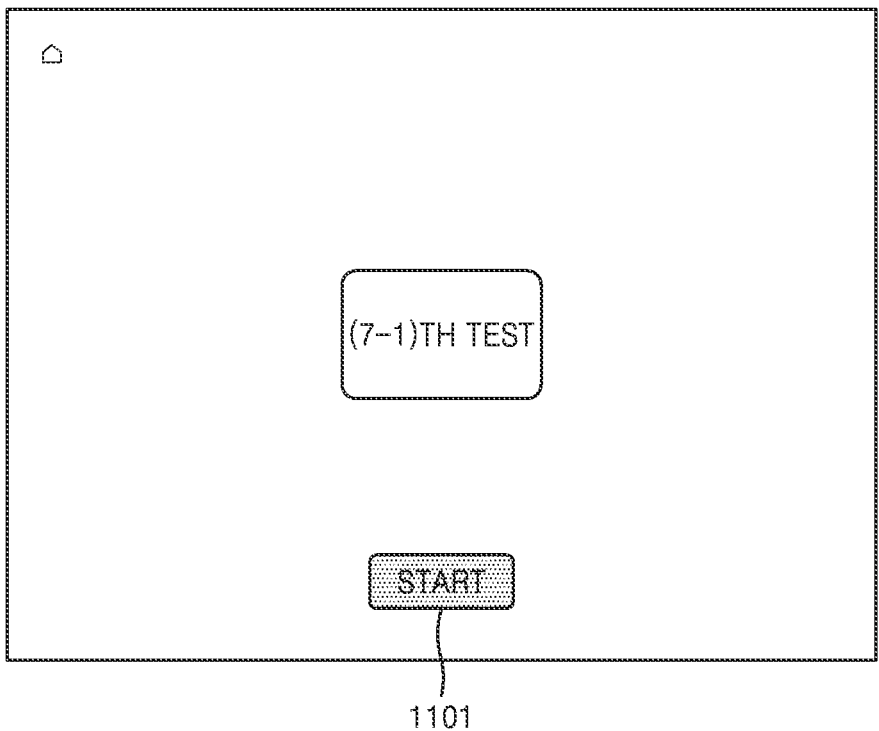
Figure 11B:
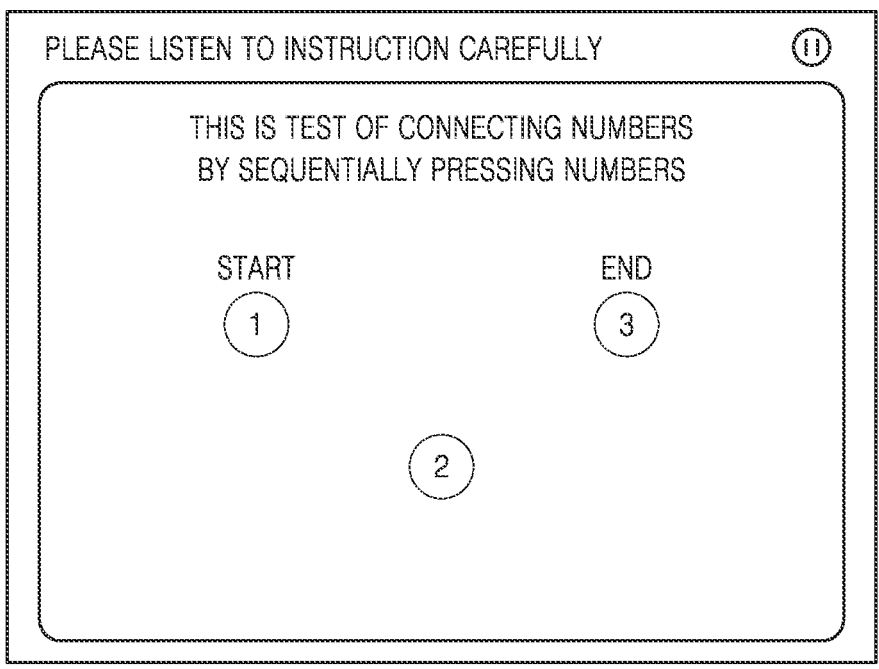
Figure 11C:
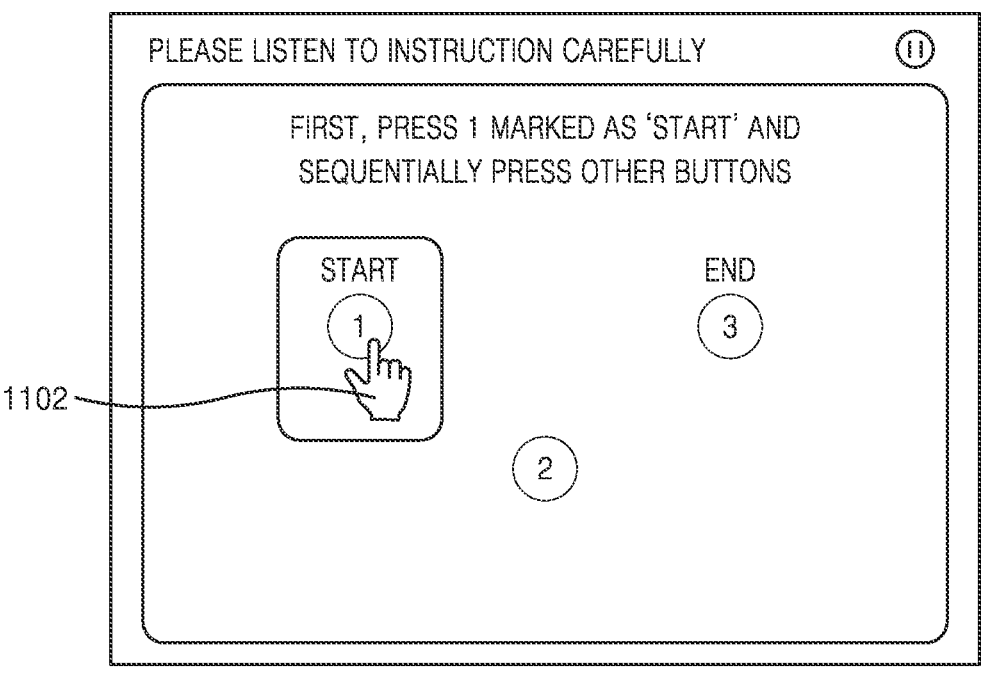
Figure 11D:
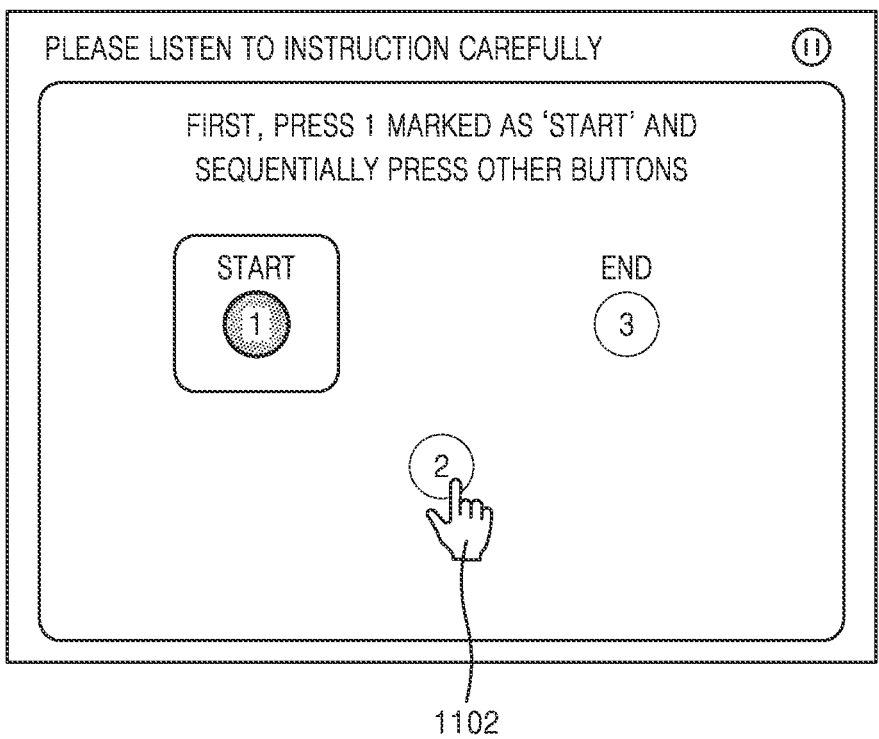
Figure 11E:
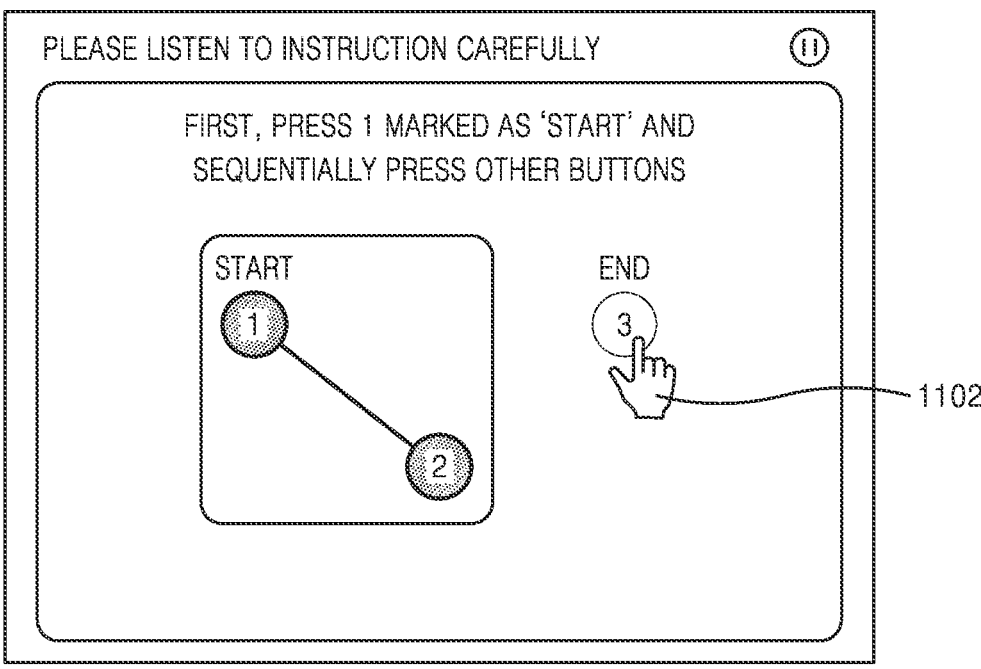
Figure 11F:
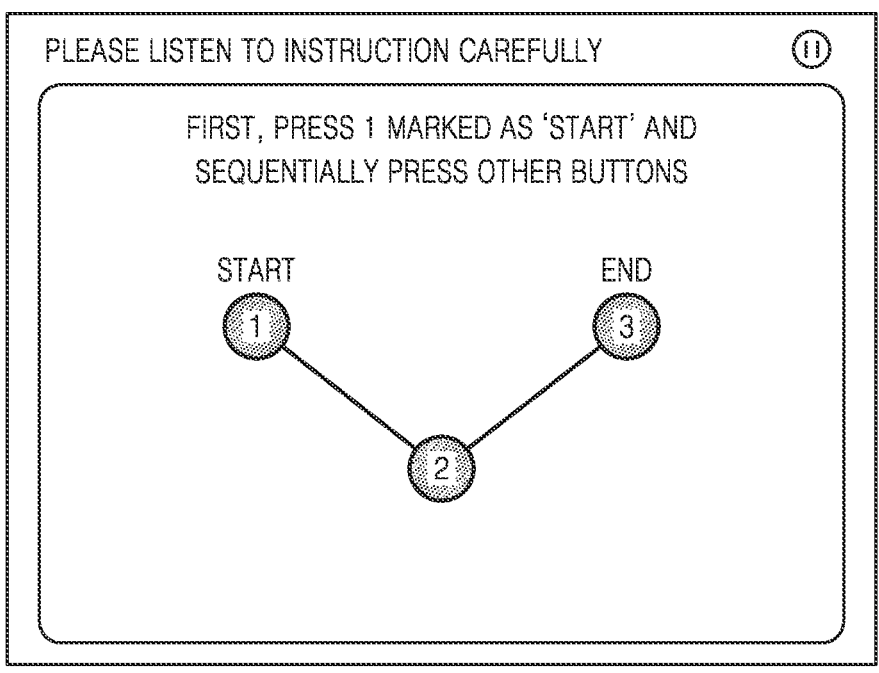
Figure 11G:
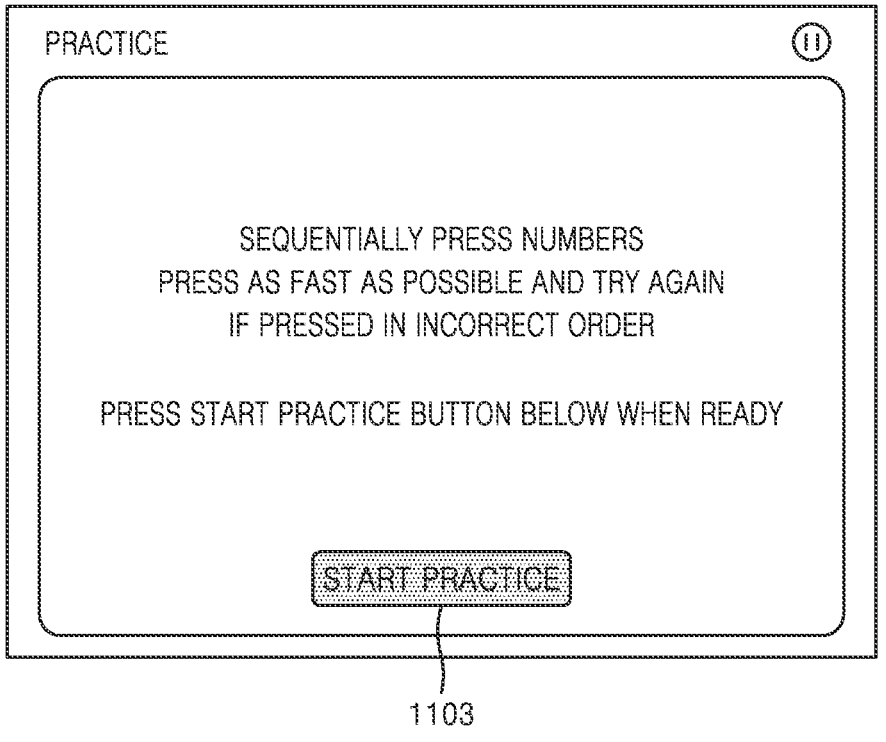
Figure 11H:
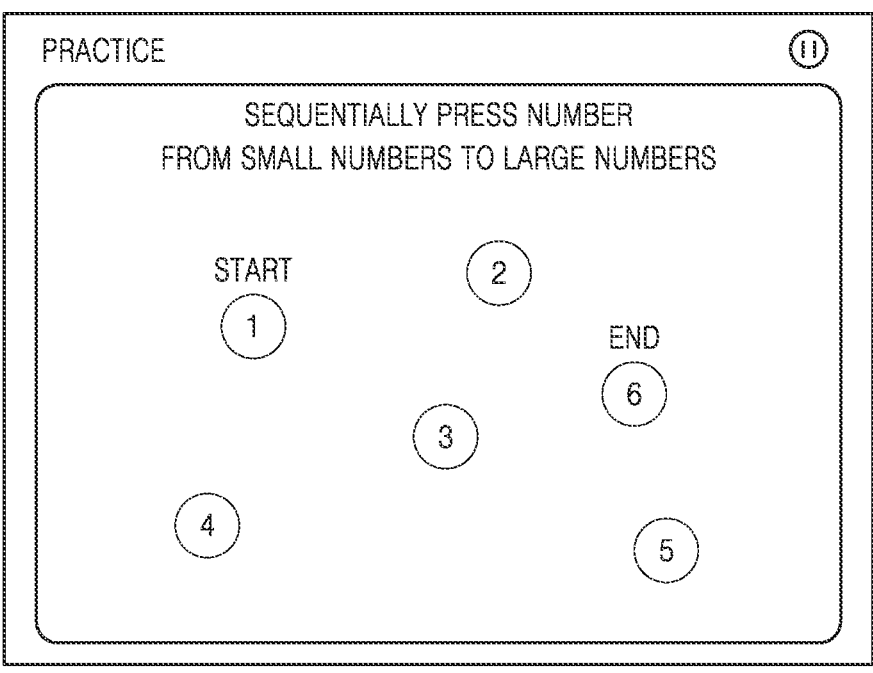
Figure 11I:
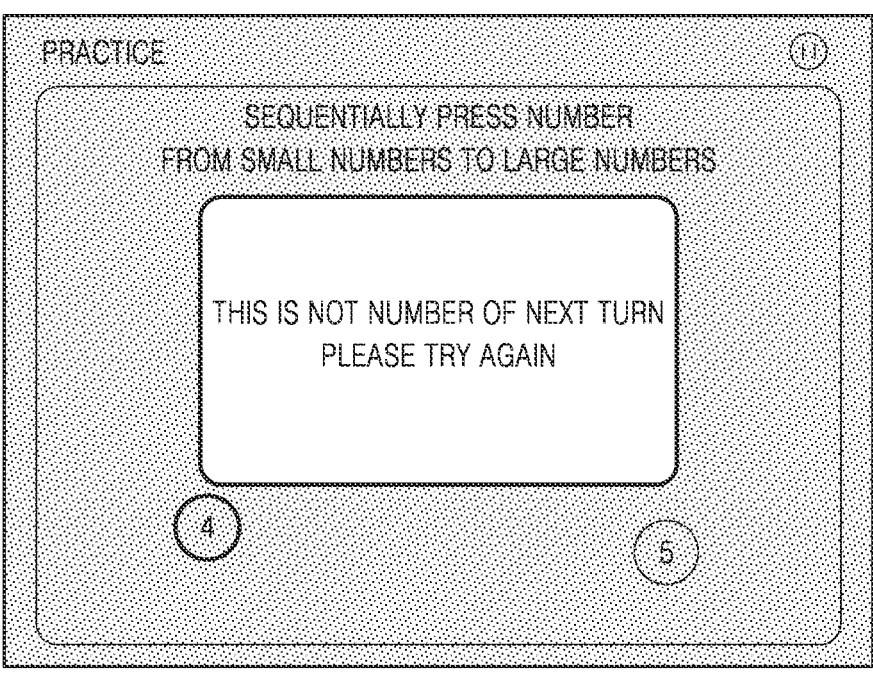
Figure 11J:
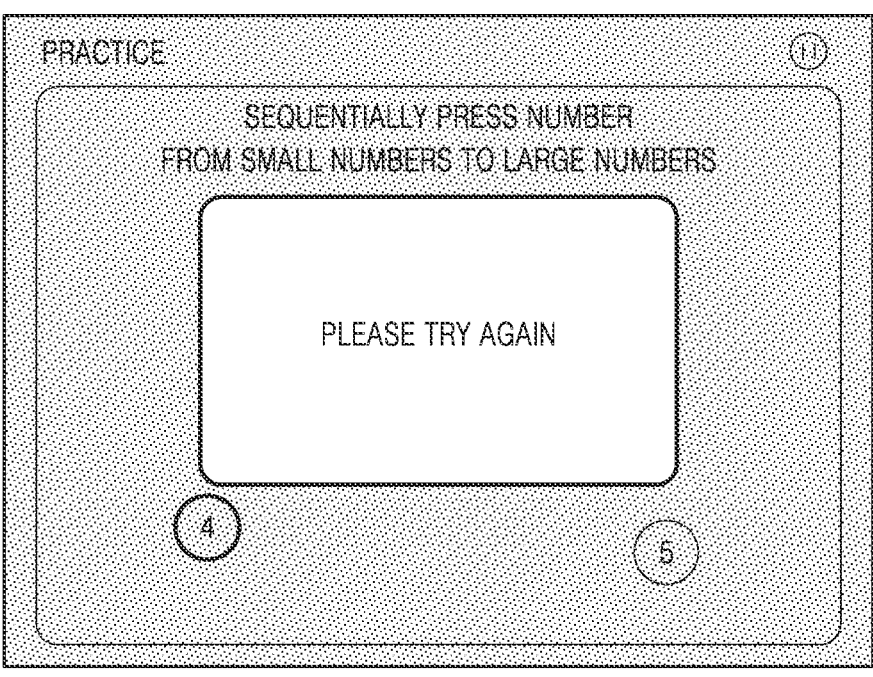
Figure 11K:
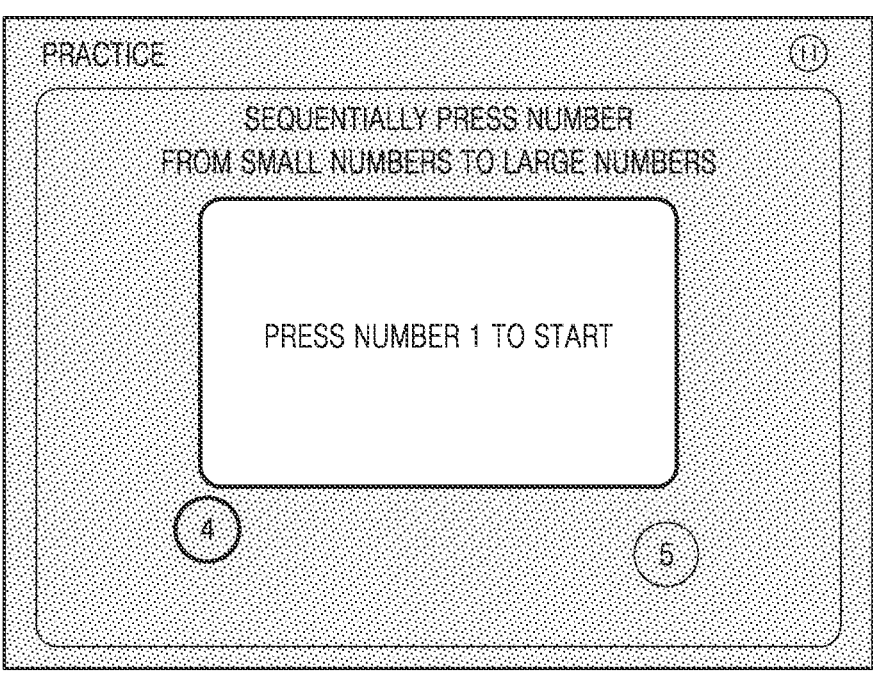
Figure 11L:
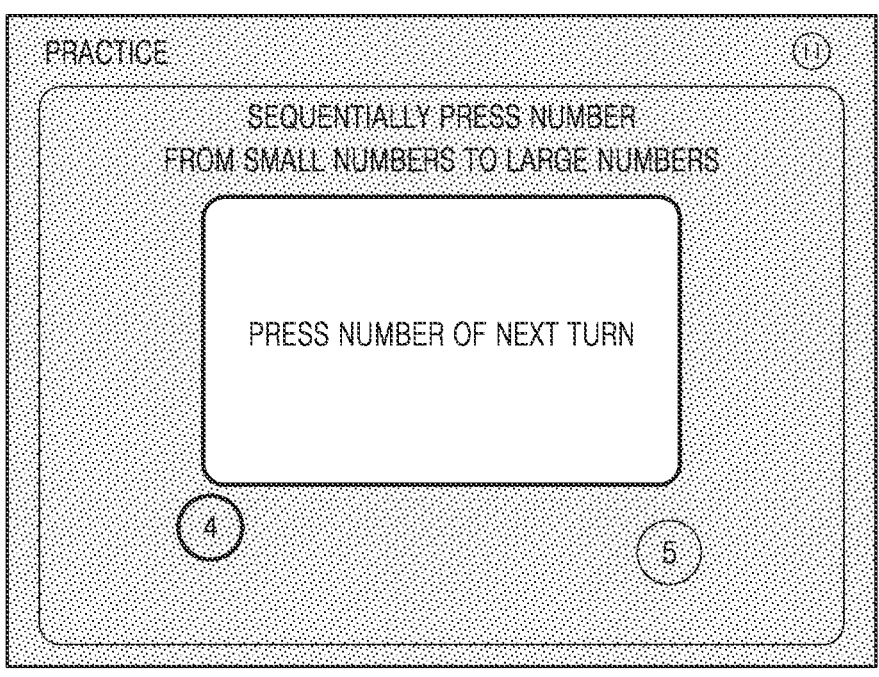
Figure 11M:
Figure 11N:
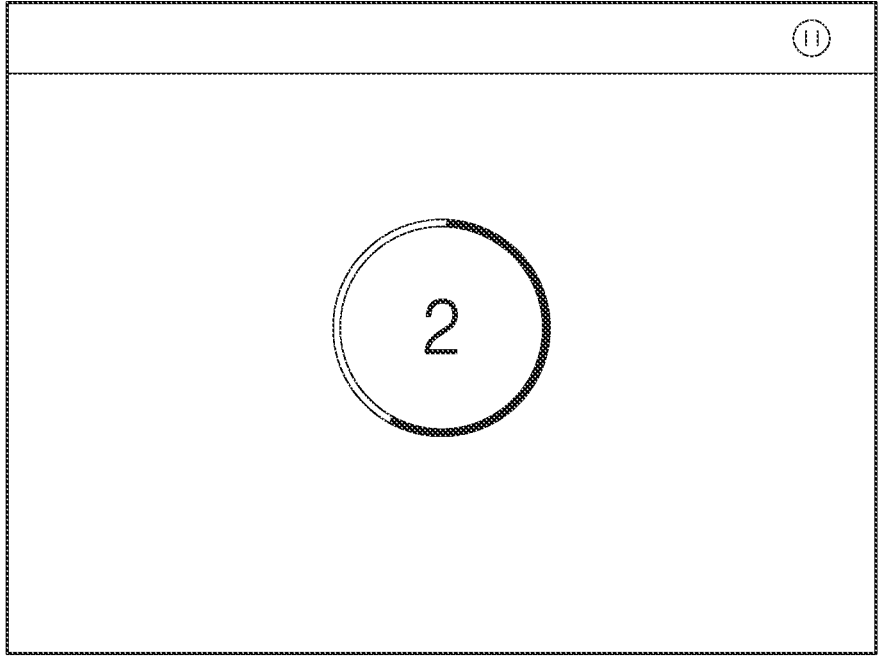
Figure 110:
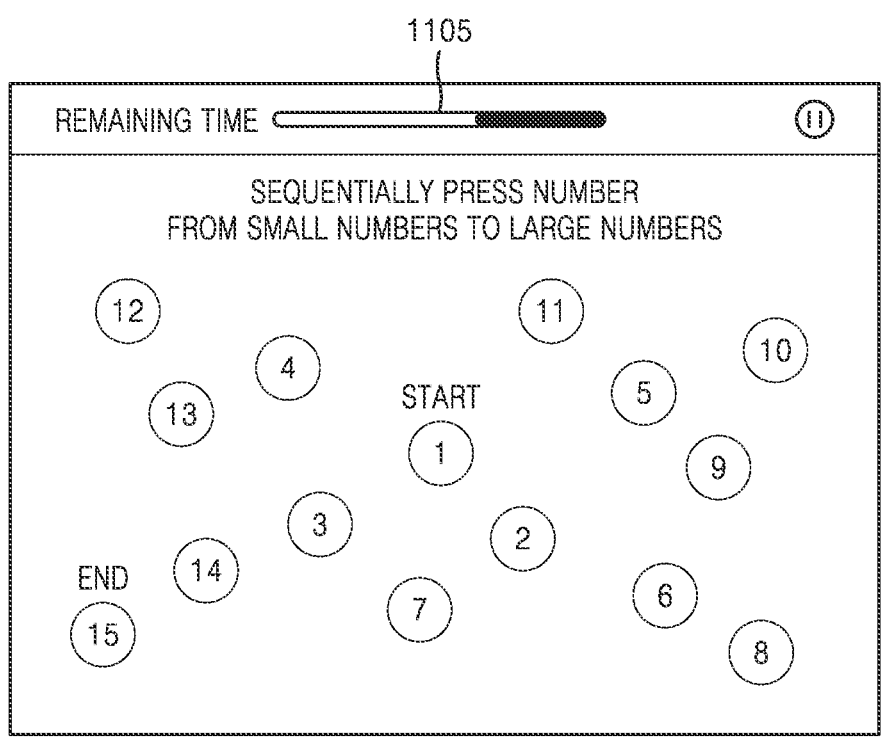
Figure 11P:
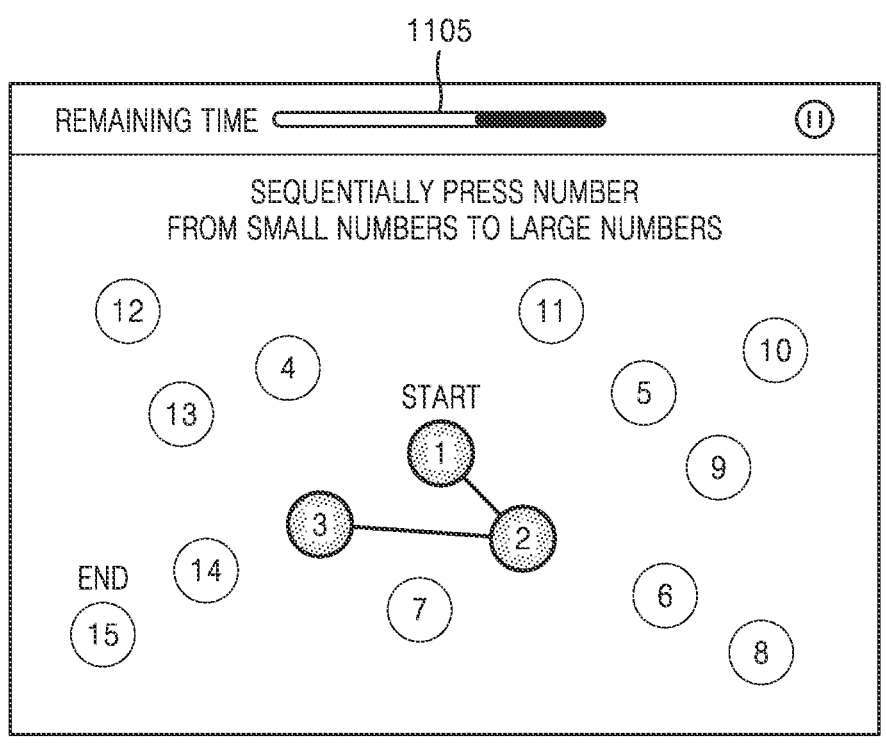
Figure 11Q:
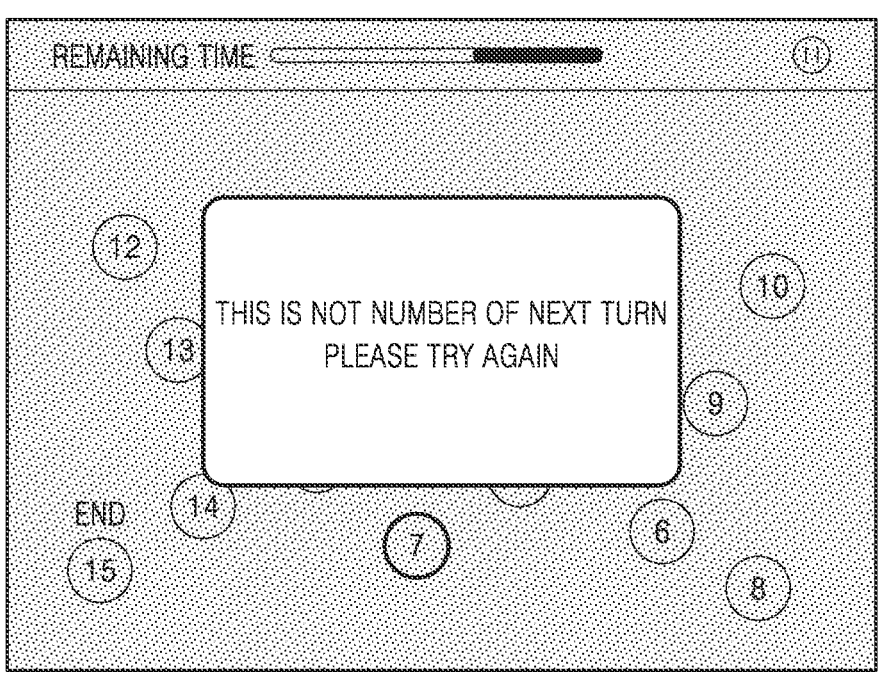
Figure 11R:
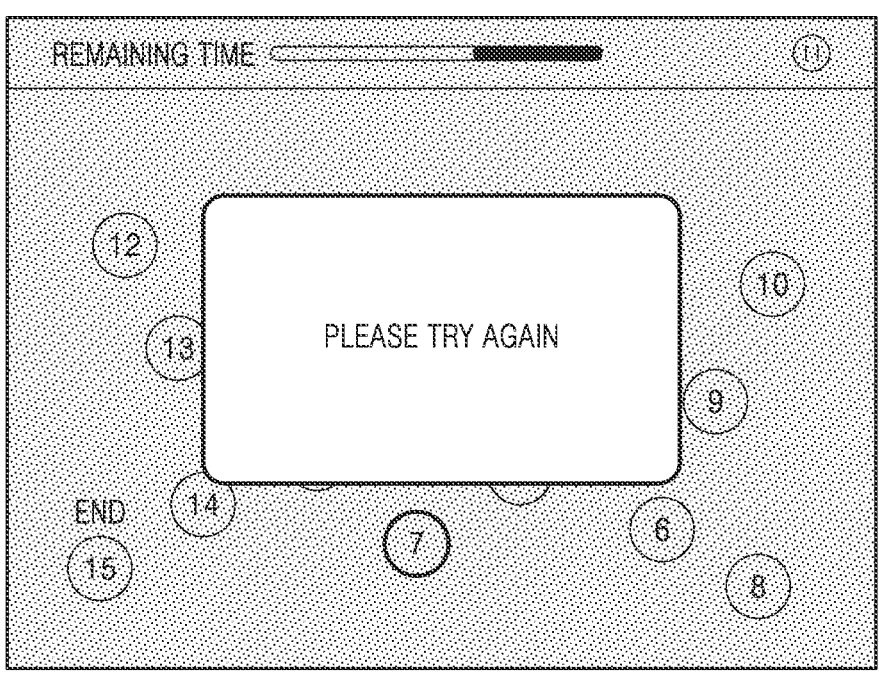
Figure 11S:
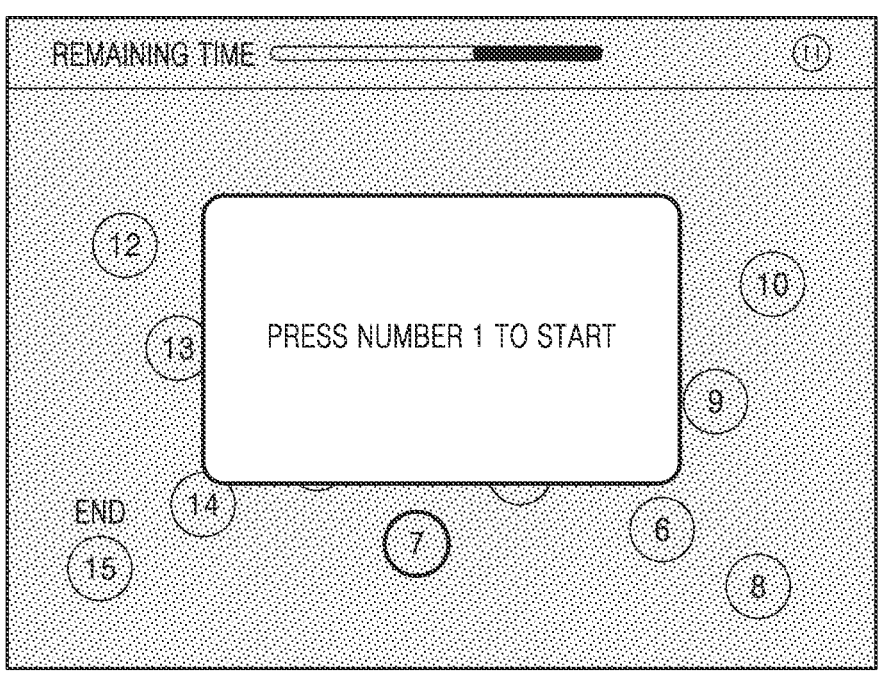
Figure 11T:
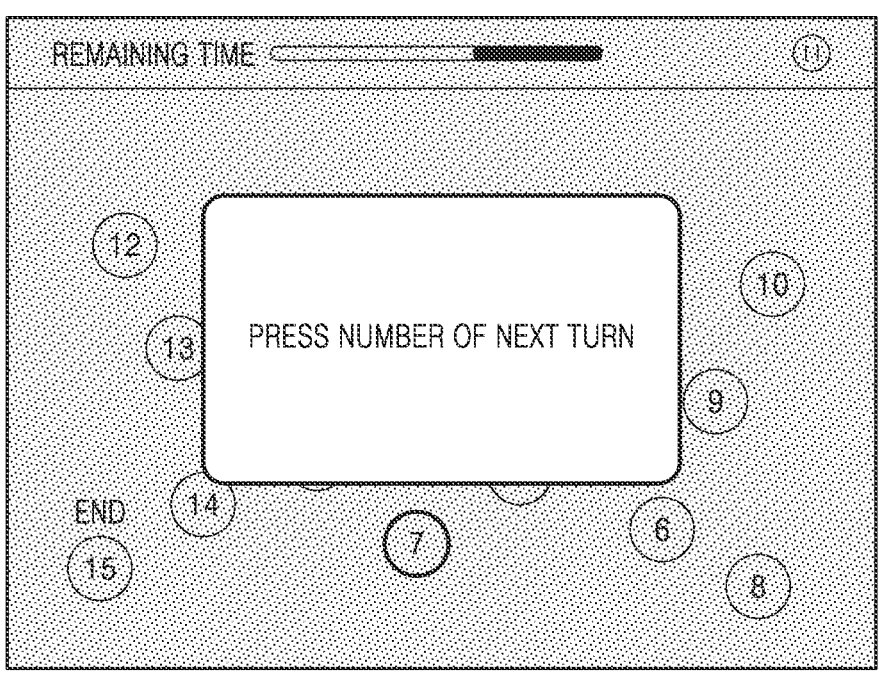
Figure 11U:
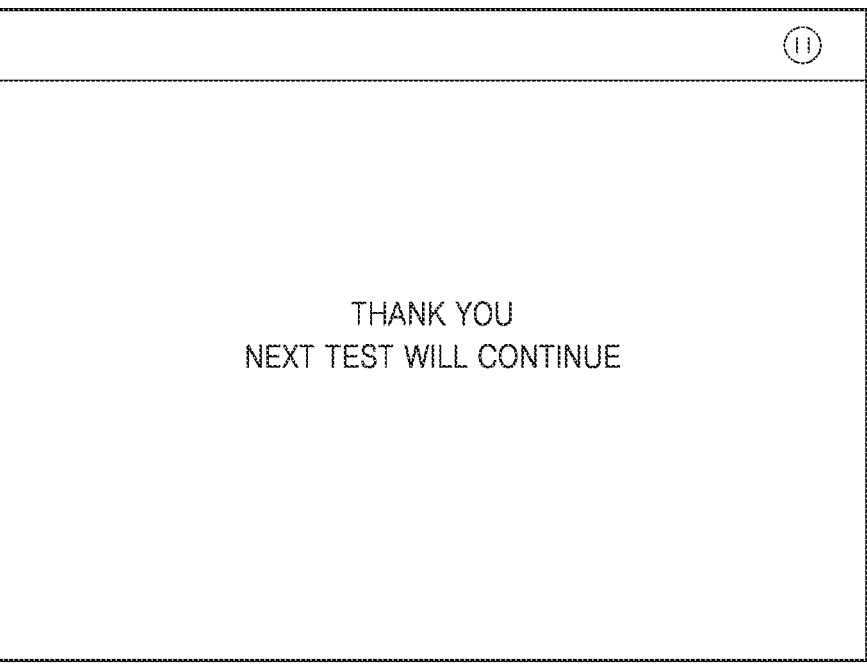

FIGS. 11A through 11U illustrate examples of screens provided to the user terminal 200 to perform the (7-1)th test process.

FIG. 11A illustrates a start screen of the (7-1)th test process. When an input of the start button 1101 is received, a next screen may be displayed and an instruction screen may be displayed.

FIGS. 11B to 11F illustrate instruction screens for the (7-1)th test process. FIGS. 11B to 11D may be displayed all at once or sequentially, and may be switched to a next screen when a predetermined time is elapsed. In FIG. 11B, arbitrary numbers may be displayed on a screen. In FIG. 11B, a phrase 'start' may be displayed on any one of the arbitrary numbers on the screen. Also, a phrase 'end' may be displayed on the last number from among the arbitrary numbers. In FIGS. 11C to 11F, an instruction to select the number 1 marked as start and select next numbers in ascending order may be displayed. Also, in FIGS. 11C to 11F, when a hand image 1102 sequentially touches numbers 1, 2, and 3, colors of touched numbers may be changed. Also, numbers that have been touched may be displayed so as to be connected to one another by line segments.

FIG. 11G illustrates a screen indicating a start of a practice test process ((7-1)th practice test process) for the (7-1)th test process. When a practice start button 1103 is input, a next screen may be displayed.

FIG. 11H illustrates a screen for performing the (7-1)th practice test process. On the screen of FIG. 11H, for example, a (7-1)th practice instruction to choose numbers in ascending order and arbitrary numbers may be displayed. A number to be selected first from among the arbitrary numbers may be marked with a phrase 'start'. Also, a number to be selected last from among the arbitrary numbers may be marked with a phrase 'end'.

FIG. 11I illustrates a screen provided when an incorrect practice answer is initially given, and FIG. 11J illustrates a screen provided when two or more consecutive incorrect practice answers are given. In FIGS. 11I and 11J, an instruction to choose a number again may be displayed.

FIG. 11K illustrates a screen presented as a predetermined time (e.g., 10 seconds) is elapsed without a choice of any number. In FIG. 11K, an instruction to select a number and start a test may be displayed.

FIG. 11L illustrates a screen displayed as a predetermined time (e.g., 20 seconds) is elapsed when a next number is not chosen after one or more numbers are chosen. In FIG. 11L, an instruction to choose a next number may be displayed.

FIG. 11M illustrates a screen on which an instruction to terminate the (7-1)th practice test process and choose a test start button 1104 to execute the (7-1)th test process is displayed.

FIG. 11N illustrates a countdown for executing the (7-1)th test process. In FIG. 11N, counts 3, 2, and 1 and a start screen may be displayed before the (7-1)th test process starts.

FIGS. 11O and 11P illustrate a (7-1)th test process execution screen. On the screen of FIGS. 11O and 11P, for example, a (7-1)th instruction to choose numbers in ascending order and arbitrary numbers may be displayed. A number to be selected first from among the arbitrary numbers may be marked with a phrase 'start'. Also, a number to be selected last from among the arbitrary numbers may be marked with a phrase 'end'. In the screen of FIG. 11P, the color of a number that has been touched may be changed. In the screen of FIG. 11P, numbers that have been touched may be displayed so as to be connected to one another by line segments. In FIGS. 11O and 11P, a user may choose a number while viewing a progress bar 1105 in which the elapsed time is counted.

FIG. 11Q illustrates a screen provided when an incorrect answer is initially given, and FIG. 11R illustrates a screen provided when two or more consecutive incorrect answers are given. In FIGS. 11Q and 11R, numbers chosen in a wrong order may be change to a different color (e.g., red). Also, in FIGS. 11Q and 11R, an instruction to choose a number again may be displayed. The elapsed time may continue to be counted even when an instruction is displayed.

FIG. 11S illustrates a screen presented as a predetermined time (e.g., 10 seconds) is elapsed without a choice of any number. In FIG. 11S, an instruction to select a number and start a test may be displayed.

FIG. 11T illustrates a screen displayed as a predetermined time (e.g., 20 seconds) is elapsed when a next number is not chosen after one or more numbers are chosen. In FIG. 11T, an instruction to choose a next number may be displayed.

FIG. 11U illustrates a screen indicating completion of the performing of the (7-1)th test process and a start of a next test process.

Figure 12A:
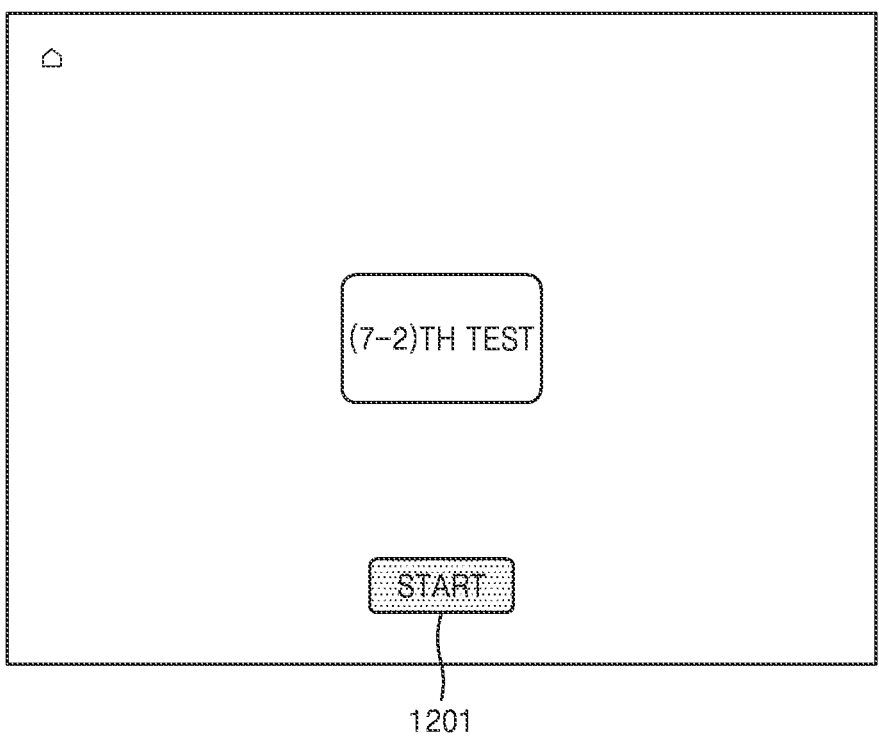
Figure 12B:
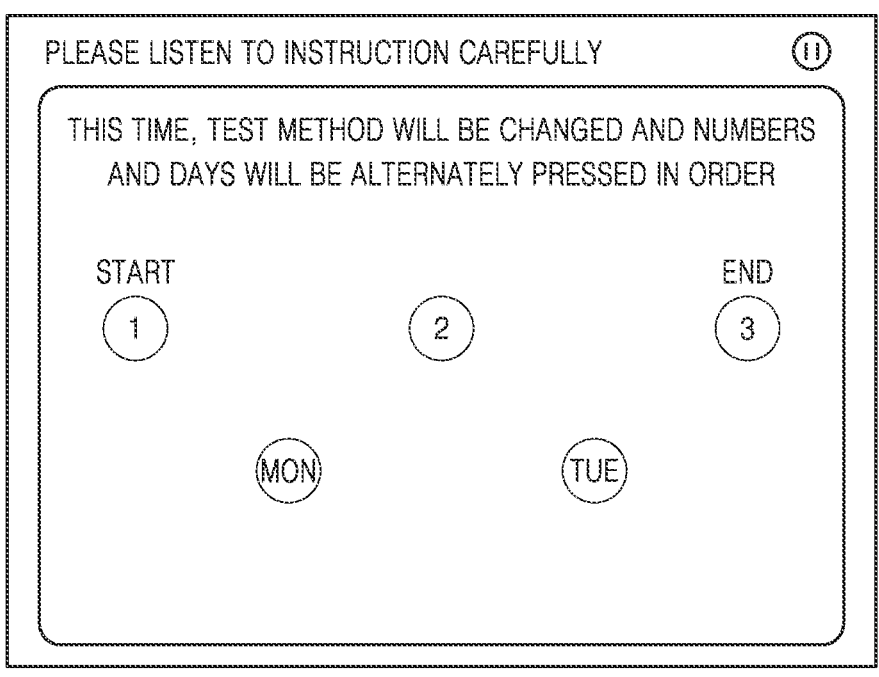
Figure 12C:
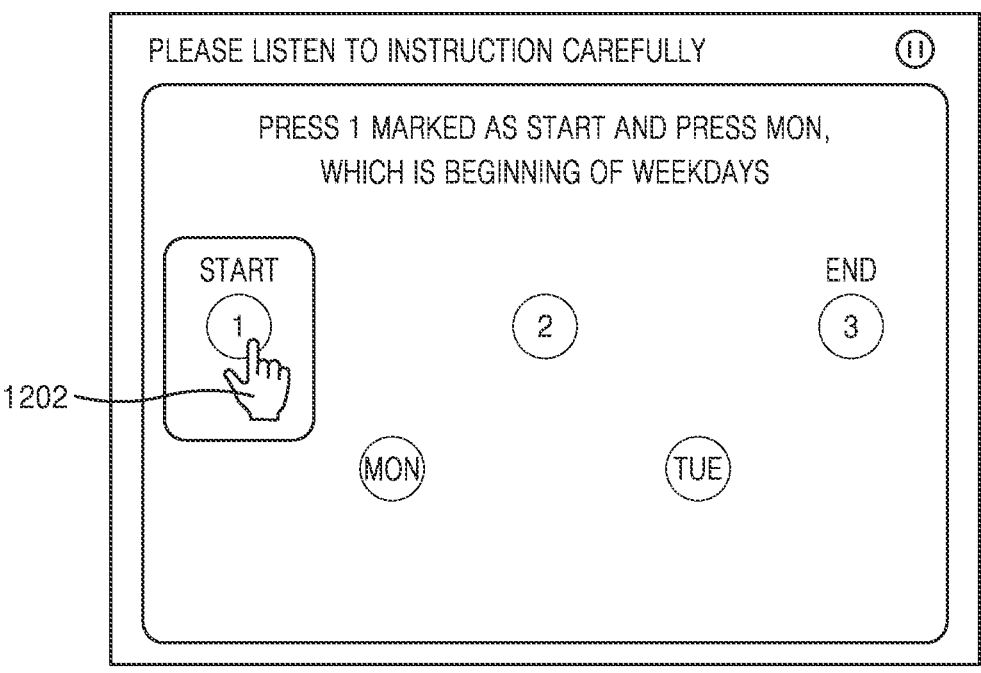
Figure 12D:
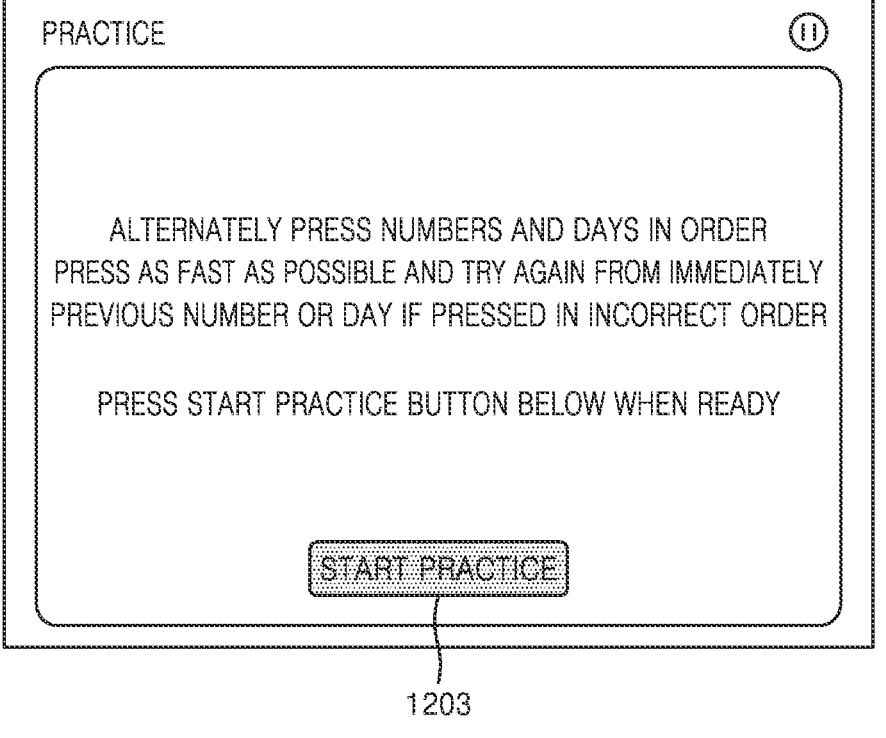
Figure 12E:
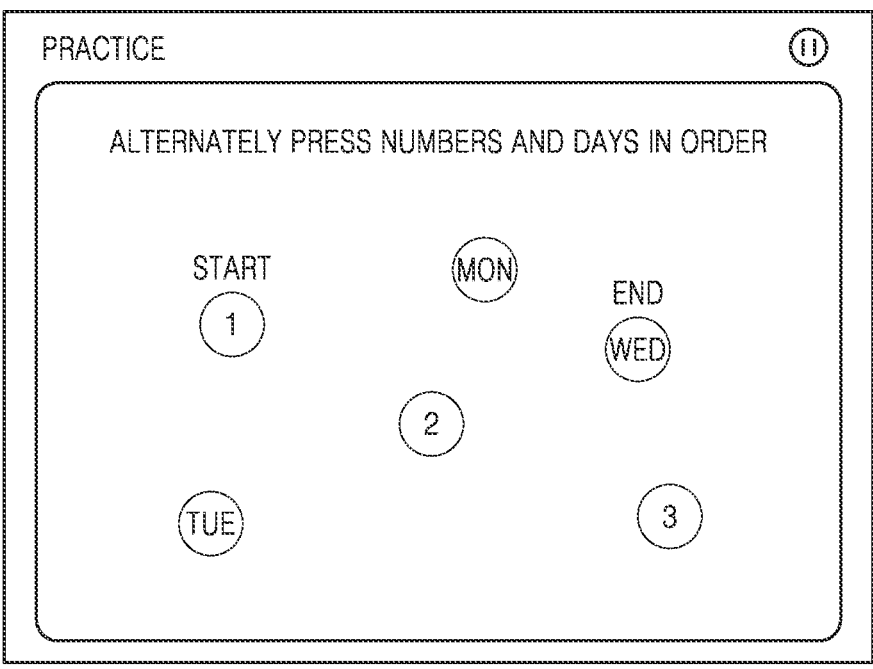
Figure 12F:
Figure 12G:
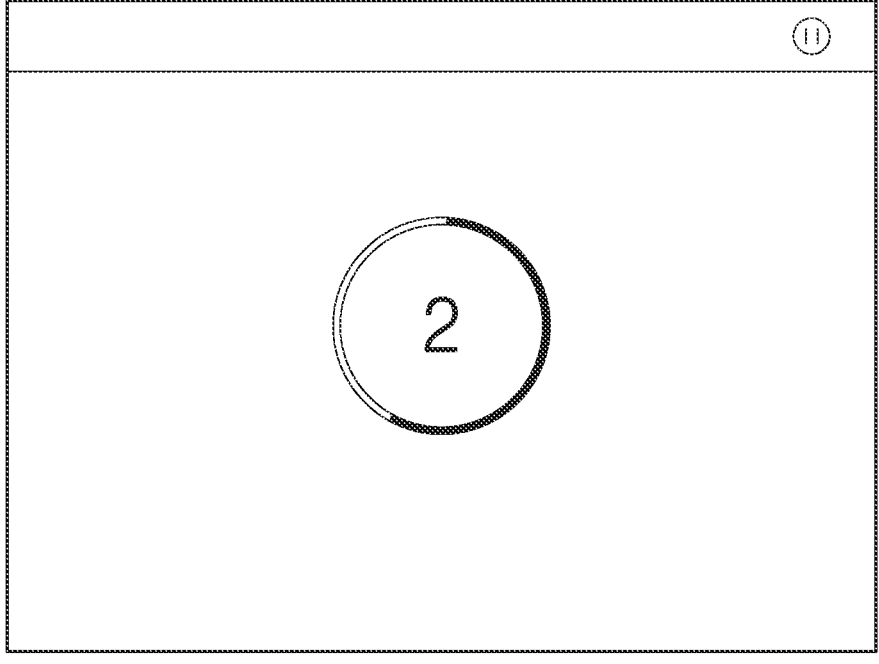
Figure 12H:
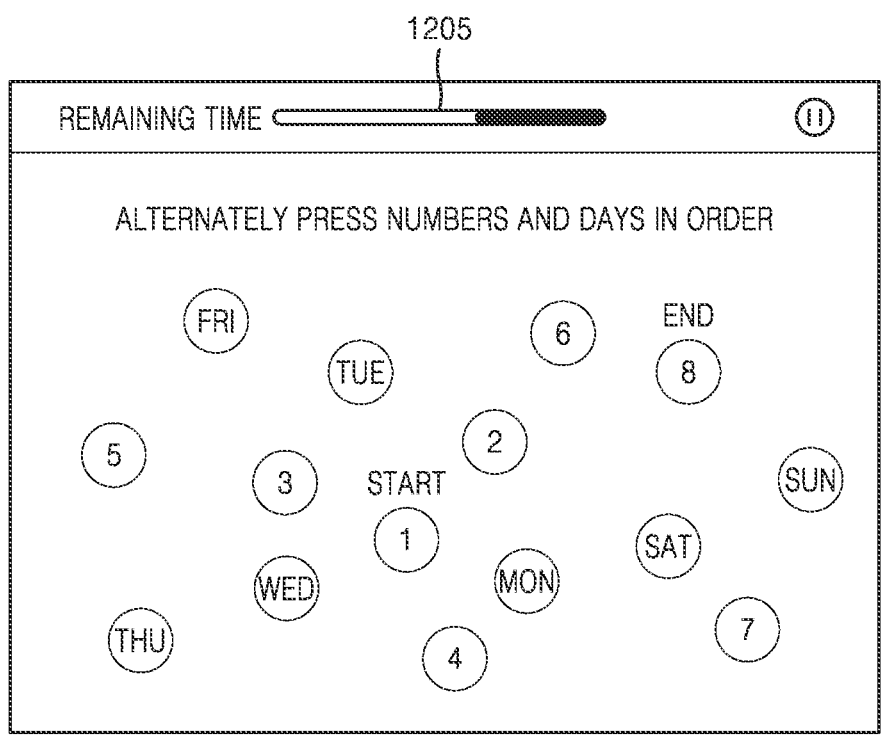
Figure 12I:
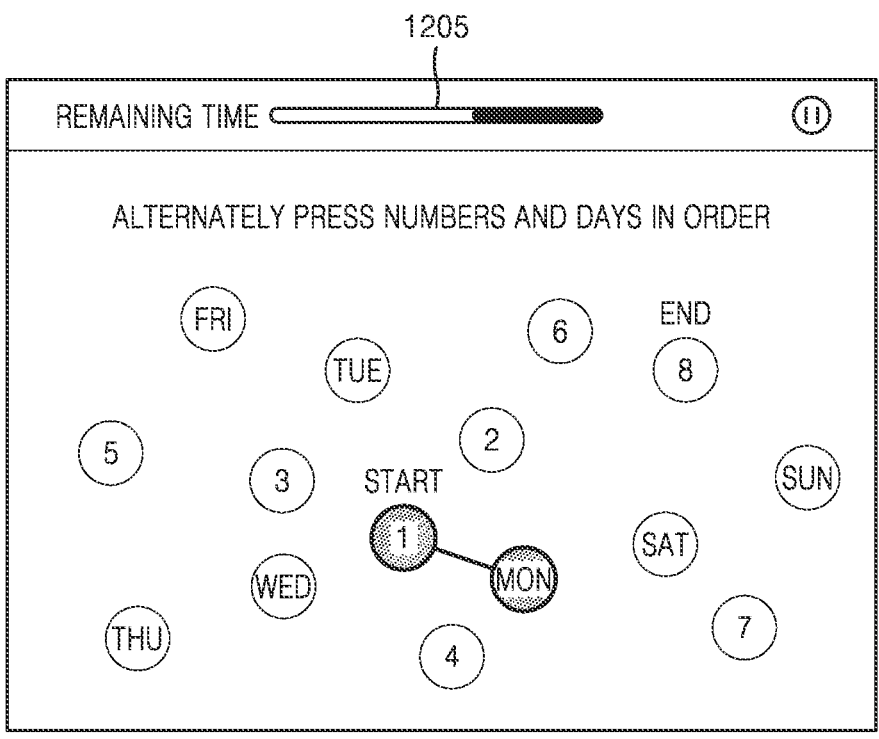
Figure 12J:
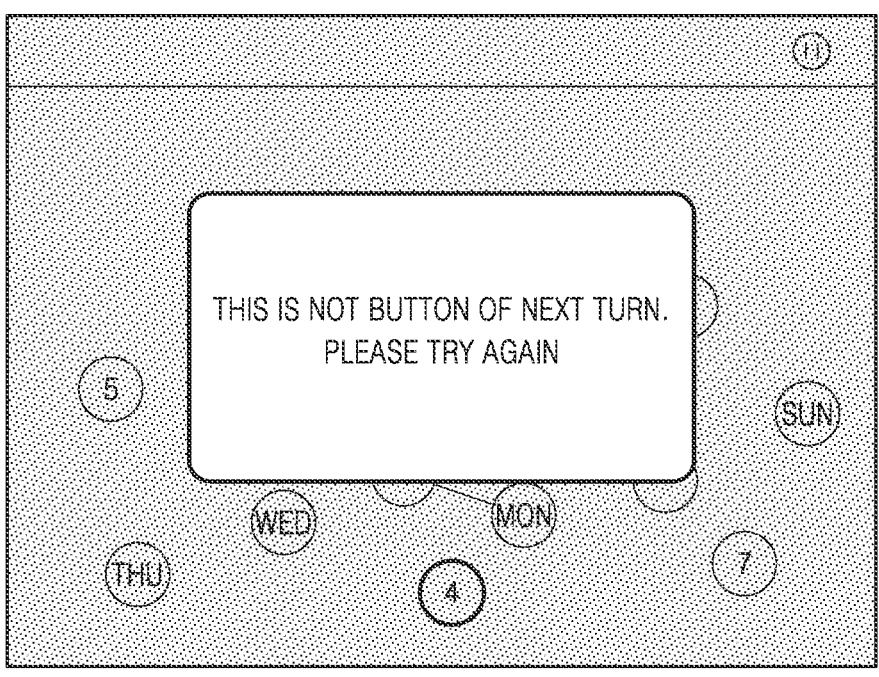
Figure 12K:
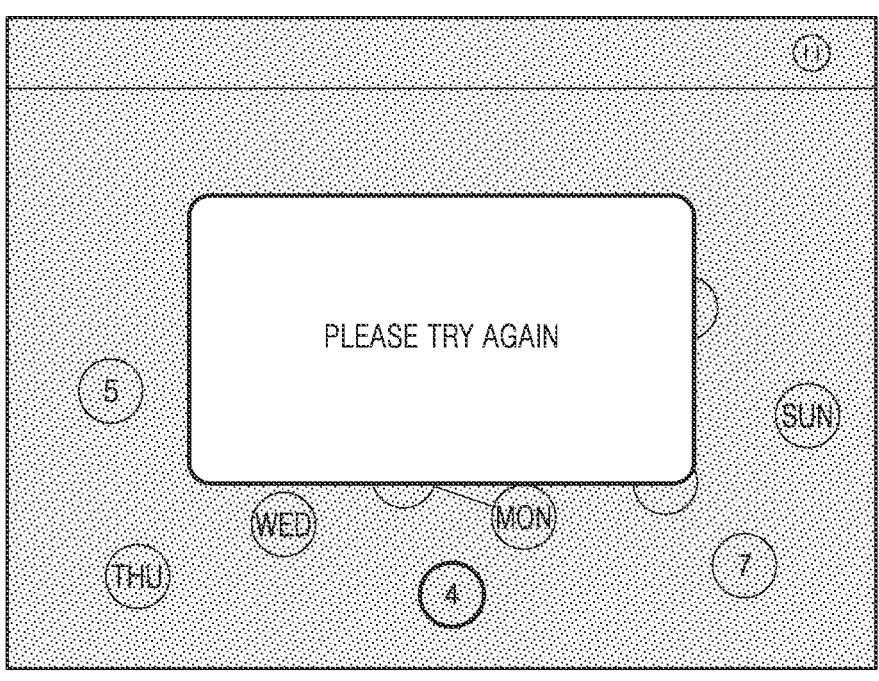
Figure 12L:
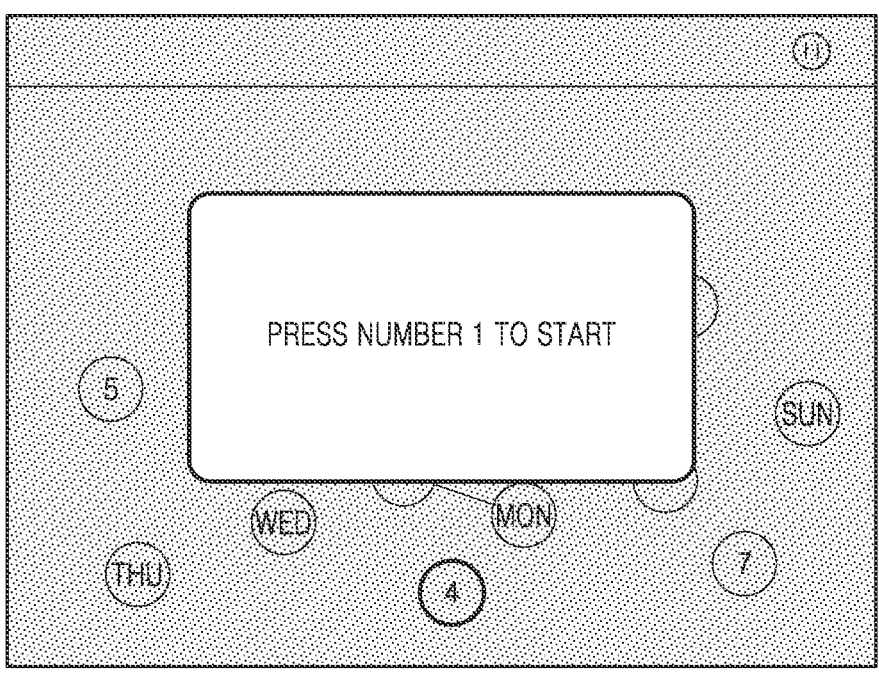
Figure 12M:
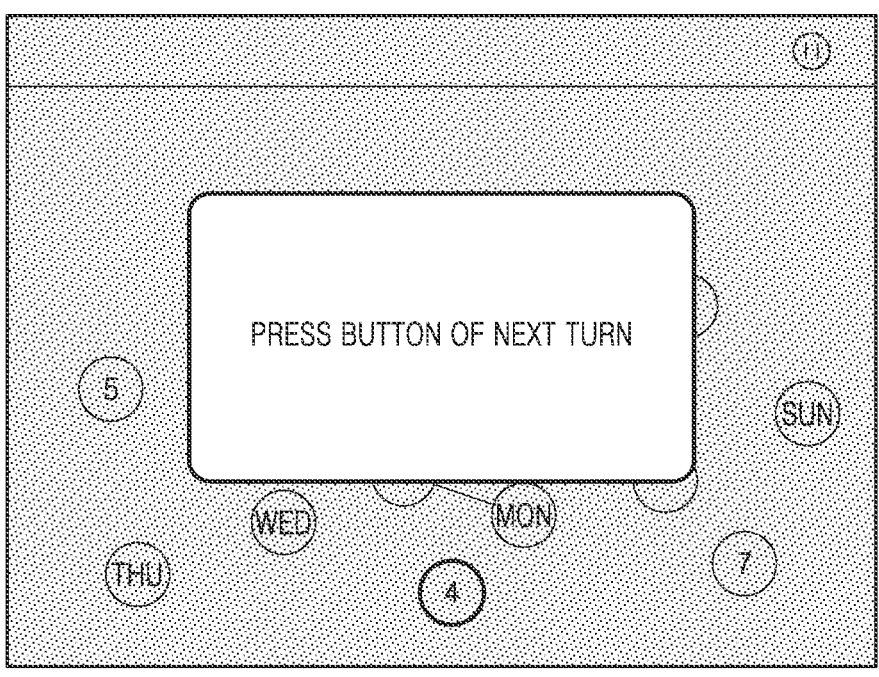
Figure 12N:
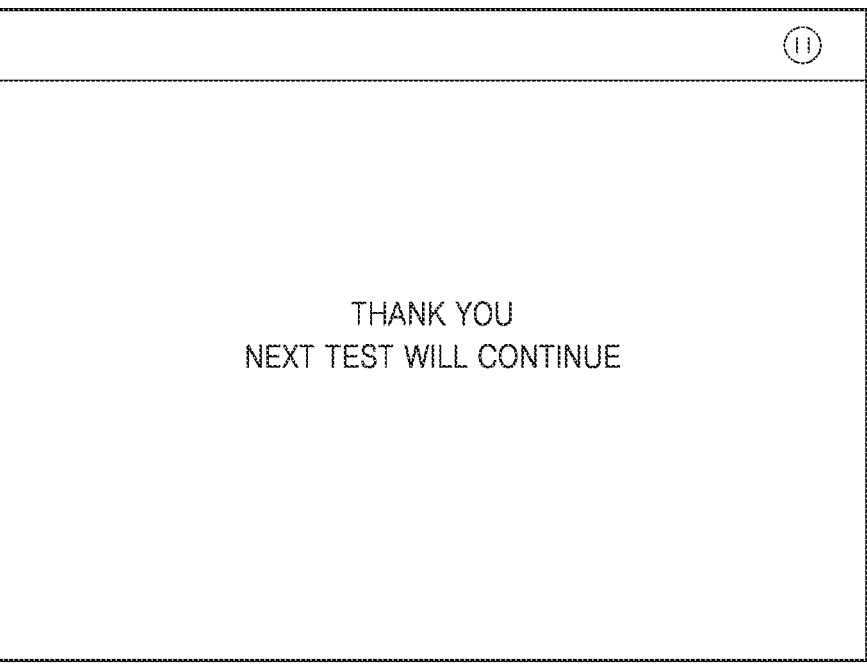

FIGS. 12A through 12N illustrate examples of screens provided to the user terminal 200 to perform the (7-2)th test process.

FIG. 12A illustrates a start screen of the (7-2)th test process. When an input of the start button 1201 is received, a next screen may be displayed and an instruction screen may be displayed.

FIGS. 12B and 12C illustrate instruction screens for the (7-2)th test process. FIGS. 12B and 12C may be displayed all at once or sequentially, and may be switched to a next screen when a predetermined time is elapsed. In FIG. 12B, arbitrary numbers and arbitrary days may be displayed on a screen. In FIG. 12B, an instruction to alternately choose a number and a day may be displayed. A phrase 'start' may be displayed on any one of the arbitrary numbers on the screen. Also, a phrase 'end' may be displayed on the last number from among the arbitrary numbers. In FIG. 12C, an instruction to choose the number 1 marked as start and select Mon, which is the starting day of a week, may be displayed. In FIG. 12C, when a hand image 1202 sequentially touches the number 1, Mon, the number 2, Tue, and the number 3, colors of touched numbers and touched days may be changed. Also, numbers and days that have been touched may be displayed so as to be connected to one another by line segments.

FIG. 12D illustrates a screen indicating a start of a practice test process ((7-2)th practice test process) for the (7-2)th test process. When a practice start button 1203 is input, a next screen may be displayed.

FIG. 12E illustrates a screen for performing the (7-2)th practice test process. On the screen of FIG. 12E, for example, a (7-2)th practice instruction to alternately choose numbers and days and arbitrary numbers and arbitrary days may be displayed. A number to be selected first from among the arbitrary numbers may be marked with a phrase 'start'. Also, a number or a day to be selected last from among the arbitrary numbers or the arbitrary days may be marked with a phrase 'end'. A user may perform a practice test by alternately selecting numbers and days while viewing arbitrary numbers and arbitrary days illustrated in FIG. 12E.

FIG. 12F illustrates a screen on which an instruction to terminate the (7-2)th practice test process and choose a test start button 1204 to execute the (7-2)th test process is displayed.

FIG. 12G illustrates a countdown for executing the (7-2)th test process. In FIG. 12G, counts 3, 2, and 1 and a start screen may be displayed before the (7-2)th test process starts.

FIGS. 12H and 12I illustrate a (7-2)th test process execution screen. On the screen of FIGS. 12H and 12I for example, a (7-2)th instruction to alternately choose numbers and days and arbitrary numbers and arbitrary days may be displayed. A number to be selected first from among the arbitrary numbers may be marked with a phrase 'start'. Also, a number or a day to be selected last from among the arbitrary numbers or the arbitrary days may be marked with a phrase 'end'. In the screen of FIG. 12I, the color of a number or a day that has been touched may be changed. In the screen of FIG. 12I, numbers and days that have been touched may be displayed so as to be connected to one another by line segments. In FIGS. 12H and 12I, a user may alternately choose a number and a day while viewing a progress bar 1205 in which the elapsed time is counted.

FIG. 12J illustrates a screen provided when an incorrect answer is initially given, and FIG. 12K illustrates a screen provided when two or more consecutive incorrect answers are given. Also, in FIGS. 12J and 12K, an instruction to choose at least one of a number and a day again may be displayed. The elapsed time may continue to be counted even when an instruction is displayed.

FIG. 12L illustrates a screen presented as a predetermined time (e.g., 10 seconds) is elapsed without a choice of any number. In FIG. 12L, an instruction to select a number and start a test may be displayed.

FIG. 12M illustrates a screen displayed as a predetermined time (e.g., 20 seconds) is elapsed when a next number or a next day is not chosen after one or more numbers or one or more days are chosen. In FIG. 12M, an instruction to choose a next number or a next day may be displayed.

FIG. 12N illustrates a screen indicating completion of the performing of the seventh test process and a start of a next test process.

Referring back to FIG. 3, the first processing unit 152 may perform the eighth test process including the (8-1)th test process and the (8-2)th test process. According to the present embodiment, the first processing unit 152 may perform the eighth test process a plurality of times.

When the (8-1)th test process is performed, the first processing unit 152 may illustrate a plurality of first object presented images including names of first objects and shapes of the first objects, and provide, to the user terminal 200, the (8-1)th instruction, in which it is instructed to choose the plurality of first object presented images in a descending order or an ascending order by determining sizes of the first objects.

The first processing unit 152 may receive, from the user terminal 200, a result of choosing the first object presented images in the descending order or the ascending order, in response to the (8-1)th instruction, and calculate the (8-1)th test score by comparing the result with a correct answer. According to the present embodiment, the (8-1)th test score may be calculated to be high when there are many results determined to be correct answers compared to the total number of times the (8-1)th test processes have been performed.

According to the present embodiment, before the (8-1)th test process is performed, the first processing unit 152 may provide, in at least one of a text and an instruction screen, a method of performing the (8-1)th test process to the user terminal 200.

The first processing unit 152 may perform the (8-2)th test process after the performing of the (8-1)th test process is completed.

When the (8-2)th test process is performed, the first processing unit 152 may illustrate a plurality of second object presented images including shapes of second objects, and provide, to the user terminal 200, the (8-2)th instruction, in which it is instructed to choose the plurality of second object presented images in a descending order or an ascending order by determining weights of the second objects.

The first processing unit 152 may receive, from the user terminal 200, a result of choosing the second object presented images in the descending order or the ascending order, in response to the (8-2)th instruction, and calculate the (8-2)th test score by comparing the result with a correct answer.

According to the present embodiment, before the (8-2)th test process is performed, the first processing unit 152 may provide, in at least one of a text and an instruction screen, a method of performing the (8-2)th test process to the user terminal 200. According to the present embodiment, the (8-2)th test score may be calculated to be high when there are many results determined to be correct answers compared to the total number of times the (8-2)th test processes have been performed.

According to a selective embodiment, the first processing unit 152 may calculate the eighth test score by adding the (8-1)th test score and the (8-2)th test score. Alternatively, the first processing unit 152 may not add the (8-1)th test score and the (8-2)th test score, but may use the (8-1)th test score and the (8-2)th test score each to evaluate cognitive function decline. According to the present embodiment, it may be evaluated that semantic memory is good when the eighth test score is higher than the eighth criterion cut-off score, and is declined when the eighth test score is lower than the eighth criterion cut-off score.

FIGS. 13A through 13I illustrate examples of screens provided to the user terminal 200 to perform the eighth test process. FIGS. 13A through 13E illustrate examples of screens for describing the (8-1)th test process and FIGS. 13F through 13I illustrate examples of screens for describing the (8-2)th test process.

Figure 13A:
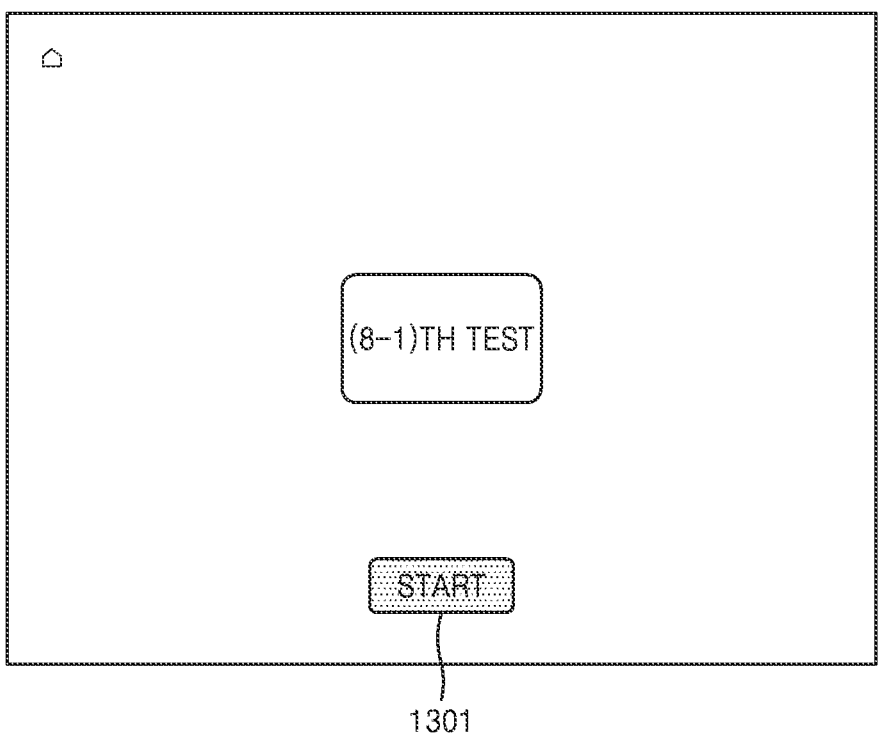

FIG. 13A illustrates a start screen of the (8-1)th test process. When an input of a start button 1301 is received, a screen for the (8-1)th test process may be displayed.

Figure 13B:
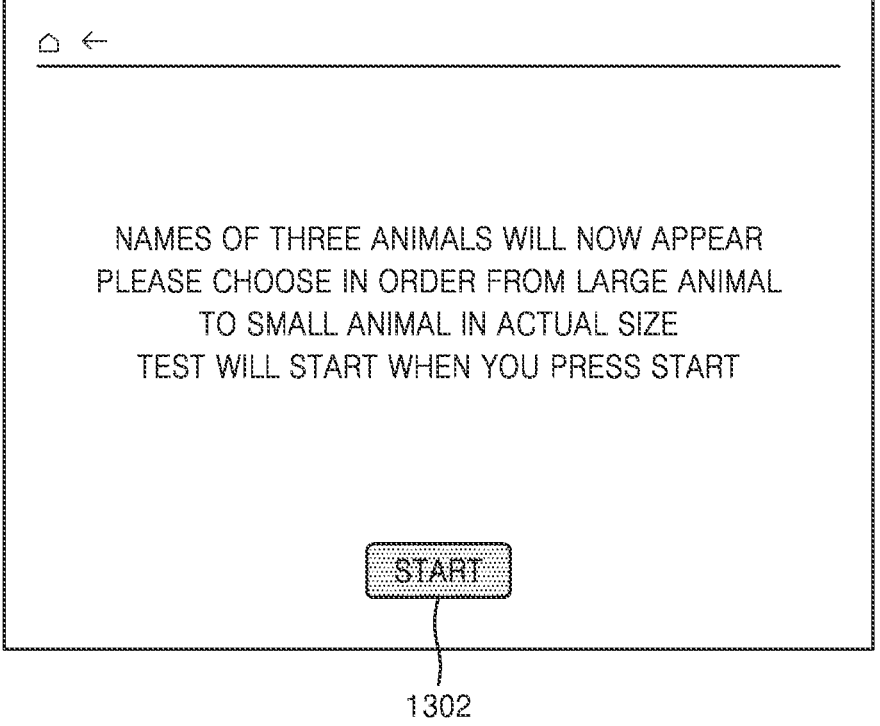

FIG. 13B illustrates a screen providing, in a text, a method of performing the (8-1)th test process, and indicating a start of the (8-1)th test process. When a start button 1302 is input, a next screen may be displayed.

Figure 13C:
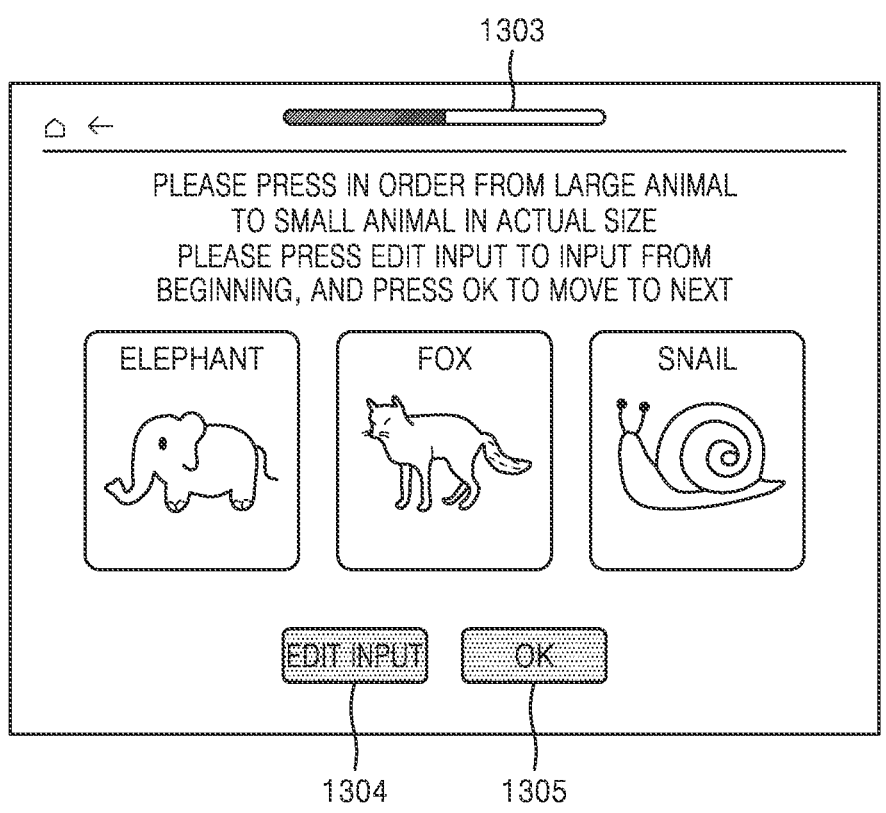

FIG. 13C illustrates a screen for performing the (8-1)th test process. The user may check the (8-1)th instruction, and then choose a plurality of first object presented images according to size while looking at a progress bar 1303. The user may re-choose by inputting an edit input button 1304 when the choice needs to be edited. When the user inputs an OK button 1305 after completing the choice, a next screen may be displayed.

Figure 13D:
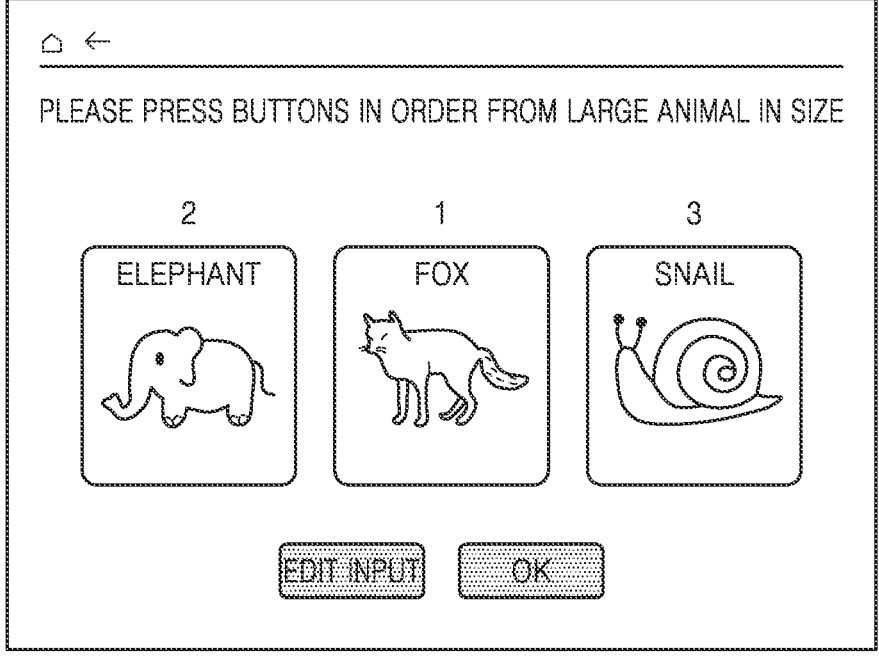

FIG. 13D illustrates a screen showing a result of performing the (8-1)th test process. Numbers indicating the order the user chose the first object presented images may be output on the first object presented images.

Figure 13E:
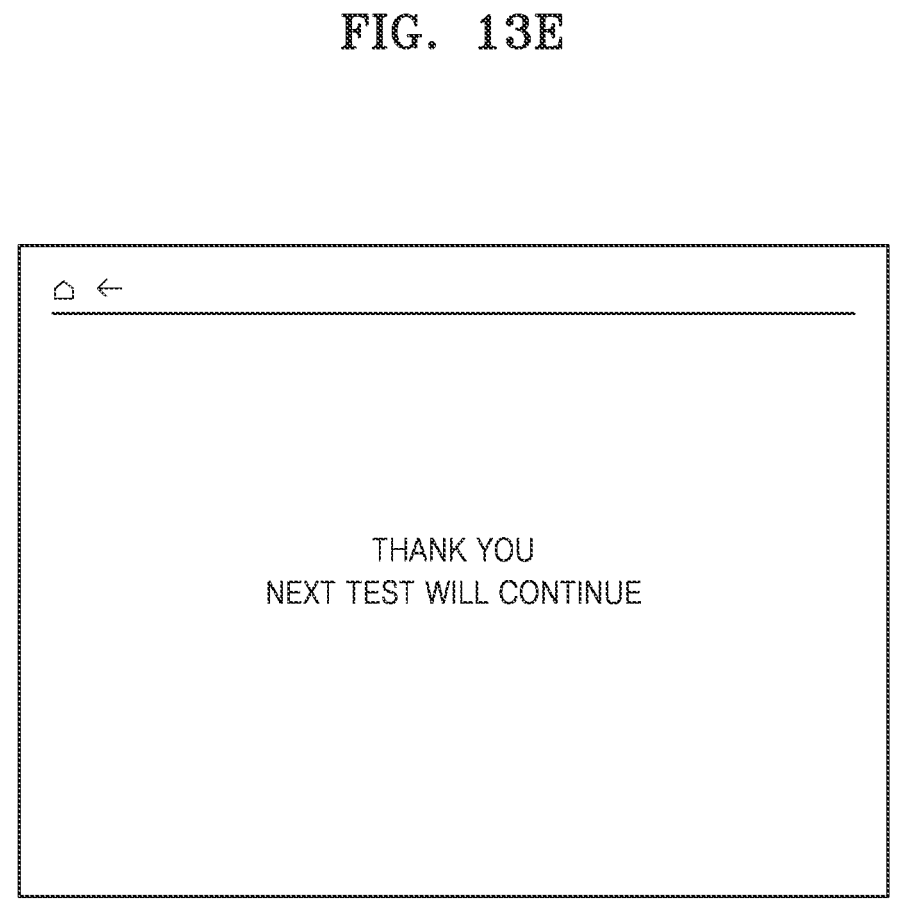

FIG. 13E illustrates a screen indicating completion of the performing of the (8-1)th test process and a start of a next test process.

Figure 13F:
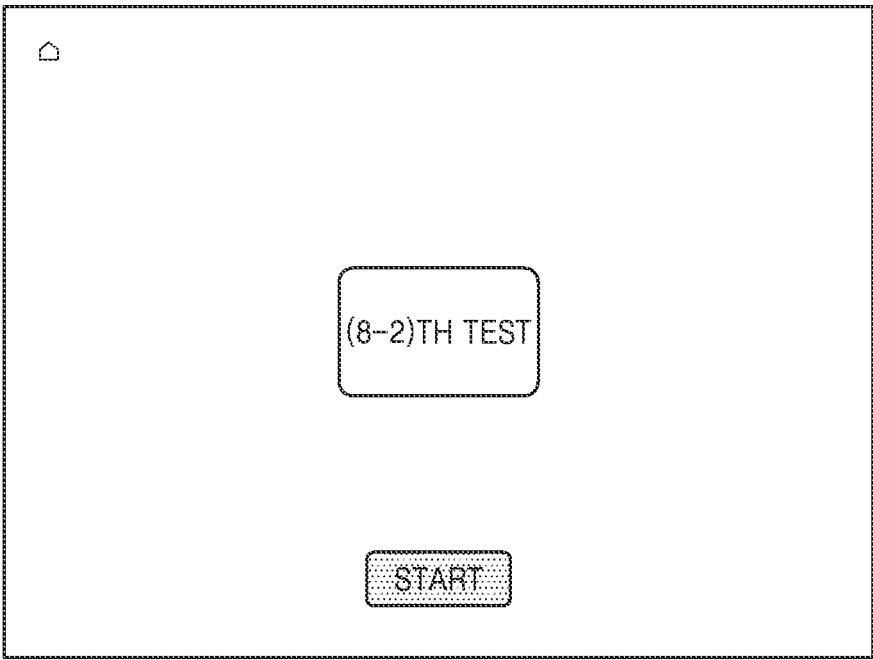

FIG. 13F illustrates a start screen of the (8-2)th test process.

Figure 13G:
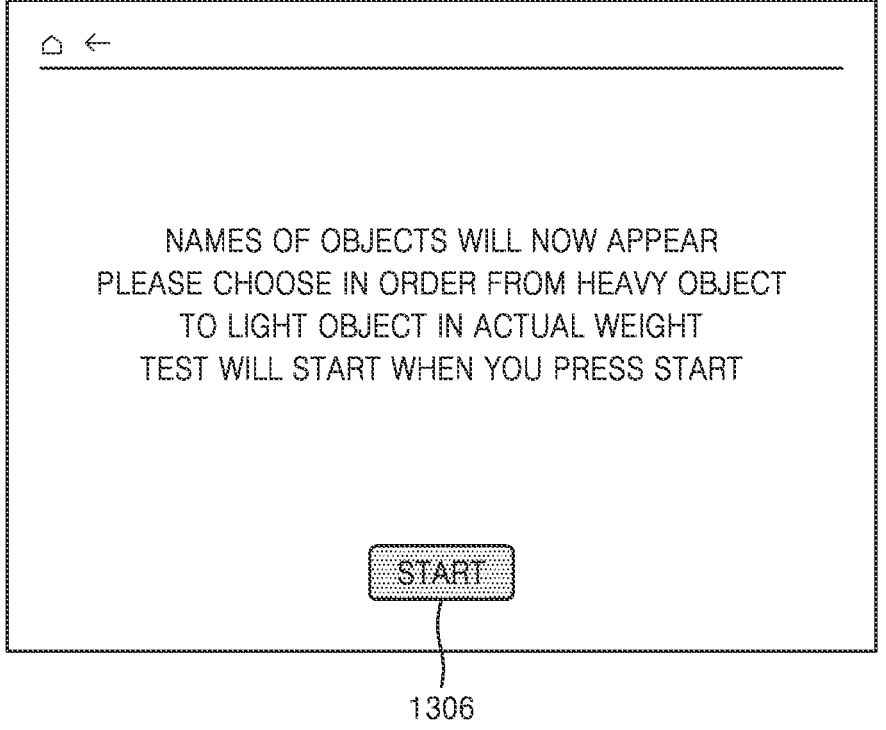

FIG. 13G illustrates a screen providing, in a text, a method of performing the (8-2)th test process, and indicating a start of the (8-2)th test process. When a start button 1306 is input, a next screen may be displayed.

Figure 13H:
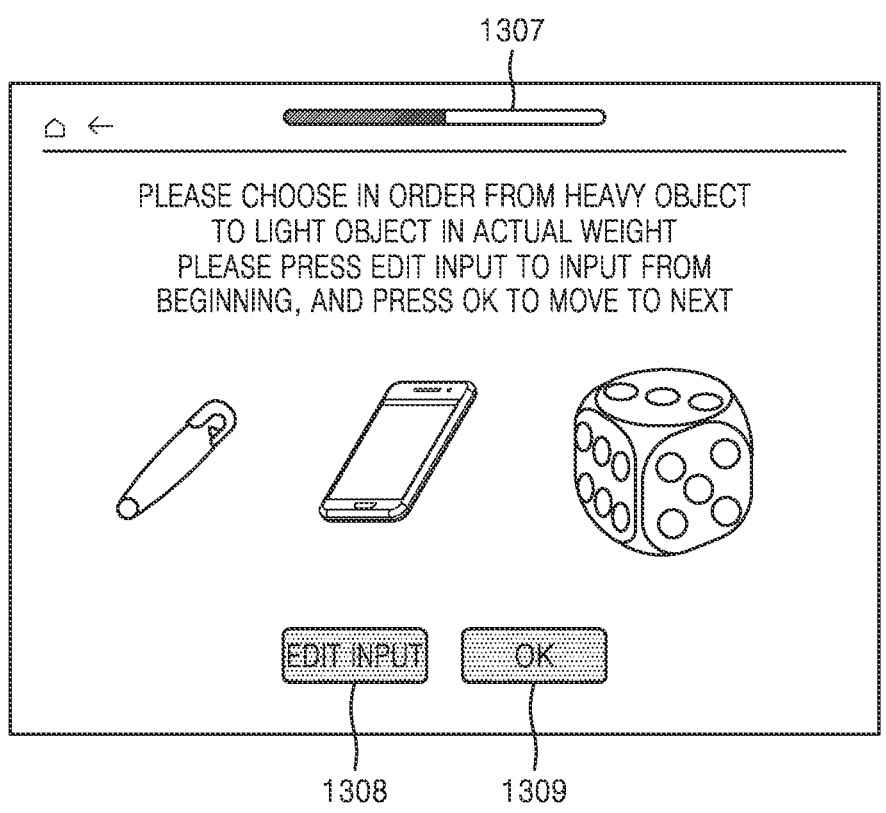

FIG. 13H illustrates a screen for performing the (8-2)th test process. The user may check the (8-2)th instruction, and then choose a plurality of second object presented images according to weight while looking at a progress bar 1307. The user may re-choose by inputting an edit input button 1308 when the choice needs to be edited. When the user inputs an OK button 1309 after completing the choice, a next screen may be displayed.

Figure 13I:
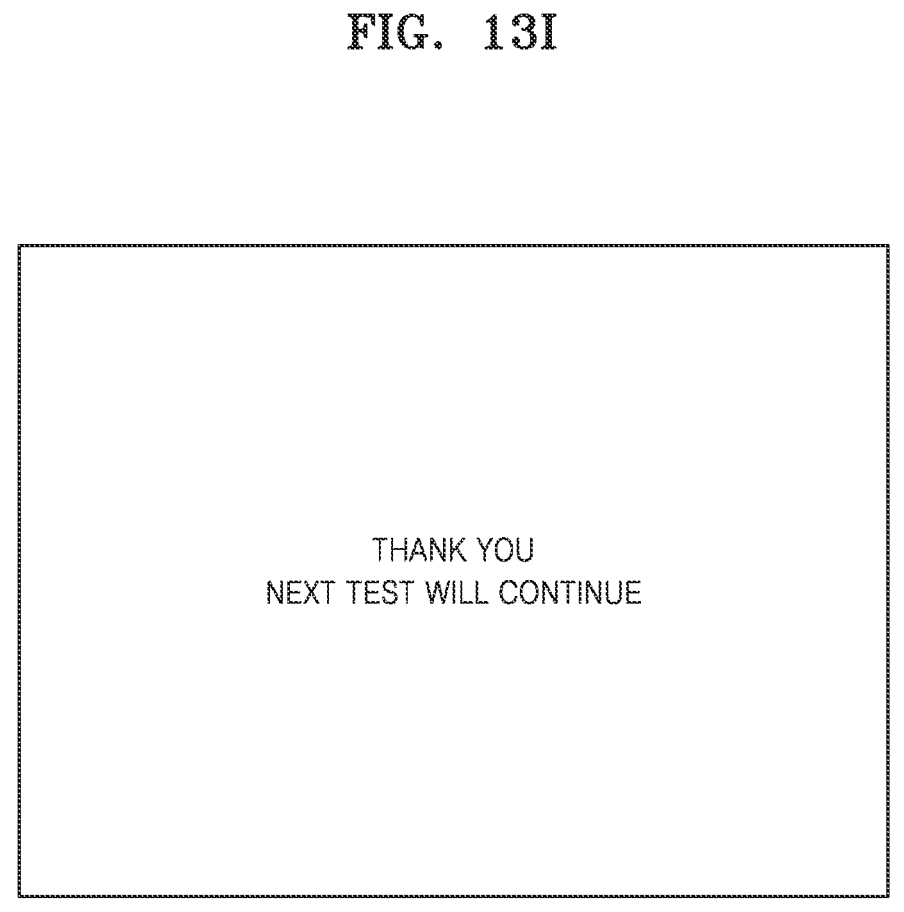

FIG. 13I illustrates a screen indicating completion of the performing of the (8-2)th test process and a start of a next test process.

Referring back to FIG. 3, the first processing unit 152 may perform the ninth test process including the ninth test process. According to the present embodiment, the first processing unit 152 may perform the ninth test process a plurality of times, excluding a practice test.

When the ninth test process is performed, the first processing unit 152 may provide a main image and a narration for the main image on a screen, and, after the narration is provided, provide a ninth instruction to choose an answer to a question while viewing a plurality of sub-images included in the main image to the user terminal 200.

The first processing unit 152 may receive, from the user terminal 200, a result of choosing the answer to the question, in response to the ninth instruction, and calculate the ninth test score by comparing the result with a correct answer. In the present embodiment, the larger the number of choice results determined as correct answers, the higher the ninth test score may be.

According to the present embodiment, before the ninth test process is performed, the first processing unit 152 may provide, in at least one of a text and an instruction screen, a method of performing the ninth test process to the user terminal 200, and perform a practice test for the ninth test process.

In the present embodiment, it may be evaluated that the social situation understanding is good when the ninth test score is higher than the ninth criterion cut-off score, and that the social situation understanding is declined when the ninth test score is lower than the ninth criterion cut-off score.

FIGS. 14A through 14G illustrate examples of screens provided to the user terminal 200 to perform the ninth test process.

Figure 14A:
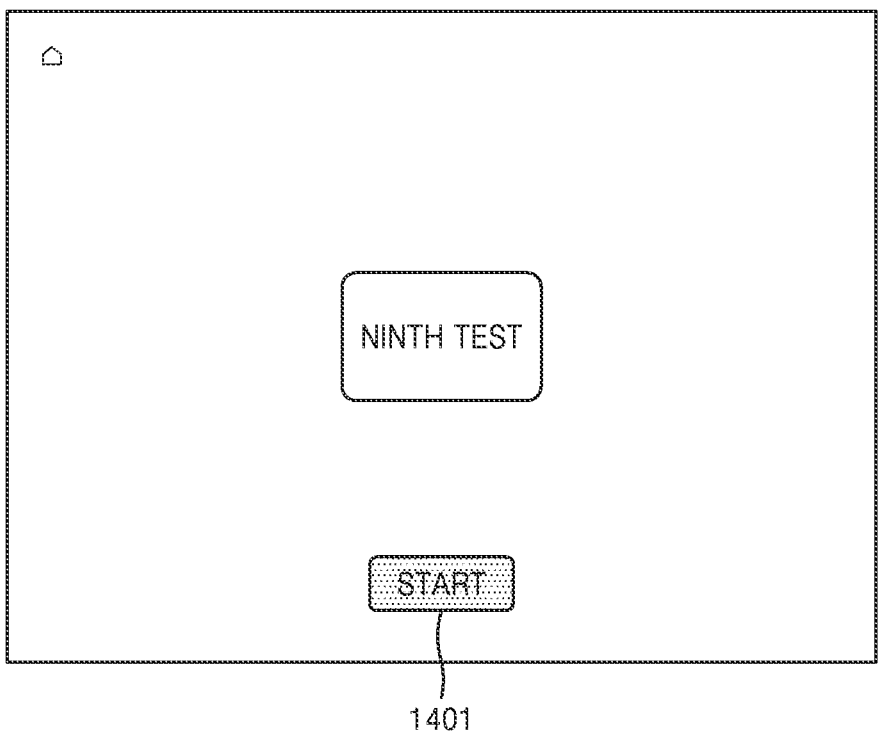
Figure 14B:
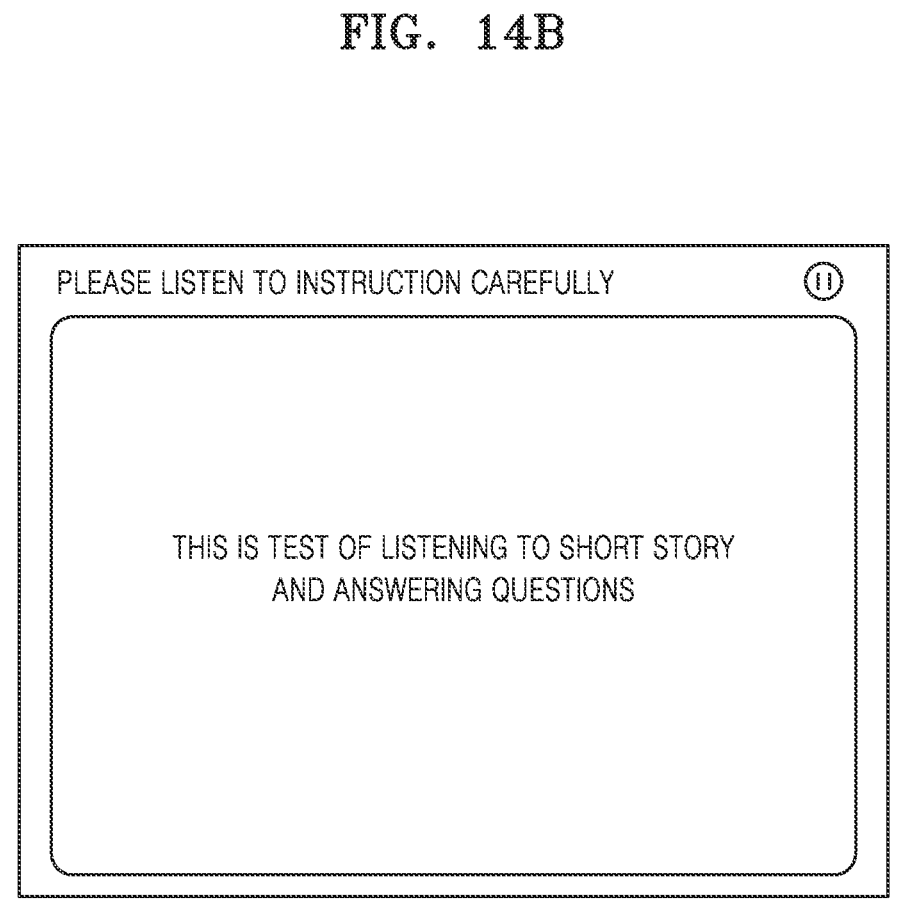

FIG. 14A illustrates a start screen of the ninth test process. When an input of the start button 1401 is received, a next screen may be displayed and an instruction screen may be displayed.

FIG. 14 illustrates an instruction screen. In FIG. 14B, it may be indicated a test of listening to a short story and answering a question.

Figure 14C:
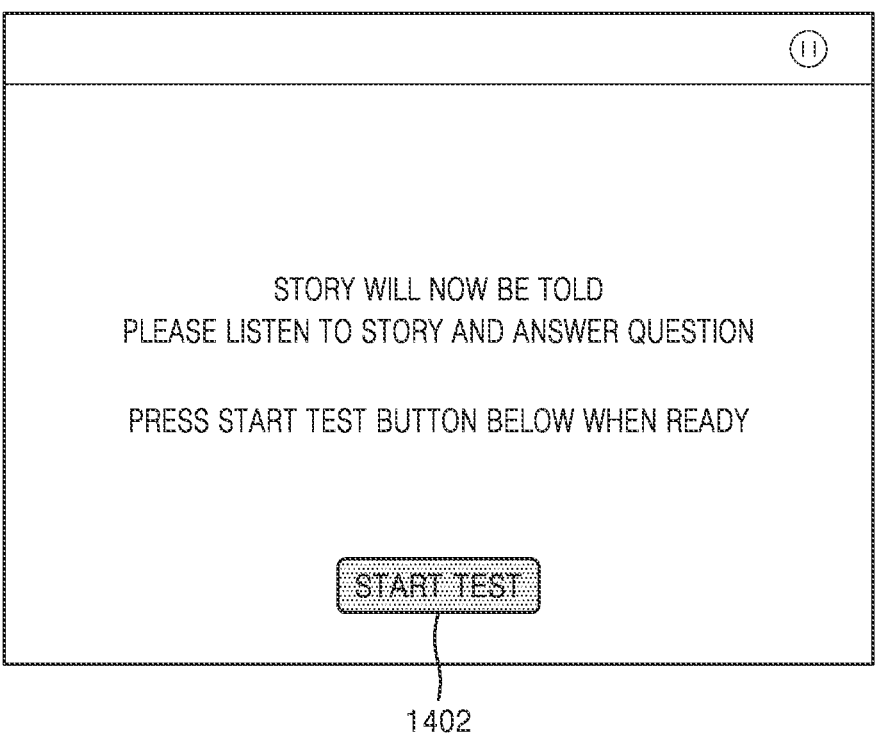

FIG. 14C illustrates a screen indicating a start of the ninth test process. When a test start button 1402 is input, a ninth test screen may be displayed.

Figure 14D:
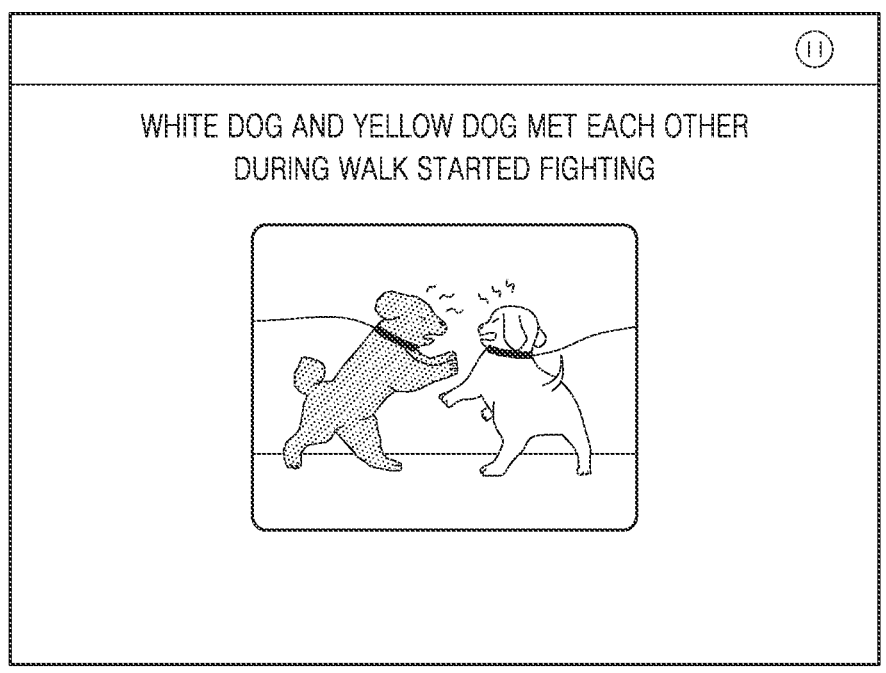
Figure 14E:
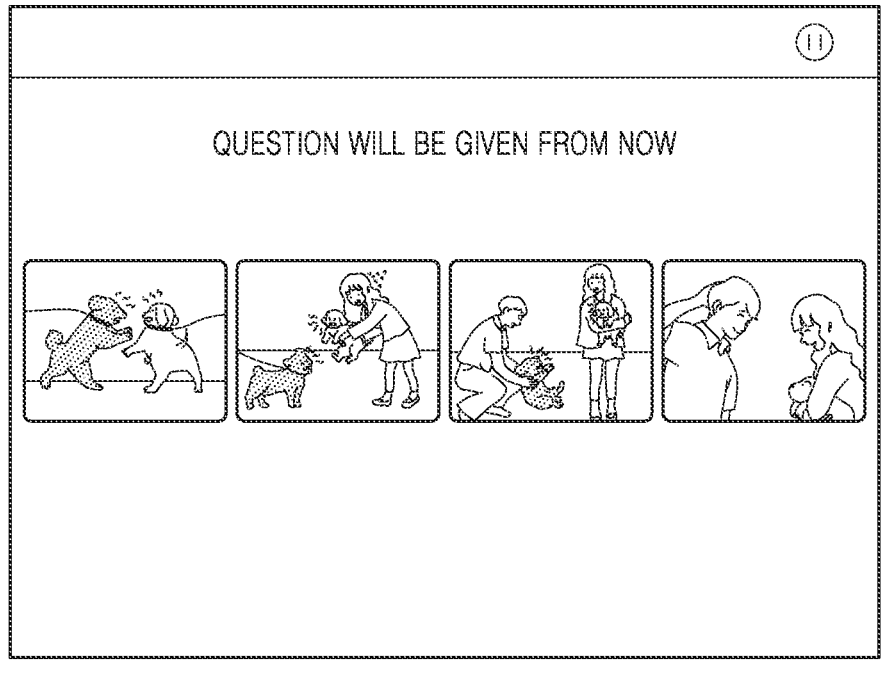
Figure 14F:
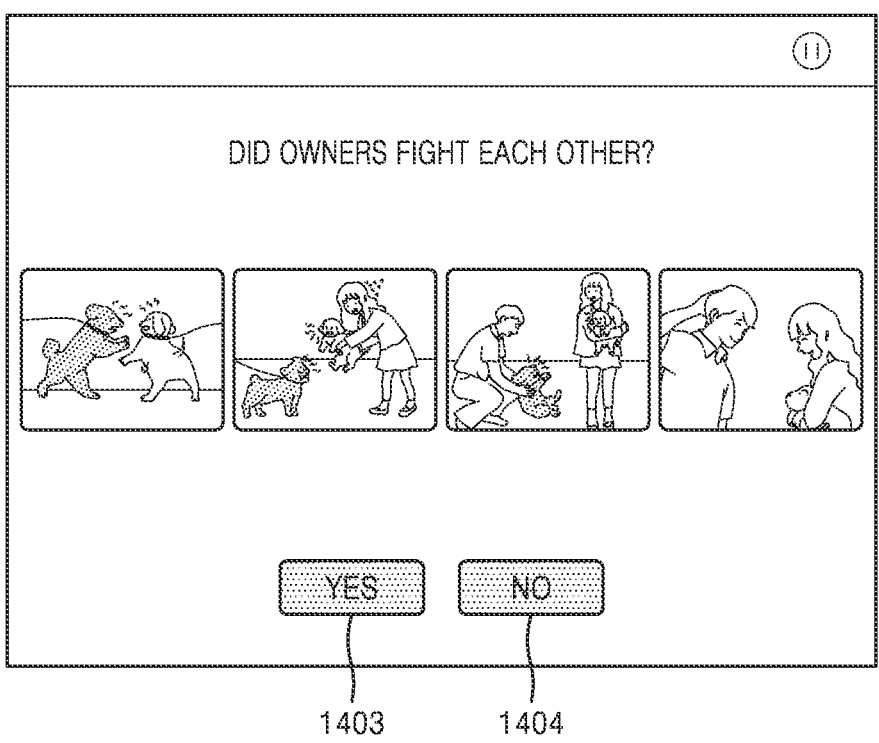

FIGS. 14D to 14F illustrate a ninth test screen. In FIG. 14D, an arbitrary main image and a narration for the arbitrary main image may be provided on a screen. In FIG. 14E, after the narration is provided, a plurality of sub-images included in the main image and an instruction indicating that a question will be asked may be displayed. In FIG. 14F, a plurality of sub-images, a question, and answer buttons (e.g., a yes button 1403 and a no button 1404) for choosing an answer to the questions may be displayed. A user may choose one of the answer buttons as an answer to a question while viewing the plurality of sub-images.

Figure 14G:
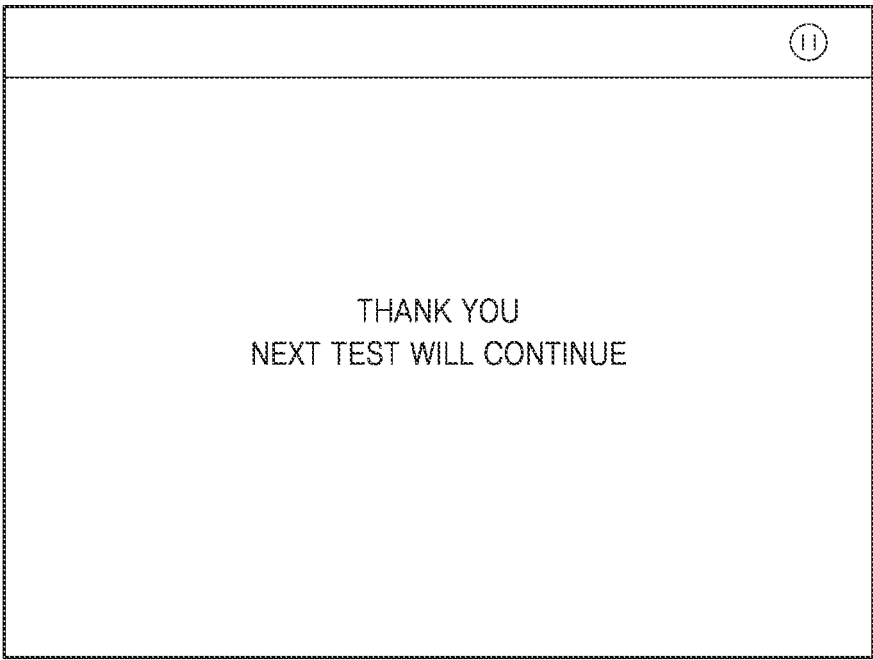

FIG. 14G illustrates a screen indicating completion of the performing of the ninth test process and a start of a next test process.

Referring back to FIG. 3, the first processing unit 152 may perform the tenth test process. According to the present embodiment, the first processing unit 152 may perform the tenth test process a plurality of times, excluding a practice test.

When the tenth test process is performed, the first processing unit 152 may illustrate a plurality of pre-set presented figures and provide, to the user terminal 200, a tenth instruction, in which it is instructed to choose a figure having a different color from among the plurality of pre-set presented figures.

The first processing unit 152 may receive, from the user terminal 200, a result of choosing a figure having a different color from among the plurality of pre-set presented figures, in response to the tenth instruction, and calculate the tenth test score by comparing the result with a correct answer. According to the present embodiment, the tenth test score may be calculated to be high when there are many results determined to be correct answers compared to the total number of times the tenth test processes have been performed.

According to the present embodiment, before the tenth test process is performed, the first processing unit 152 may provide, in at least one of a text and an instruction screen, a method of performing the tenth test process to the user terminal 200, and perform a practice test for the tenth test process.

According to the present embodiment, it may be evaluated that a color classifying ability is good when the tenth test score is higher than the tenth criterion cut-off score, and is declined when the tenth test score is lower than the tenth criterion cut-off score.

FIGS. 15A through 15J illustrate examples of screens provided to the user terminal 200 to perform the tenth test process.

Figure 15A:
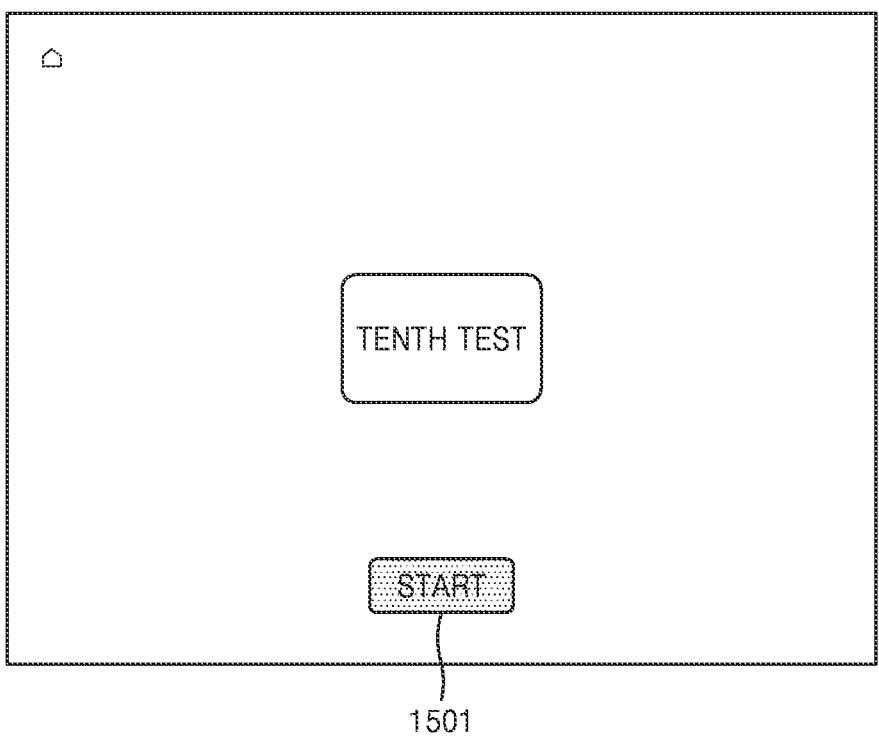

FIG. 15A illustrates a start screen of the tenth test process. When an input of a start button 1501 is received, a next screen may be displayed.

Figure 15B:

FIG. 15B illustrates a screen in which a method of performing the tenth test process is provided in a text and a start of a practice test process (tenth practice test process) for the fifth test process is notified. When a practice start button 1502 is input, a next screen may be displayed.

Figure 15C:
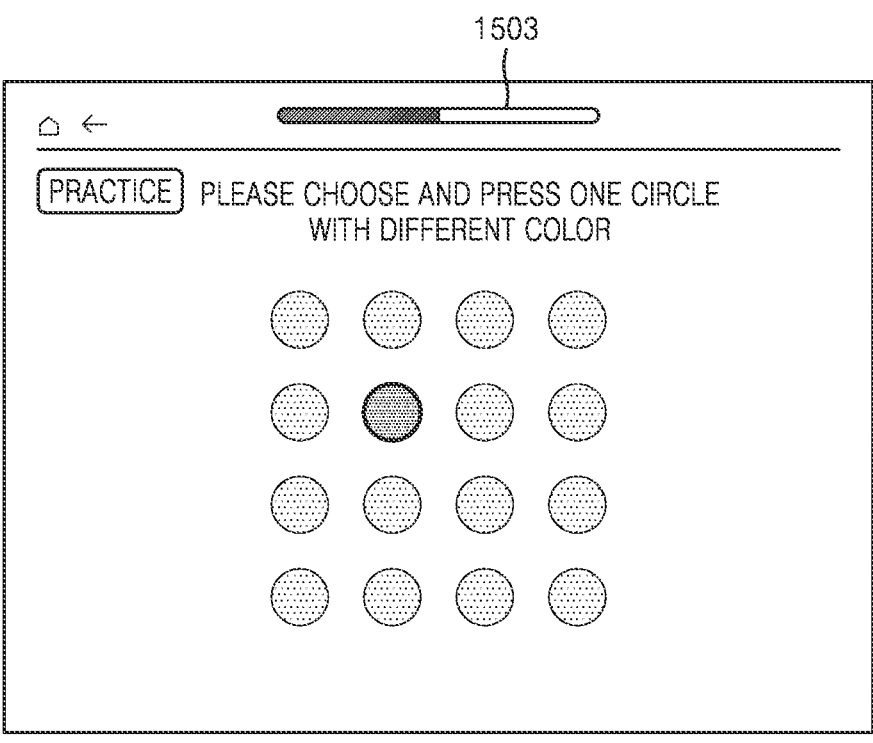

FIG. 15C illustrates a screen for performing the tenth practice test process. The user may check a tenth practice instruction, and choose a figure having a different color from among a plurality of pre-set presented figures while looking at a progress bar 1503. A next screen may be displayed when the choosing of a figure is completed or counting of a time limit is completed.

Figure 15D:
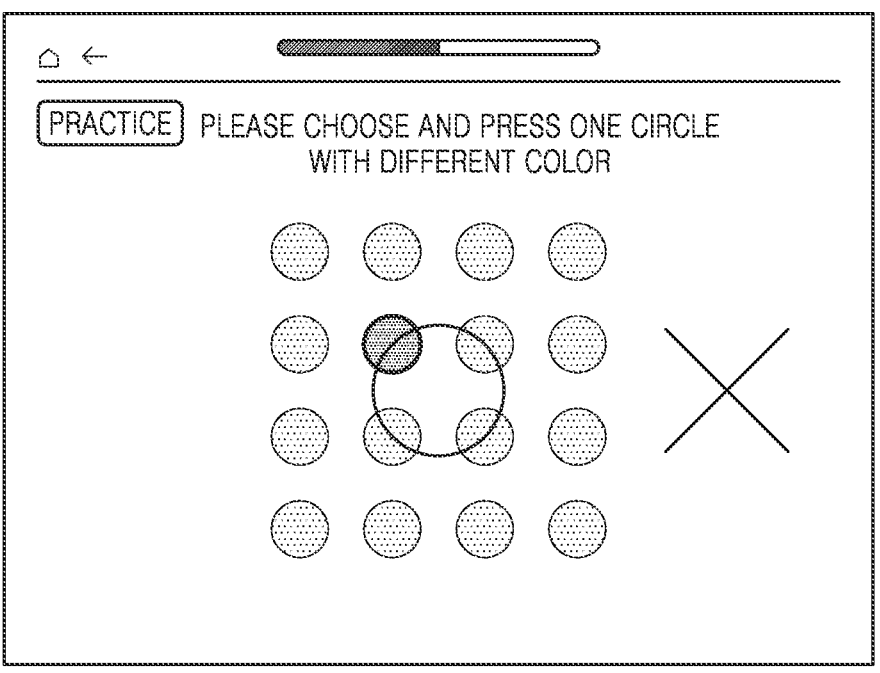

FIG. 15D illustrates a screen showing a result of performing the tenth practice test process of FIG. 15C. When the chosen figure is a correct answer, the correct answer may be indicated by using a correct answer sign and/or a correct answer sound effect, and when the chosen figure is a wrong answer, the wrong answer may be indicated by using a wrong answer sign and/or a wrong answer sound effect.

Figure 15E:
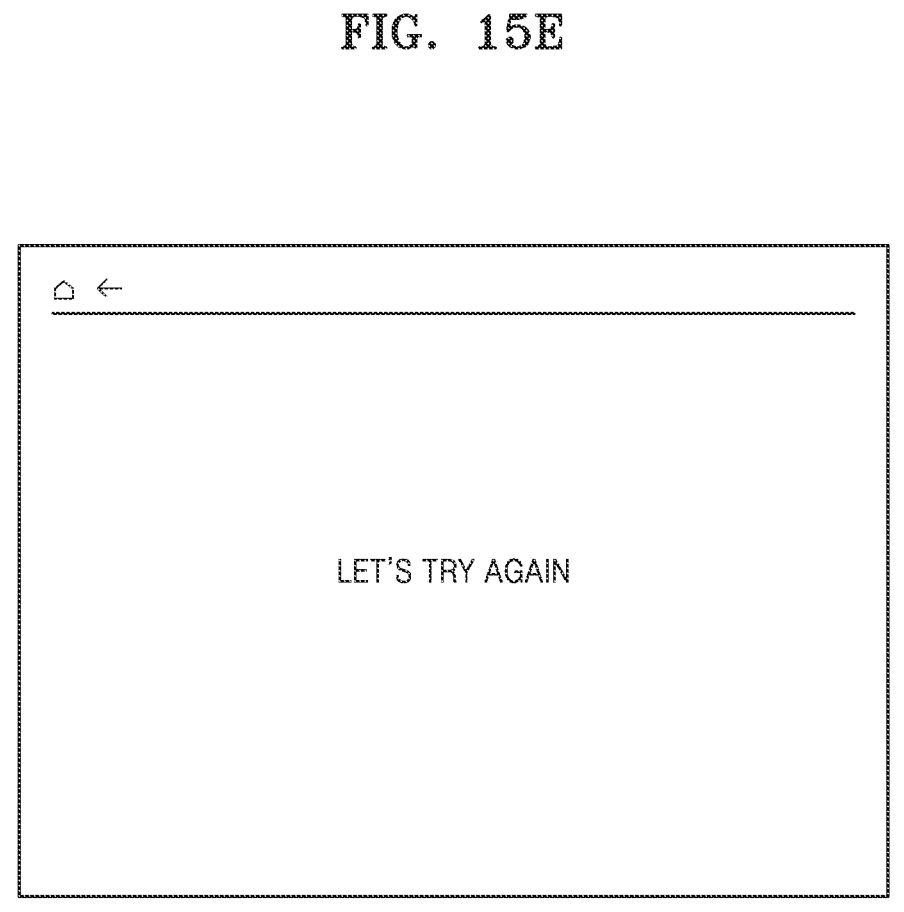

FIG. 15E illustrates a screen indicating a rerun of the tenth practice test process. The tenth practice test process may be rerun when a result of performing the tenth practice test process is a wrong answer.

Figure 15F:
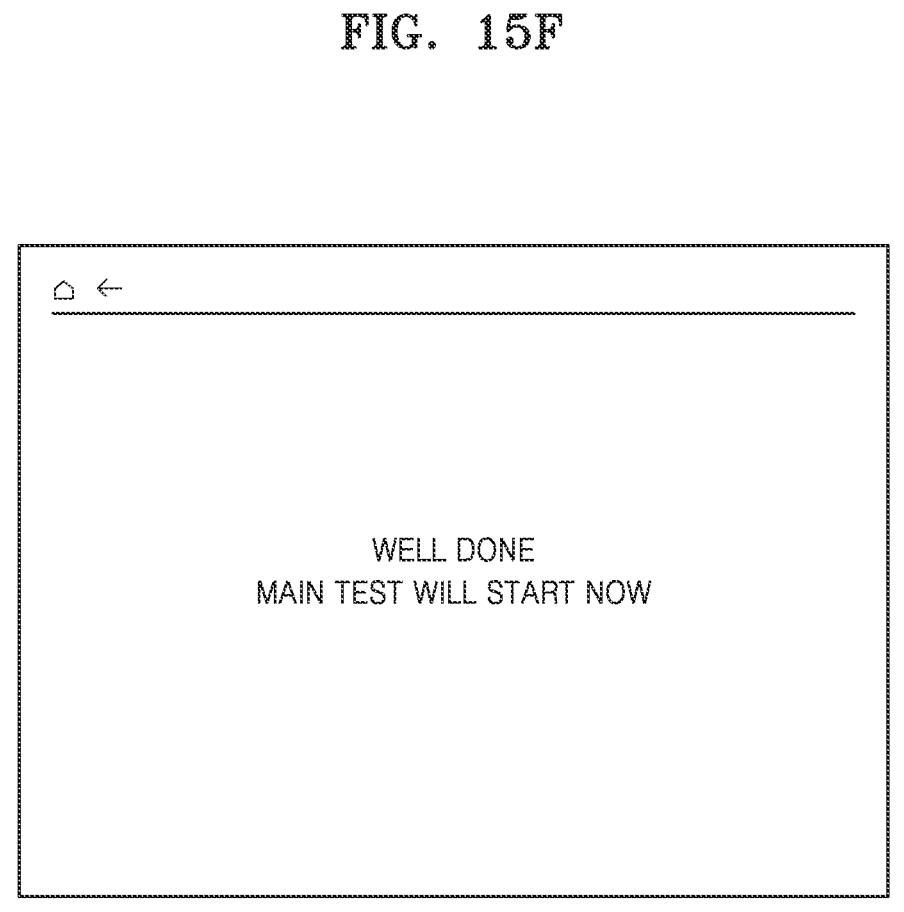

FIG. 15F illustrates a screen indicating completion of the performing of the tenth practice test process, and performing of a main test.

Figure 15G:
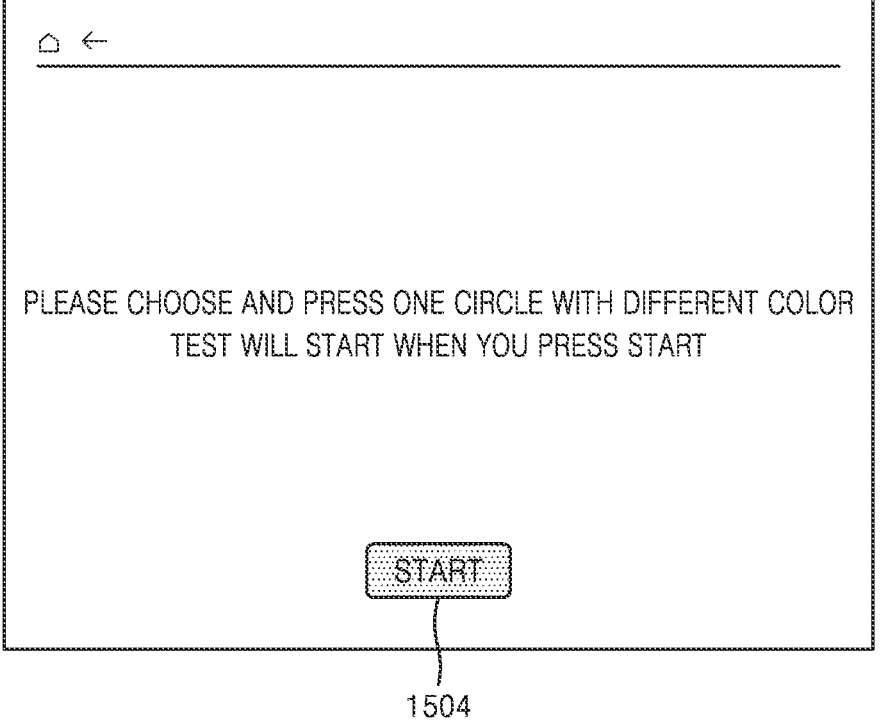

FIG. 15G illustrates a screen providing, in a text, a method of performing the tenth test process, and indicating a start of the tenth test process. When a start button 1504 is input, a next screen may be displayed.

Figure 15H:
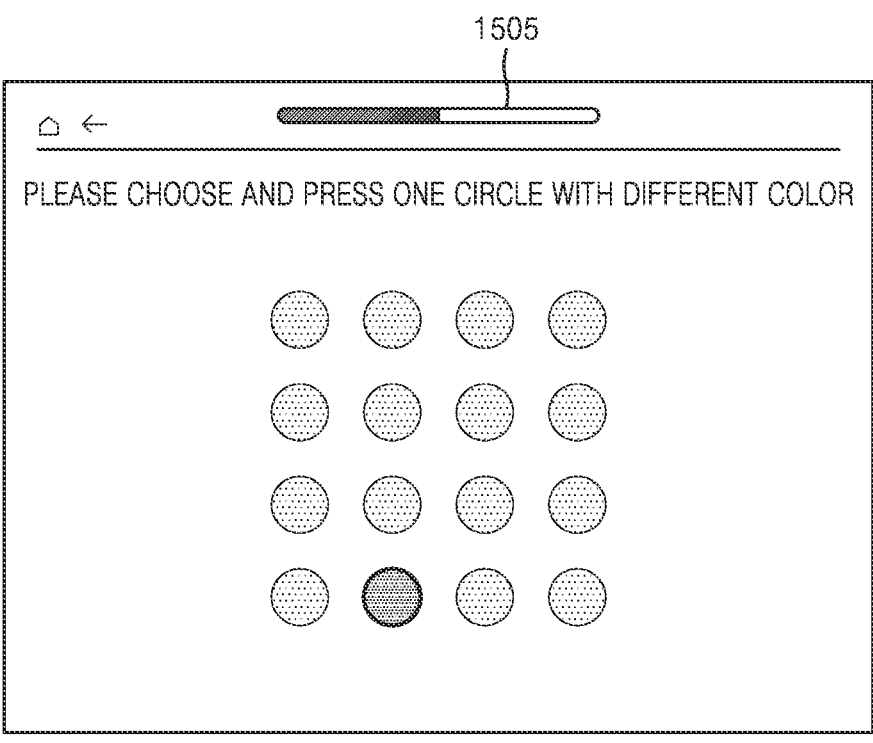

FIG. 15H illustrates a screen for performing the tenth test process. The user may check a tenth instruction, and choose a figure having a different color from among a plurality of pre-set presented figures while looking at a progress bar 1505. A next screen may be displayed when the choosing of a figure is completed or counting of a time limit is completed.

Figure 15I:
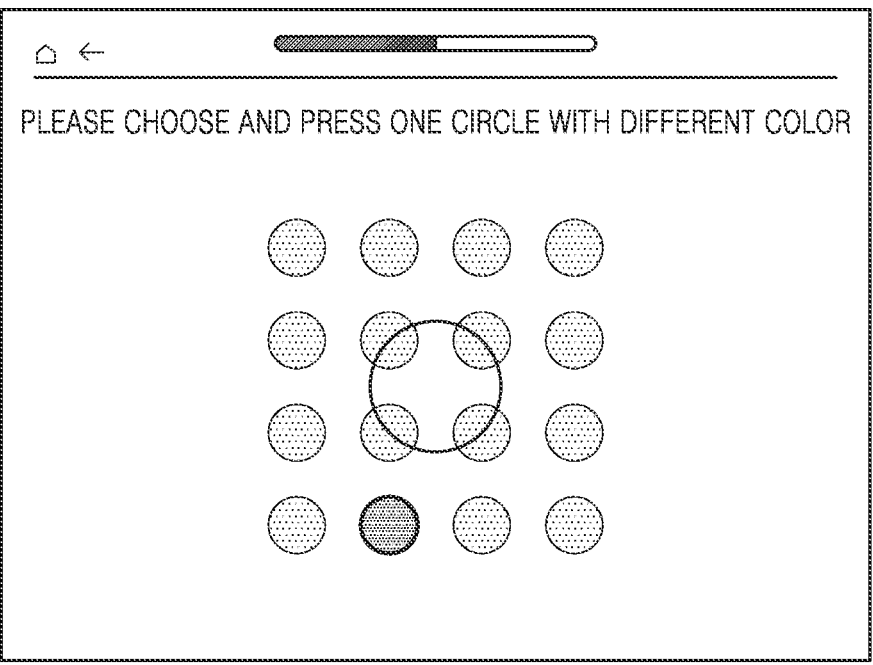

FIG. 15I illustrates a screen showing a result of performing the tenth test process of FIG. 15H. When the chosen figure is a correct answer, the correct answer may be indicated by using a correct answer sign and/or a correct answer sound effect. Also, when the chosen figure is a wrong answer, the wrong answer may be indicated by using a wrong answer sign and/or a wrong answer sound effect.

Figure 15J:
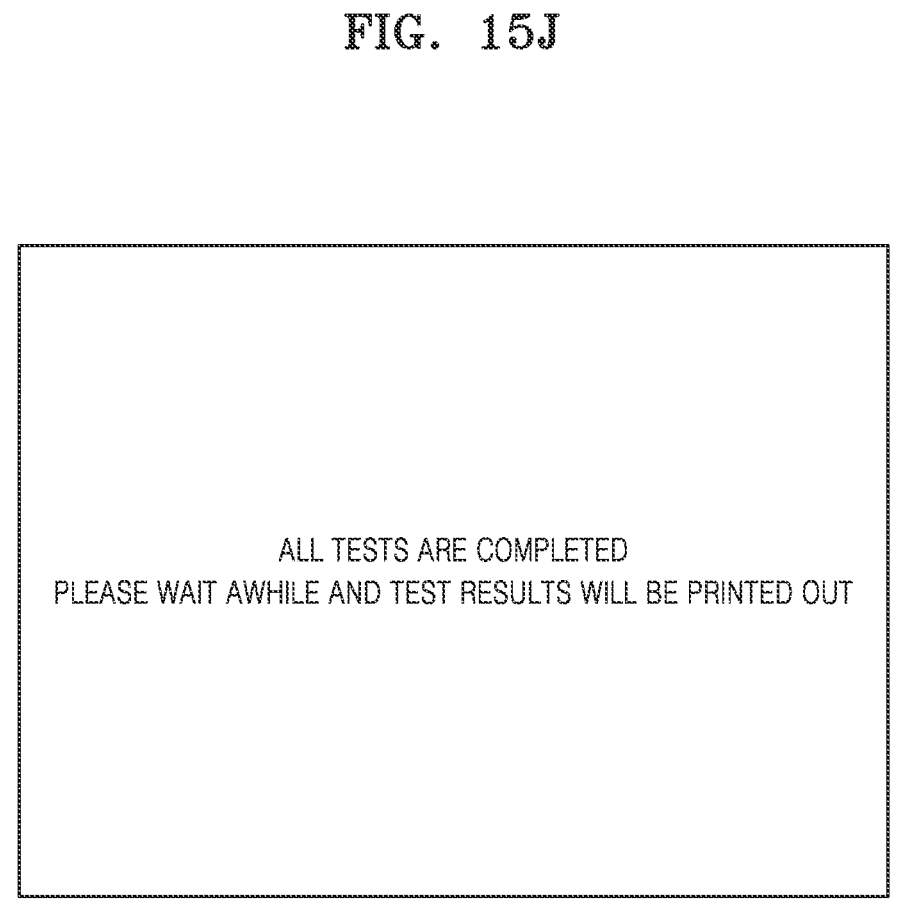

FIG. 15J illustrates a screen indicating completion of the performing of the tenth test process to stand by for test result printouts.

Referring back to FIG. 3, when the performing of the first test process through the tenth test process by the first processing unit 152 is completed, the second processing unit 153 may perform the category classification process of classifying at least one test item from among a plurality of test items as one neurocognitive category from among a plurality of neurocognitive categories.

The second processing unit 153 may classify the second test item and the fourth test item as the first neurocognitive category. The second processing unit 153 may classify the sixth test item and ninth test item as the second neurocognitive category. The second processing unit 153 may classify the eighth test item and the ninth test item as the third neurocognitive category. The second processing unit 153 may classify the tenth test item as the fourth neurocognitive category. The second processing unit 153 may classify the first test item, the third test item, the fifth test item, and the seventh test item as the fifth neurocognitive category.

When the category classification process is completed, the second processing unit 153 may perform the evaluation process of evaluating whether there is cognitive function decline in a neurocognitive category, based on a test score of a test item classified as the neurocognitive category.

In the present embodiment, when it is evaluated that there is cognitive function decline in at least one of the first neurocognitive category through the fifth neurocognitive category, the third processing unit 154 may generate an evaluation result outputting that the user may have mild cognitive impairment.

In the present embodiment, the evaluation process may include the first evaluation process through the fifth evaluation process.

The third processing unit 154 may perform the first evaluation process of evaluating whether there is cognitive function decline in the first neurocognitive category, based on the second test score and the fourth test score.

During the first evaluation process, the third processing unit 154 may compare the second test score for the second test item with a second reference score, and generate a first comparison result when the second test score is less than the second reference score. In the present embodiment, the second test score may include a language clue memory test score. In the present embodiment, the second reference score may include a second test score of a normal group, in which a second Z-score is a second standard deviation (for example, −1.5 SD).

In the present embodiment, the first comparison result may include a (1-1)th comparison result and a (1-2)th comparison result. The (1-1)th comparison result may be generated when the second test score is less than the second reference score. It may be determined that the language memory of the user is declined, based on the (1-1)th comparison result. The (1-2)th comparison result may be generated when the second test score is equal to or greater than the second reference score. It may be determined that the language memory of the user is good, based on the (1-2)th comparison result. In the present embodiment, the first comparison result may be replaced by the (1-1)th comparison result.

During the first evaluation process, the fourth processing unit 154 may compare the fourth test score for the fourth test item with a fourth reference score, and generate a second comparison result when the fourth test score is less than the fourth reference score. In the present embodiment, the fourth test score may include a visual graphic memory test score. In the present embodiment, the fourth reference score may include a fourth test score of a normal group, in which a fourth Z-score is a fourth standard deviation (for example, −1.5 SD).

In the present embodiment, the second comparison result may include a (2-1)th comparison result and a (2-2)th comparison result. The (2-1)th comparison result may be generated when the fourth test score is less than the fourth reference score. It may be determined that the visual perception memory of the user is declined, based on the (2-1)th comparison result. The (2-2)th comparison result may be generated when the fourth test score is equal to or greater than the fourth reference score. It may be determined that the visual perception memory of the user is good, based on the (2-2)th comparison result. In the present embodiment, the second comparison result may be replaced by the (2-1)th comparison result.

The fourth processing unit 154 may evaluate that there is cognitive function decline in the first neurocognitive category, i.e., memory, when at least one of the first comparison result and the second comparison result is generated.

The fourth processing unit 154 may perform the second evaluation process of evaluating whether there is cognitive function decline in the second neurocognitive category, based on the sixth test score and the eighth test score.

During the second evaluation process, the fourth processing unit 154 may compare the sixth test score for the sixth test item with an sixth reference score, and generate a fourth comparison result when the sixth test score is less than the sixth reference score. In the present embodiment, the sixth test score may include a face emotion test score. In the present embodiment, the sixth reference score may include an sixth test score of a normal group, in which an sixth Z-score is an sixth standard deviation (for example, −1.5 SD).

In the present embodiment, the third comparison result may include a (3-1)th comparison result and a (3-2)th comparison result. The (3-1)th comparison result may be generated when the eighth test score is less than the eighth reference score. It may be determined that the emotion intensity cognitive power of the user is declined, based on the (3-1)th comparison result. The (3-2)th comparison result may be generated when the eighth test score is equal to or greater than the eighth reference score. It may be determined that the emotion intensity cognitive power of the user is good, based on the (3-2)th comparison result. In the present embodiment, the third comparison result may be replaced by the (3-1)th comparison result.

During the second evaluation process, the third processing unit 154 may compare the ninth test score for the ninth test item with an ninth reference score, and generate a fourth comparison result when the ninth test score is less than the fourth reference score. In the present embodiment, the ninth test score may include a theory of mind test score. In the present embodiment, the ninth reference score may include a ninth test score of a normal group, in which a ninth Z-score is the ninth standard deviation (for example, −1.5 SD).

In the present embodiment, the fourth comparison result may include a (4-1)th comparison result and a (4-2)th comparison result. The (4-1)th comparison result may be generated when the ninth test score is less than the ninth reference score. It may be determined that the social situation understanding of the user is declined, based on the (4-1)th comparison result. The (4-2)th comparison result may be generated when the ninth test score is equal to or greater than the ninth reference score. It may be determined that the social situation understanding of the user is good, based on the (4-2)th comparison result. In the present embodiment, the fourth comparison result may be replaced by the (4-1)th comparison result.

The third processing unit 154 may evaluate that there is cognitive function decline in the second neurocognitive category, i.e., social cognition, when at least one of the third comparison result and the fourth comparison result is generated.

The third processing unit 154 may perform the third evaluation process of evaluating whether there is cognitive function decline in the third neurocognitive category, based on the eighth test score and the ninth test score.

During the third evaluation process, the third processing unit 154 may compare the eighth test score for the eighth test item with a eighth reference score, and generate a fourth comparison result when the eighth test score is less than the eighth reference score. In the present embodiment, the eighth test score may include a size weight test score. In the present embodiment, the eighth reference score may include a eighth test score of a normal group, in which a eighth Z-score is a eighth standard deviation (for example, −1.5 SD).

In the present embodiment, the fifth comparison result may include a (5-1)th comparison result and a (5-2)th comparison result. The (5-1)th comparison result may be generated when the seventh test score is less than the seventh reference score. It may be determined that the semantic memory of the user is declined, based on the (5-1)th comparison result. The (5-2)th comparison result may be generated when the seventh test score is equal to or greater than the seventh reference score. It may be determined that the semantic memory of the user is good, based on the (5-2)th comparison result. In the present embodiment, the fourth comparison result may be replaced by the (5-1)th comparison result.

The third processing unit 154 may perform the fourth evaluation process of evaluating whether there is cognitive function decline in the fourth neurocognitive category, based on the tenth test score.

During the fourth evaluation process, the third processing unit 154 may compare the tenth test score for the tenth test item with a tenth reference score, and generate a seventh comparison result when the tenth test score is less than the tenth reference score. In the present embodiment, the tenth test score may include a color perception test score. In the present embodiment, the tenth reference score may include a tenth test score of a normal group, in which a tenth Z-score is a tenth standard deviation (for example, −1.5 SD).

In the present embodiment, the sixth comparison result may include a (6-1)th comparison result and a (6-2)th comparison result. The (6-1)th comparison result may be generated when the sixth test score is less than the sixth reference score. It may be determined that the color classifying ability of the user is declined, based on the (6-1)th comparison result. The (6-2)th comparison result may be generated when the sixth test score is equal to or greater than the sixth reference score. It may be determined that the color classifying ability of the user is good, based on the (6-2)th comparison result. In the present embodiment, the seventh comparison result may be replaced by the (6-1)th comparison result.

The third processing unit 154 may perform the fifth evaluation process of evaluating whether there is cognitive function decline in the fifth neurocognitive category, based on the first test score, the third test score, the fifth test score, and the seventh test score.

During the fifth evaluation process, the third processing unit 154 may compare the first test score for the first test item with a first reference score, and generate an seventh comparison result when the first test score is less than the first reference score. In the present embodiment, the first test score may include a fluency test score. In the present embodiment, the first reference score may include a first test score of a normal group, in which a first Z-score is a first standard deviation (for example, −1.5 SD).

In the present embodiment, the seventh comparison result may include a (7-1)th comparison result and a (7-2)th comparison result. The (7-1)th comparison result may be generated when the first test score is less than the first reference score. It may be determined that the fluency of the user is declined, based on the (7-1)th comparison result. The (7-2)th comparison result may be generated when the first test score is equal to or greater than the first reference score. It may be determined that the fluency of the user is good, based on the (7-2)th comparison result. In the present embodiment, the eighth comparison result may be replaced by the (7-1)th comparison result.

During the fifth evaluation process, the third processing unit 154 may compare the third test score for the third test item with a third reference score, and generate a ninth comparison result when the third test score is less than the third reference score. In the present embodiment, the third test score may include a symbol number matching test score. In the present embodiment, the third reference score may include a third test score of a normal group, in which a third Z-score is a third standard deviation (for example, −1.5 SD).

In the present embodiment, the eighth comparison result may include a (8-1)th comparison result and a (8-2)th comparison result. The (8-1)th comparison result may be generated when the fourth test score is less than the fourth reference score. It may be determined that the inhibitory function of the user is declined, based on the (8-1)th comparison result. The (8-2)th comparison result may be generated when the fourth test score is equal to or greater than the fourth reference score. It may be determined that the inhibitory function of the user is good, based on the (8-2)th comparison result. In the present embodiment, the eighth comparison result may be replaced by the (8-1)th comparison result.

During the fifth evaluation process, the third processing unit 154 may compare the fifth test score for the fifth test item with a fifth reference score, and generate a ninth comparison result when the fifth test score is less than the fifth reference score. In the present embodiment, the fifth test score may include a Stroop test score. In the present embodiment, the fifth reference score may include a fifth test score of a normal group, in which a fifth Z-score is a fifth standard deviation (for example, −1.5 SD).

In the present embodiment, the ninth comparison result may include a (9-1)th comparison result and a (9-2)th comparison result. The (9-1)th comparison result may be generated when the fifth test score is less than the fifth reference score. It may be determined that the attention and working memory of the user are declined, based on the (9-1)th comparison result. The (9-2)th comparison result may be generated when the fifth test score is equal to or greater than the fifth reference score. It may be determined that the attention and working memory of the user are good, based on the (9-2)th comparison result. In the present embodiment, the ninth comparison result may be replaced by the (9-1)th comparison result.

During the fifth evaluation process, the third processing unit 154 may compare the seventh test score for the seventh test item with an seventh reference score, and generate an tenth comparison result when the seventh test score is less than the seventh reference score. In the present embodiment, the seventh test score may include a trail making test score. In the present embodiment, the seventh reference score may include an seventh test score of a normal group, in which an seventh Z-score is an seventh standard deviation (for example, −1.5 SD).

In the present embodiment, the tenth comparison result may include a (10-1)th comparison result and a (10-2)th comparison result. The (10-1)th comparison result may be generated when the seventh test score is less than the tenth reference score. It may be determined that the language control of the user is declined, based on the (10-1)th comparison result. The (10-2)th comparison result may be generated when the seventh test score is equal to or greater than the seventh reference score. It may be determined that the language control of the user is good, based on the (10-2)th comparison result. In the present embodiment, the tenth comparison result may be replaced by the (10-1)th comparison result.

The third processing unit 154 may evaluate that there is cognitive function decline in the fifth neurocognitive category, i.e., attention execution, when at least one of the seventh comparison result, the eighth comparison result, and the ninth comparison result is generated.

After completing the evaluation process, the transmitting unit 155 may transmit the evaluation result to the user terminal 200 and/or a terminal (not shown) of a practitioner (for example, a doctor).

Figure 16:
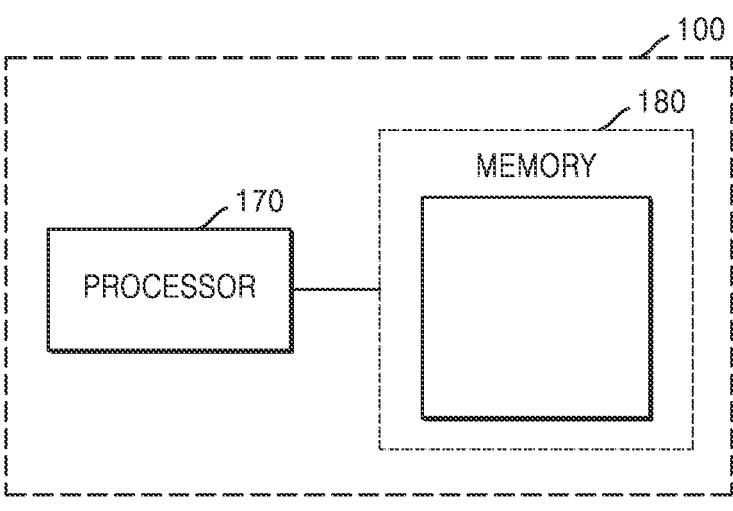
FIG. 16 is a block diagram for schematically describing a configuration of a test apparatus for evaluating cognitive function decline, according toother an embodiment.

FIG. 16 is a block diagram for schematically describing a configuration of the test apparatus 100 for evaluating cognitive function decline, according to another embodiment. Hereinafter, descriptions about details that overlap those of FIGS. 1 through 15 are omitted. Referring to FIG. 16, the test apparatus 100 according to another embodiment may include a processor 170 and a memory 180.

In the present embodiment, the processor 170 may process functions performed by the communication unit 110, the storage medium 120, the program storage unit 130, the database 140, the test management unit 150, and the control unit 160 shown in FIGS. 2 and 3.

The processor 170 may control all operations of the test apparatus 100. Here, the processor may denote a hardware-embedded data processing device including a physically structured circuit to perform a function represented by an instruction or a code included in a program. Examples of the hardware-embedded data processing device may include processing devices, such as a microprocessor, a central processing unit, a processor core, a multiprocessor, ASIC, and FPGA, but the scope of the disclosure is not limited thereto.

The memory 180 may be operatively connected to the processor 170, and may store at least one code in association with an operation performed by the processor 170.

Also, the memory 180 may temporarily or permanently store data processed by the processor 170, and may include data built in the database 140. Here, the memory 180 may include a magnetic storage medium or a flash storage medium, but the scope of the disclosure is not limited thereto. The memory 180 may include an internal memory and/or an external memory, and may include a volatile memory, such as a DRAM, an SRAM, or an SDRAM, a non-volatile memory, such as an OTPROM, a PROM, an EPROM, an EEPROM, a mask ROM, a flash ROM, an NAND flash memory, or a NOR flash memory, a flash drive, such as an SSD, a CF card, an SD card, a micro-SD card, a mini-SD card, an XD card, or a memory stick, or a storage device, such as an HDD.

FIGS. 17 through 20 are flowcharts of test methods for evaluating cognitive function decline, according to embodiments. Hereinafter, descriptions about details that overlap those of FIGS. 1 through 16 are omitted. The test method for evaluating cognitive function decline, according to the present embodiment will be described based on an assumption that the test apparatus 100 performs the test method in the processor 170 with the help of peripheral components.

Figure 17:
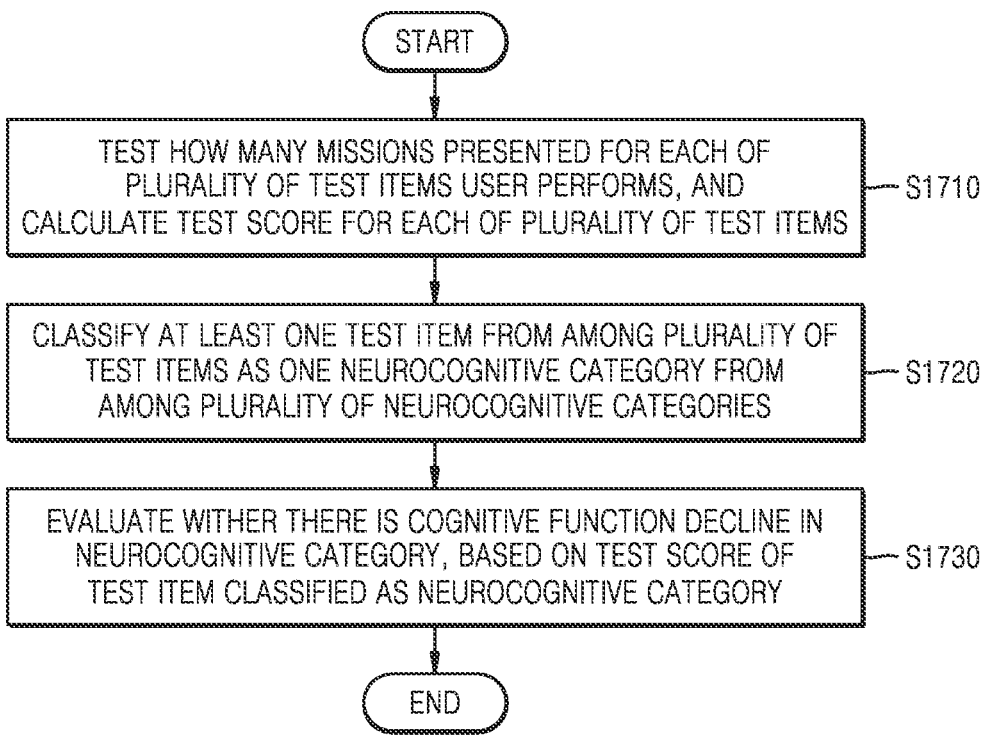

Referring to FIG. 17, in operation S1710, the processor 170 may test how many missions presented for each of the plurality of test items the user performs, and calculate the test score for each of the plurality of test items. In the present embodiment, operation S1710 may be referred to as a testing stage in the claims below.

Figure 18:
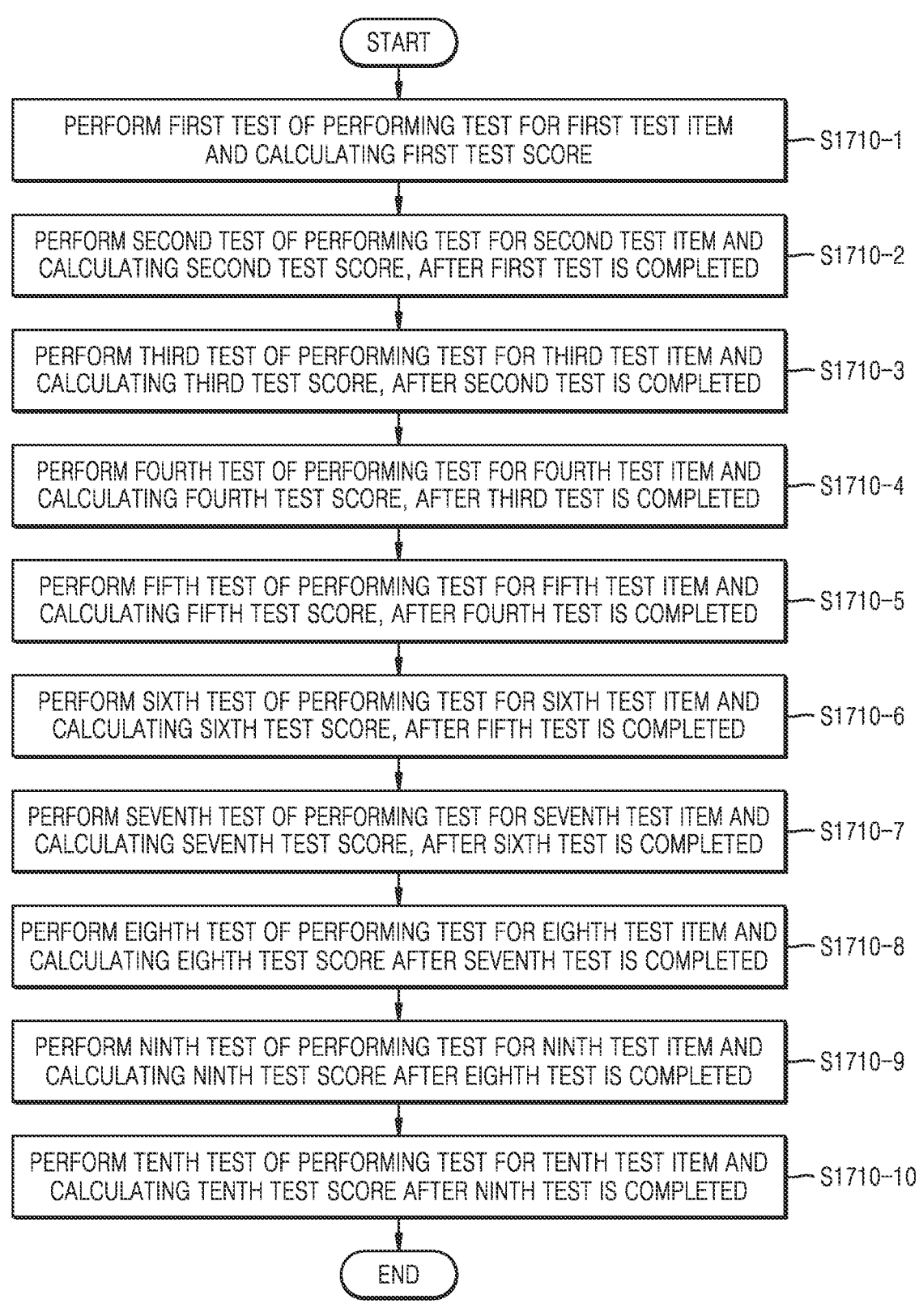

FIG. 18 illustrates a detailed flowchart of the testing stage. Referring to FIG. 18, in operation S1710-1, the processor 170 may perform a first testing stage of performing a test for the first test item, in which it is evaluated how many words corresponding to a pre-set presented category are uttered within a time limit, and calculating the first test score.

In operation S1710-2, the processor 170 may perform a second testing stage of performing a test for the second test item, in which words or images are learned while instructing a pre-set category clue and it is evaluated how many learned words or images are recalled after a pre-set time, and calculating the second test score, after the first testing stage is completed.

In operation S1710-3, the processor 170 may perform a third testing stage of performing a test for the third test item, in which how accurately and quickly an arbitrary number matched with a presented symbol image is selected within a pre-set time limit by looking at the presented symbol image, and calculating the third test score, after the second testing stage is completed.

In operation S1710-4, the processor 170 may perform a fourth testing stage of performing a test for the fourth test item, in which pre-set presented images are learned and it is evaluated how many learned presented images are recalled after a pre-set time, and calculating the fourth test score, after the third testing stage is completed.

In operation S1710-5, the processor 170 may perform a fifth testing stage of performing a test for the fifth test item, in which it is evaluated whether a pre-set presented word and a color of the pre-set presented word are accurately uttered, and calculating the fifth test score, after the fourth testing stage is completed.

In operation S1710-6, the processor 170 may perform a sixth testing stage of performing a test for the sixth test item, in which it is evaluated whether intensity of an emotion shown on a pre-set face presented image is recognized, and calculating the sixth test score, after the fifth testing stage is completed.

In operation S1710-7, the processor 170 may perform a seventh testing stage of performing a test for the seventh test item, in which how accurately and quickly a presented number is selected within a pre-set time limit and presenting numbers and days and evaluating how accurately and quickly a day corresponding to a number is selected, and calculating the seventh test score, after the sixth testing stage is completed.

In operation S1710-8, the processor 170 may perform an eighth testing stage of performing a test for the eighth test item, in which it is evaluated whether sizes and weights of pre-set presented objects are arranged in a descending order or ascending order, and calculating the eighth test score, after the seventh testing stage is completed.

In operation S1710-9, the processor 170 may perform a ninth testing stage of performing a test for the ninth test item, in which an arbitrary image and a narration for the arbitrary image are provided and, after the narration is provided, determining a degree of social situation understanding based on a result of collecting correct responses to questions, and calculating the ninth test score, after the eighth testing stage is completed.

In operation S1710-10, the processor 170 may perform a tenth testing stage of performing a test for the tenth test item, in which it is evaluated whether a figure of a color different from a color of a pre-set presented figure is found, and calculating the tenth test score, after the ninth testing stage is completed.

In embodiments, while performing one of the testing stages, if it is determined that the user is not able to go through the testing stage adequately, e.g., the user's responses significantly deviate from responses of other users or no input is received for a certain period of time, the processor 170 may end the corresponding testing stage and move to the next testing stage.

In some embodiments, if a user is retaking a test within a predetermined period of the previous test (e.g., within one-month, 15 days, 5 days, etc.), the processor 170 may use a different set of words to presented to the user for the present test from the set of words used in the previous test.

Referring back to FIG. 17, in operation S1720, the processor 170 may classify at least one test item from among the plurality of test items as one neurocognitive category from among a plurality of neurocognitive categories, after the testing stage is completed. In the present embodiment, operation S1720 may be referred to as a category classifying stage in the claims below.

Figure 19:
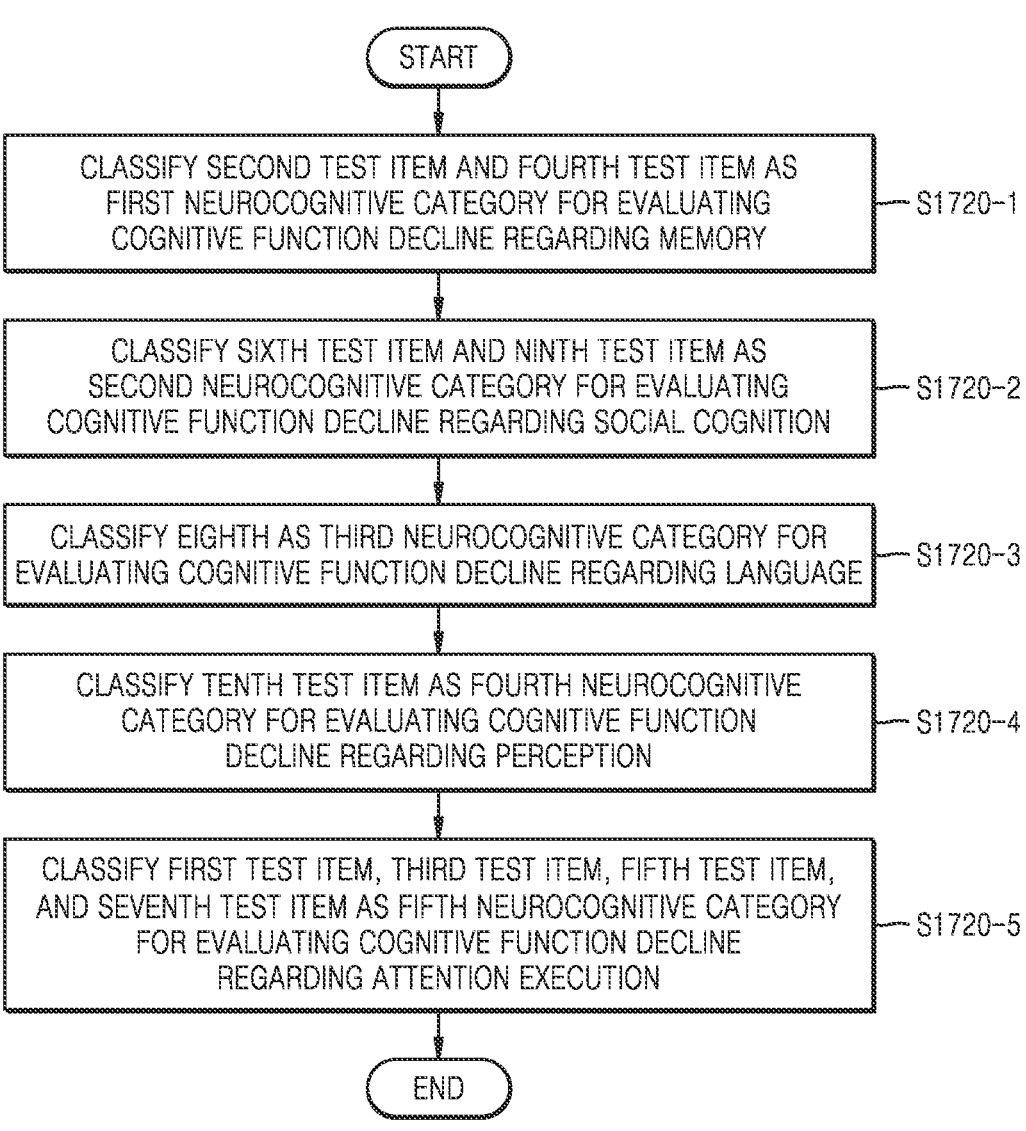

FIG. 19 illustrates a detailed flowchart of the category classifying stage. Referring to FIG. 19, in operation S1720-1, the processor 170 may classify the second test item and the fourth test item as the first neurocognitive category for evaluating cognitive function decline regarding memory.

In operation S1720-2, the processor 170 may classify the sixth test item and ninth test item as the second neurocognitive category for evaluating cognitive function decline regarding social cognition.

In operation S1720-3, the processor 170 may classify the eighth test item as the third neurocognitive category for evaluating cognitive function decline regarding language.

In operation S1720-4, the processor 170 may classify the tenth test item as the fourth neurocognitive category for evaluating cognitive function decline regarding perception.

In operation S1720-5, the processor 170 may classify the third test item, the fifth test item, the seventh test item, and the eleventh test item as the fifth neurocognitive category for evaluating cognitive function decline regarding attention execution.

Referring back to FIG. 17, in operation S1730, the processor 170 may evaluate whether there is cognitive function decline in a neurocognitive category, based on a test score of a test item classified as the neurocognitive category, after the category classifying stage is completed. In the present embodiment, operation S1730 may be referred to as an evaluating stage in the claims below.

In embodiments, if it is determined that there is cognitive function decline in a neurocognitive category, the processor 170 may perform actions for treating the user. For example, the processor 170 may search hospitals that may treat the cognitive function decline based on the location of the user. The location of the user may be determined based on the location of device of the user, such as the user terminal 200 in FIG. 1. The location of the device of the user may be obtained, e.g., by receiving a GPS signal from the user terminal 200. Then, the processor 170 may transmit information about the searched hospitals to the user terminal 200 such that the screen of the user terminal 200 displays the information about the searched hospitals such as locations of the hospitals, doctors at the hospitals, available treatments, available medical devices, and the like. The processor 170 may reserve an appointment with a doctor at one of the hospitals for the user and transmit information about the appointment to the doctor.

As another example, if it is determined that there is cognitive function decline in a neurocognitive category, the processor 170 may determine a suggested test, such as, an MRI exam, a CT exam, a PET exam, a blood test, a Cerebrospinal fluid test based on the test result, and transmit the suggested test to the user terminal 200 such that the screen of the user terminal 200 displays the information about the suggested test. The information about the suggested test may be transmitted to a primary doctor of the user.

As another example, if it is determined that there is cognitive function decline in a neurocognitive category, the processor 170 may provide additional questions to the user, such as questions regarding physical Activity of daily living and instrumental activity of daily living, questions for determining whether the cognitive function decline is due to senile depression, questions for confirming behavioral and psychological Symptom in Dementia.

In embodiments, if it is determined that the user may have a certain disease or a dementia based on the test results, the processor 170 may formulate additional tests customized for the user. For example, if the user is suspected to have Parkinson disease, Parkinson disease dementia, or Lewy body dementia, the processor 170 may perform a color vision test to check the user's ability to distinguish between colors. As another example, if the user is suspected to have frontotemporal dementia, the processor 170 may perform additional tests such as a theory of mind test, a facial emotion test, and the like, in order to more accurately evaluate the level of social cognition of the user.

In embodiments, after the processor 170 provides suggestions for treating the cognitive function decline, the processor 170 deletes the calculated scores and the evaluation results.

In embodiments, if it is determined that there is cognitive function decline in a neurocognitive category, the processor 170 may instruct the user terminal to display information for treating the cognitive function decline based on the test score or display additional tests for confirming specific diseases or dementia. The information for treating the cognitive function decline may include hospital locations, doctor information, hospital appointment information, suggested medical tests and the like. The additional tests may include a theory of mind test, a facial emotion test, a color vision test, and the like.

FIG. 20 illustrates a detailed flowchart of the evaluating stage. Referring to FIG. 20, in operation S1730-1, the processor 170 may perform the first evaluation process. During the first evaluation process, the processor 170 may compare the second test score for the second test item with the second reference score, and generate the first comparison result when the second test score is less than the second reference score. During the first evaluation process, the processor 170 may compare the fourth test score for the fourth test item with the fourth reference score, and generate the second comparison result when the fourth test score is less than the fourth reference score. The processor 170 may evaluate that there is cognitive function decline in the first neurocognitive category, i.e., memory, when at least one of the first comparison result and the second comparison result is generated.

When evaluating whether there is cognitive function decline in the memory, only the second test item and/or the fourth test item are used from among the first test item through the tenth test item, and thus an evaluation result may be calculated by using lesser computer resources and higher processing speed compared to resources and a processing speed when all of the first test item through the tenth test item are used, and accuracy and reliability of cognitive function decline evaluation may be increased.

In operation S1730-2, the processor 170 may perform the second evaluation process. During the second evaluation process, the processor 170 may compare the sixth test score for the sixth test item with the sixth reference score, and generate the third comparison result when the sixth test score is less than the sixth reference score. During the second evaluation process, the processor 170 may compare the ninth test score for the ninth test item with an ninth reference score, and generate a fourth comparison result when the ninth test score is less than the fourth reference score.

The processor 170 may evaluate that there is cognitive function decline in the second neurocognitive category, i.e., social cognition, when at least one of the third comparison and the fourth comparison result is generated.

When evaluating whether there is cognitive function decline in the social cognition, only the sixth test item and/or ninth test item is used from among the first test item through the tenth test item, and thus an evaluation result may be calculated by using lesser computer resources and higher processing speed compared to the resources and the processing speed when all of the first test item through the tenth test item are used, and the accuracy and the reliability of the cognitive function decline evaluation may be increased. If it is determined that there is cognitive function decline in the social cognition, the processor 170 may perform additional tests such as a theory of mind test, a facial emotion test, and the like, in order to more accurately evaluate the level of social cognition of the user.

In operation S1730-3, the processor 170 may perform the third evaluation process. During the third evaluation process, the processor 170 may compare the eighth test score for the seventh test item with the eighth reference score, and generate the fifth comparison result when the eighth test score is less than the eighth reference score. The processor 170 may evaluate that there is cognitive function decline in the third neurocognitive category, i.e., language, when fifth comparison result is generated.

When evaluating whether there is cognitive function decline in the language, only the eighth test item are used from among the first test item through the tenth test item, and thus an evaluation result may be calculated by using lesser computer resources and higher processing speed compared to the resources and the processing speed when all of the first test item through the tenth test item are used, and the accuracy and the reliability of the cognitive function decline evaluation may be increased.

In operation S1730-4, the processor 170 may perform the fourth evaluation process. During the fourth evaluation process, the processor 170 may compare the tenth test score for the fifth test item with the tenth reference score, and generate the sixth comparison result when the fifth test score is less than the fifth reference score. The processor 170 may evaluate that there is cognitive function decline in the fourth neurocognitive category, i.e., perception, when at least one of the sixth comparison result is generated.

When evaluating whether there is cognitive function decline in the perception, only the tenth test item are used from among the first test item through the tenth test item, and thus an evaluation result may be calculated by using lesser computer resources and higher processing speed compared to the resources and the processing speed when all of the first test item through the tenth test item are used, and the accuracy and the reliability of the cognitive function decline evaluation may be increased.

In operation S1730-5, the processor 170 may perform the fifth evaluation process. During the fifth evaluation process, the third processor 170 may compare the first test score for the first test item with the first reference score, and generate the seventh comparison result when the first test score is less than the first reference score. During the fifth evaluation process, the processor 170 may compare the third test score for the third test item with the third reference score, and generate the eighth comparison result when the third test score is less than the third reference score. During the fifth evaluation process, the processor 170 may compare the fifth test score for the fifth test item with the fifth reference score, and generate the fifth comparison result when the fifth test score is less than the fifth reference score. During the fifth evaluation process, the processor 170 may compare the seventh test score for the eleventh test item with the seventh reference score, and generate the seventh comparison result when the seventh test score is less than the seventh reference score. The processor 170 may evaluate that there is cognitive function decline in the fifth neurocognitive category, i.e., attention execution, when at least one of the seventh comparison result, the eighth comparison result, and the ninth comparison result is generated.

When evaluating whether there is cognitive function decline in the attention execution, only the first test item, the third test item, the fifth test item, and/or the seventh test item are used from among the first test item through the eleventh test item, and thus an evaluation result may be calculated by using lesser computer resources and higher processing speed compared to the resources and the processing speed when all of the first test item through the eleventh test item are used, and the accuracy and the reliability of the cognitive function decline evaluation may be increased.

The embodiments according to the disclosure described above may be implemented in the form of a computer program executable by various components on a computer, and such a computer program may be recorded on a computer-readable medium. Here, the computer-readable medium may include hardware devices specially designed to store and execute program instructions, such as magnetic media, such as a hard disk, a floppy disk, and a magnetic tape, optical recording media, such as CD-ROM and DVD, magneto-optical media such as a floptical disk, and read-only memory (ROM), random-access memory (RAM), and a flash memory.

The computer program may be specially designed for the disclosure or well known to one of ordinary skill in the computer software field. Examples of the computer program include not only machine codes generated by a compiler, but also high-level language codes executable by a computer by using an interpreter or the like.

The term "the" and similar referential terms in the specification (specifically in the claims) of the disclosure may be used for both the singular and the plural. Further, when a range is described in the disclosure, the disclosure includes inventions to which individual values belonging to the range are applied (unless otherwise stated), and it is considered that each individual value configuring the range is described in the detailed description of the disclosure.

Unless an order is clearly stated or unless otherwise stated, operations configuring a method according to the disclosure may be performed in an appropriate order. The disclosure is not necessarily limited by an order the operations are described. In the disclosure, the use of all examples or exemplary terms (for example, "etc.") is merely for describing the disclosure in detail and the scope of the disclosure is not limited by those examples or exemplary terms unless defined in the claims. Also, it would be obvious to one of ordinary skill in the art that various modifications, combinations, and changes may be configured according to design conditions and factors within the scope of claims or equivalents.

Therefore, the spirit of the disclosure should not be determined limitedly based on the above-described embodiments, and not only the appended claims but also all ranges equivalent to or equivalently changed from the claims are within the scope of the spirit of the disclosure.

According to the disclosure, by providing a user interface that is explicit and easy to understand during a test of evaluating cognitive function decline online, an aged user may perform the test of evaluating cognitive function decline without difficulty.

Also, during a test of evaluating cognitive function decline online, the test is performed by directly involving a user and reducing involvement of a tester, and thus test accuracy regarding the user may be improved.

In addition, a test result is immediately checked after a test of evaluating cognitive function decline online is completed, and a stored past result is checked for tracing, and thus a quick and accurate diagnosis and preventive measures may be presented to a patient.

The effects of the disclosure are not limited to those mentioned above, and other effects that are not mentioned may be clearly understood by one of ordinary skill in the art from the scope of claims.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A test method for evaluating cognitive function decline, the test method being executed by a processor of a test apparatus for evaluating cognitive function decline, and comprising:

performing a testing stage of testing how many missions presented for each of a plurality of test items a user performs, and calculating a test score for each of the plurality of test items; performing a category classifying stage of classifying at least one test item from among the plurality of test items as one neurocognitive category from among a plurality of neurocognitive categories based on a type of the test item;

performing an evaluating stage of evaluating whether there is cognitive function decline in the one neurocognitive category, based on a test score of the at least one test item classified as the one neurocognitive category; and in response to determining that there is the cognitive function decline in the one neurocognitive category, performing an additional test tailored to the one neurocognitive category to more accurately evaluate a level of the decline in the one neurocognitive category and detect a certain level of cognitive impairment occurred in a pre-dementia stage, wherein the category classifying stage comprises:

classifying one of the test items as a first neurocognitive category for determining cognitive function decline in memory or as a fifth neurocognitive category for determining cognitive function decline in executive attention.

2. The test method of claim 1, wherein the performing of the testing stage comprises:

a third testing stage of executing a test on a third test item for evaluating how accurately and quickly an arbitrary number matched to a presented symbol image within a pre-set time limit after looking at the presented symbol image and calculating a third test score, wherein the category classifying stage comprises:

classifying the third test item as a fifth neurocognitive category for determining cognitive function decline in executive attention.

3. The test method of claim 1, wherein the performing of the testing stage comprises:

a seventh testing stage of executing a test on a seventh test item for evaluating how accurately and quickly a presented number is selected within a pre-set time limit and presenting numbers and days and evaluating how accurately and quickly a day corresponding to a number is selected and calculating a seventh test score, wherein the category classifying stage comprises:

classifying the seventh test item as a fifth neurocognitive category for determining cognitive function decline in executive attention.

4. The test method of claim 1, wherein the performing of the testing stage comprises:

a first testing stage of executing a test on a first test item for evaluating how many words corresponding to a pre-set presented category the user utters within a time limit and calculating a first test score, wherein the category classifying stage comprises:

classifying the first test item as a fifth neurocognitive category for determining cognitive function decline in executive attention.

5. The test method of claim 1, wherein the performing of the testing stage comprises:

a second testing stage of executing a test on a second test item for learning words or images while informing pre-set category clues and evaluating how many of the learned words or images are remembered after a pre-set time has elapsed and calculating a second test score, wherein the category classifying stage comprises:

classifying the second test item as a first neurocognitive category for determining cognitive function decline in memory.

6. The test method of claim 1, wherein the performing of the testing stage comprises:

a fourth testing stage of executing a test on a fourth test item for learning a pre-set presented image and evaluating how much of the learned presented image is remembered after a pre-set time has elapsed and calculating a fourth test score, wherein the category classifying stage comprises:

classifying the fourth test item as a first neurocognitive category for determining cognitive function decline in memory.

7. The test method of claim 1, wherein the performing of the testing stage comprises:

a fifth testing stage of executing a test on a fifth test item for evaluating whether a pre-set presented word and a color of the pre-set presented word are accurately uttered and calculating a fifth test score, wherein the category classifying stage comprises:

classifying the fifth test item as a fifth neurocognitive category for determining cognitive function decline in executive attention.

8. The test method of claim 1, further comprising:

in response to determining that there is the cognitive function decline in the one neurocognitive category, displaying, on a screen of the test apparatus, information for treating the cognitive function decline in the one neurocognitive category.

9. The test method of claim 8, wherein the information for treating the cognitive function decline includes hospital locations, doctor information, hospital appointment information, or suggested medical tests.

10. The test method of claim 8, wherein the additional test is a theory of mind test, a facial emotion test, or a color vision test.

11. A non-transitory computer-readable recording medium having stored therein a computer program for executing the test method of claim 1, by using a computer.

12. A test apparatus for evaluating cognitive function decline, the test apparatus comprising:

a screen;

a processor; and a memory operatively connected to the processor and storing at least one code performed by the processor, wherein the memory stores at least one code which, when executed through the processor, causes the processor to:

perform a testing stage of testing how many missions presented for each of a plurality of test items a user performs, and calculating a test score for each of the plurality of test items;

perform a category classification process of classifying at least one test item from among the plurality of test items as one neurocognitive category from among a plurality of neurocognitive categories based on a type of the test item;

perform an evaluation process of evaluating whether there is cognitive function decline in the one neurocognitive category, based on a test score of the at least one test item classified as the one neurocognitive category; and in response to determining that there is the cognitive function decline in the one neurocognitive category, perform an additional test tailored to the one neurocognitive category to more accurately evaluate a level of the decline in the one neurocognitive category and detect a certain level of cognitive impairment occurred in a pre-dementia stage, wherein the memory stores a code which, when executed by the processor, causes the processor to, in performing the category classifying process, classify one of the test items as a first neurocognitive category for determining cognitive function decline in memory or as a fifth neurocognitive category for determining cognitive function decline in executive attention.

13. The test apparatus of claim 12, wherein the memory stores at least one code which, when executed through the processor, causes the processor to:

in response to determining that there is the cognitive function decline in the one neurocognitive category, display, on the screen of the test apparatus, information for treating the cognitive function decline in the one neurocognitive category.

14. The test apparatus of claim 13, wherein the information for treating the cognitive function decline includes hospital locations, doctor information, hospital appointment information, or suggested medical tests.

15. The test apparatus of claim 12, wherein the additional test is a theory of mind test, a facial emotion test, or a color vision test.

\* \* \* \* \*